US010036015B2

(12) United States Patent
Kathju et al.

(10) Patent No.: US 10,036,015 B2
(45) Date of Patent: Jul. 31, 2018

(54) COMPOSITION AND METHODS FOR REDUCED SCARRING AND TREATMENT OF FIBROSIS

(71) Applicant: Sandeep Kathju, Coraopolis, PA (US)

(72) Inventors: Sandeep Kathju, Coraopolis, PA (US); Latha Satish, Wexford, PA (US)

(*) Notice: Subject to any disclaimer, the term of this patent is extended or adjusted under 35 U.S.C. 154(b) by 0 days.

(21) Appl. No.: 14/589,470

(22) Filed: Jan. 5, 2015

(65) Prior Publication Data

US 2015/0132370 A1 May 14, 2015

Related U.S. Application Data

(62) Division of application No. 13/643,975, filed on Jan. 4, 2013.

(51) Int. Cl.
*C12N 15/11* (2006.01)
*C12N 15/113* (2010.01)
*C07K 16/18* (2006.01)

(52) U.S. Cl.
CPC ............ *C12N 15/113* (2013.01); *C07K 16/18* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 2004/0018176 | A1* | 1/2004 | Tolentino ........... | C12N 15/1136 424/93.21 |
| 2004/0072185 | A1 | 4/2004 | Paterini-Brechot et al. | |
| 2004/0171003 | A1* | 9/2004 | Yoshikawa ............ | C07K 14/82 435/6.11 |
| 2006/0199179 | A1* | 9/2006 | Nakamura ........... | C12Q 1/6886 435/6.18 |
| 2008/0019941 | A1 | 1/2008 | Drapeau | |

FOREIGN PATENT DOCUMENTS

| | | | |
|---|---|---|---|
| WO | WO 2004/001072 | A3 | 12/2003 |
| WO | WO2009/085270 | A2 | 7/2009 |

OTHER PUBLICATIONS

Wang et al, Smooth Muscle Actin Determines Mechanical Force-induced p38 Activation, 2005, The Journal of Biological Chemistry, vol. 280, No. 8, 7273-7284.*

GenBank, Rattus rattus mRNA for vascular alpha-actin, 2005, GenBank X06801, pp. 1-2.*

Clement et al, Expression and function of _-smooth muscle actin during embryonic-stem-cell-derived cardiomyocyte differentiation, 2007, Journal of Cell Science, 120, 229-238.*

Satish et al, Downregulation of Chaperonin Containing T-Complex Polypeptide ETA Reduces TGF beta-Induced Cell Migration in Fibroblasts, Mar. 2009, Wound Repair and Regeneration, vol. 17, No. 2, p. A47.*

Satish et al, Reducing chaperonin containing T-complex polypeptide subunit eta (CCT-ETA) decreases alpha-sma expression in adult skin derived fibroblasts, Mar. 2010, Wound Repair and Regeneration, vol. 18, No. 2, p. A17.*

Wang et al, Preparation and Characterization of Agarose Hydrogel Nanoparticles for Protein and Peptide Drug Delivery, 1997, Pharmaceutical Development and Technology, 1997, 2(2), pp. 135-142.*

Meilander NJ et al., titled Sustained Release of Plasmid DNA Using Lipid Microtubules and Agarose Hydrogel; Journal of Controlled Release; 2003, vol. 88, No. 2, p. 321-31 (11 pages).

Japan Patent Office; Office Action; Office Action from Japanese Patent Application No. 2013-508253; copyright dated Apr. 27, 2015; pp. 1-13; publisher Japan Patent Office; Published Tokyo, Japan; copyright dated Apr. 27, 2015; (13 pages) (English translation enclosed).

European Patent Office, Supplementary European Search Report, European Patent Application No. 11778020.5-1401/2563923, pp. 1-10; publisher European Patent Office; Published Munich, Germany; copyright dated Nov. 18, 2014; (11 pages).

Australian Patent Office; Patent Examination Report No. 1; Australian Patent Application No. 2011248566; pp. 1-4; publisher IP Australia; Published Wooden, Australia; copyright dated Nov. 21, 2014; (4 pages).

Darden et al; title RNA differential Display of Scarless Wound Healing in Fetal Rabbit indicates Downregulation of a CCT Chaperonin Subunit and Upregulation of a Glycophorin-Like Gene Transcript; Journal of Pediatric Surgery, vol. 35, No. 3 Mar. 2000: pp. 406-419 (14 pages).

Satish et al., title Cloning and expression of rabbit CCT subinuts eta and beta in healing curaneous wounds; Cell Stress and Chaperones, Nov. 2010;15(6):819-26 (8 pages).

Satish, et al.; titled Chaperonin Containing T-Complex Polypeptide Subunit Eta (CCT-eta) is a Specific Regulator of Fibroblast Motility and Contractility; PLoS OONE, Apr. 2010, vol. 5, Issue 4, e10063 (14 pages).

Satish et al., Genbank Accession FJ349099 Oryctolagus cuniculus Chaperonin-containing T-complex polypeptide eta subunit mRNA, complete cds [online] Nov. 2, 2008 (retrieved Dec. 19, 2011) (2 pages).

Satish et al.; titled Differential expression of chaperonin containing T-complex polypeptide (CCT) subunits during fetal and adult skin wound healing; Cell Stress and Chaperones (2008) 13:527-533 (7 pages).

(Continued)

*Primary Examiner* — Ekaterina Poliakova-Georgantas
(74) *Attorney, Agent, or Firm* — Metz Lewis Brodman Must O'Keefe LLC

(57) ABSTRACT

Embodiments of the present disclosure are directed to methods of treating, reducing or preventing fibrosis or scarring including administering a therapeutic molecular agent selected from the group consisting of an agent that inhibits chaperonin containing T-complex polypeptide subunit eta polypeptide ("CCT-eta"), an agent that inhibits α-Smooth Muscle Actin ("α-SMA"), or a combination thereof. In embodiments, the fibrosis may include Dupuytren's contracture, Peyronie's disease, pulmonary fibrosis, cirrhosis, interstitial lung disease or scarring alopecia.

6 Claims, 33 Drawing Sheets

(56) References Cited

OTHER PUBLICATIONS

European Patent Office, Communication Pursuant to Article 94(3) EPC, Communication from European Application No. 11 778 020.5-1401; pp. 1-6, publisher European Patent Office, published Rijswijk, The Netherlands, copyright dated Feb. 2, 2017; copy enclosed (6 pages).

Annonymous: AteloGene Local & Systemic Use:, Jul. 17, 2009 (Jul. 17, 2009), pp. 1-12.

Minakuchi Yoshiko et al: "Atelocollagen-Mediated Synthetic Small Interfering RNA Delivery for Effective Gene Silencing In Vitro and In Vivo", Nucleic Acids Research, vol. 32, No. 13, Jan. 1, 2004 (Jan. 1, 2004), pp. E109-1.

Takeshita F et al: "Efficient Delivery of Small Interfering RNA to Bone-Metastic Tumors by Using Ateleocollagen In Vivo", Proceedings of the National Academy of Sciences, vol. 102, No. 34, Aug. 23, 2005 (Aug. 23, 2005), p. 12177-12182.

Chen, Xiaoyue, et al, Two Yeast Genes With Similarity to TCP-1 are Required for Microtubule and Actin Function In Vivo; Proc. Natl. Acad. Sci, USA, Cell Biology, Sep. 1994, pp. 9111-9115, vol. 91.

* cited by examiner

SEQUENCE LISTING

```
<160> NUMBER OF SEQ ID NOS: 29

<210> SEQ ID NO 1
<211> LENGTH: 21
<212> TYPE: DNA
<213> ORGANISM: Artificial Sequence
<220> FEATURE:
<223> OTHER INFORMATION: Rabbit CCT-eta siRNA sense sequence

<400> SEQUENCE: 1

gaacgauuca guaguggcut t                                          21


<210> SEQ ID NO 2
<211> LENGTH: 21
<212> TYPE: DNA
```

<213> ORGANISM: Artificial Sequence
<220> FEATURE:
<223> OTHER INFORMATION: Rabbit CCT-eta siRNA antisense sequence

<400> SEQUENCE: 2
agccacuacu gaaucguuct t 21

<210> SEQ ID NO 3
<211> LENGTH: 21
<212> TYPE: DNA
<213> ORGANISM: Artificial Sequence
<220> FEATURE:
<223> OTHER INFORMATION: Scramble Control CCT-eta siRNA sense sequence

<400> SEQUENCE: 3
gaacgauucg aaugcuggut t 21

<210> SEQ ID NO 4
<211> LENGTH: 21
<212> TYPE: DNA
<213> ORGANISM: Artificial Sequence
<220> FEATURE:
<223> OTHER INFORMATION: Scramble Control CCT-eta siRNA antisense sequence

<400> SEQUENCE: 4
accagcauuc gaaucguuct t 21

<210> SEQ ID NO 5
<211> LENGTH: 21
<212> TYPE: DNA
<213> ORGANISM: Artificial Sequence
<220> FEATURE:
<223> OTHER INFORMATION: Rabbit alpha-SMA siRNA sense sequence

<400> SEQUENCE: 5
agagaaauug ugcuauguct t 21

<210> SEQ ID NO 6
<211> LENGTH: 21
<212> TYPE: DNA
<213> ORGANISM: Artificial Sequence
<220> FEATURE:
<223> OTHER INFORMATION: Rabbit alpha-SMA siRNA antisense sequence

<400> SEQUENCE: 6
gacauagcac aauuucucut t 21

<210> SEQ ID NO 7
<211> LENGTH: 1875
<212> TYPE: DNA
<213> ORGANISM: Oryctolagus cuniculus

<400> SEQUENCE: 7
gaggcattgt ggggttgctg ggcggcccgc acacagagaa gagaggagga gtagcgggct 60
actgcataag cttccaagat gatgccaaca ccagttatcc tgttgaaaga ggggactgac 120
agctctcaag gcattcccca gcttgtgagt aacattagtg cctgccaggt gattgctgag 180
gctgtacgaa ccacgctggg ccctcgtggc atggacaaac ttatcgtaga tggccgaggc 240
aaagctacaa tttccaacga tggggccaca atcctgaaac tccttgatgt cgtccatcct 300
gcagcaaaga ctttagtgga catcgcaaaa tcccaggatg ctgaggttgg tgatggaacc 360
acctcagtga ccctgctggc tgcagagttc ctgaagcagg tgaaaccgta tgtggaggaa 420

-continued

```
gggctgcacc cccagatcat catccgtgct ttccgcacag ccacccagtt ggcagttaac    480

aagatcaaag agattgctgt gactgtgaag aagcaagata aagtggagca gaggaagctg    540

ctggagaagt gtgccatgac agcgctgagc tccaagctca tctcccagca gaaagccttc    600

tttgctaaga tggtggttga tgcagtgatg atgcttgatg acttgttgca gcttaaaatg    660

attggaatca agaaggtcca aggtggagcc ctagaggagt ctcagctggt agctggtgtt    720

gcgttcaaga agactttctc ttacgctggg tttgaaatgc aacccaaaaa gtacaataat    780

cctatgattg cccttttaaa tgttgagctt gagctgaagg ctgagaaaga taatgctgaa    840

atcagagtcc acacggttga ggattatcag gcgattgttg atgctgagtg gaacattctc    900

tatgacaagt tagagaagat ctaccattcg ggagccaaag tcatcttgtc caaactgccc    960

attggggacg tggccaccca gtactttgct gacagggaca tgttctgtgc cggccgagtg   1020

cctgaggagg atctgaagag gacgatgatg gcctgtggtg gctccatcca gaccagtgtg   1080

aatgctctgt caccagacgt gttgggccgc tgccaggtgt ttgaagagac ccagattgga   1140

ggcgagagat ataatttctt cactggctgc cccaaggcca agacttgcac cttcatcctc   1200

cgaggtggtg ctgagcagtt tatggaggag acggagcggt ccctgcatga tgccatcatg   1260

attgtcagga gggccattaa gaacgattca gtagtggctg gtggcggggc cattgagatg   1320

gagctttcca agtacctgcg agattactca aggactattc caggaaaaca gcagctgttg   1380

attggggcgt atgccaaggc cttggagatc atcccacgtc agctgtgtga caacgctggt   1440

ttcgatgcca caaacatcct caacaagctg cgggctcggc atgcccaggg cggcatgtgg   1500

tacggggtgg acatcaacaa cgaggacatt gccgacaact ttgaggcctt tgtgtgggag   1560

ccggcgatgg tgcgcatcaa cgccttgacg gcagcctcgg aggcagcatg ccttatcgtg   1620

tccgtagatg aaaccatcaa gaaccccccgc tcgactgtgg atgcaccgcc agcagcaggc   1680

cgtggccgag gccgtggccg tccccattga ggggcaccct gtccatcgta tggctgctta   1740

cagggtccat ttgctgtccc cgccttggtt agttgctgtt acaaggaagg gatagtaatt   1800

ggcccaactt ctccctggat ggtatttaaa taaaagttaa cacttagagt taactttgta   1860

agttaaaaaa aaaaa                                                    1875


<210> SEQ ID NO 8
<211> LENGTH: 1337
<212> TYPE: DNA
<213> ORGANISM: Oryctolagus cuniculus

<400> SEQUENCE: 8

ggcacgaggg agaagcccag cccagcactg tcaggaatcc cgtgaagcag ctgcagctat     60

gtgtgaggaa gaggacagca ccgcccttgt gtgtgacaat ggctccgggc tctgtaaggc    120

tggctttgcc ggagacgatg ctccaagagc tgttttccca tccattgtgg gacgtcccag    180

gcaccagggg gtgatggtgg gaatggggca aaaagacagc tacgtgggtg atgaagcgca    240

gagcaaaaga ggaatcctga ccttgaagta cccgatcgaa catggcatca tcaccaactg    300

ggacgacatg gaaaagatct ggcaccactc cttctacaat gagcttcgcg ttgcccctga    360

agaacatcca accctgttga ctgaggcacc gctgaacccc aaagccaacc gggagaaaat    420

gacccagatt atgtttgaga ctttcaatgt cccagccatg tacgtggcta ttcaggcggt    480

gctgtccctc tatgcctctg gacgtacaac tggcattgtg ctggactctg gagatggtgt    540

cacccacaac gtgcccatct atgagggcta tgccctgccc catgccatca tgcgtctgga    600

cctggcaggc cgagatctca ctgactacct catgaagatc ctgactgagc gtggctattc    660
```

-continued

```
cttcgtgact actgctgaac gtgagattgt ccgggacatc aaagagaaat tgtgctatgt    720

cgctctggac tttgaaaacg agatggccac tgctgcatcc tcctcctccc tcgagaagag    780

ctatgagctg cctgacgggc aggtgatcac catcgggaac gaacgcttcc gctgcccaga    840

gaccctgttc cagccctcct tcatcgggat ggaatctgct ggcatccatg aaaccaccta    900

caacagcatc atgaagtgtg acatcgacat caggaaggac ctctatgcta acaatgtgct    960

ctcagggggc accaccatgt accctggcat tgctgaccgt atgcagaagg aaatcacggc   1020

cctagctccc agcaccatga agatcaagat aattgcccct ccagagcgca aatactccgt   1080

ctggatcggc ggctccatcc tggcctctct gtccaccttt cagcagatgt ggatcagcaa   1140

acaggagtac gatgaagccg ggccctccat tgtccaccgc aaatgcttct aagtcacttc   1200

cctgctctgt ttctagccca caactgtgaa tgtgttgtgg aataatgcct tcaattcctt   1260

tccaagtcat gcctatccaa agctctgact cattacctat gtattttta ataaatctga   1320

aatatgctac cagtcaa                                                  1337
```

```
<210> SEQ ID NO 9
<211> LENGTH: 543
<212> TYPE: PRT
<213> ORGANISM: Oryctolagus cuniculus

<400> SEQUENCE: 9

Met Met Pro Thr Pro Val Ile Leu Leu Lys Glu Gly Thr Asp Ser Ser
1               5                   10                  15

Gln Gly Ile Pro Gln Leu Val Ser Asn Ile Ser Ala Cys Gln Val Ile
            20                  25                  30

Ala Glu Ala Val Arg Thr Thr Leu Gly Pro Arg Gly Met Asp Lys Leu
        35                  40                  45

Ile Val Asp Gly Arg Gly Lys Ala Thr Ile Ser Asn Asp Gly Ala Thr
    50                  55                  60

Ile Leu Lys Leu Leu Asp Val Val His Pro Ala Ala Lys Thr Leu Val
65                  70                  75                  80

Asp Ile Ala Lys Ser Gln Asp Ala Glu Val Gly Asp Gly Thr Thr Ser
                85                  90                  95

Val Thr Leu Leu Ala Ala Glu Phe Leu Lys Gln Val Lys Pro Tyr Val
            100                 105                 110

Glu Glu Gly Leu His Pro Gln Ile Ile Ile Arg Ala Phe Arg Thr Ala
        115                 120                 125

Thr Gln Leu Ala Val Asn Lys Ile Lys Glu Ile Ala Val Thr Val Lys
    130                 135                 140

Lys Gln Asp Lys Val Glu Gln Arg Lys Leu Leu Glu Lys Cys Ala Met
145                 150                 155                 160

Thr Ala Leu Ser Ser Lys Leu Ile Ser Gln Gln Lys Ala Phe Phe Ala
                165                 170                 175

Lys Met Val Val Asp Ala Val Met Met Leu Asp Asp Leu Leu Gln Leu
            180                 185                 190

Lys Met Ile Gly Ile Lys Lys Val Gln Gly Gly Ala Leu Glu Glu Ser
        195                 200                 205

Gln Leu Val Ala Gly Val Ala Phe Lys Lys Thr Phe Ser Tyr Ala Gly
    210                 215                 220

Phe Glu Met Gln Pro Lys Lys Tyr Asn Asn Pro Met Ile Ala Leu Leu
225                 230                 235                 240

Asn Val Glu Leu Glu Leu Lys Ala Glu Lys Asp Asn Ala Glu Ile Arg
```

-continued

```
                245                 250                 255

Val His Thr Val Glu Asp Tyr Gln Ala Ile Val Asp Ala Glu Trp Asn
            260                 265                 270

Ile Leu Tyr Asp Lys Leu Glu Lys Ile Tyr His Ser Gly Ala Lys Val
        275                 280                 285

Ile Leu Ser Lys Leu Pro Ile Gly Asp Val Ala Thr Gln Tyr Phe Ala
    290                 295                 300

Asp Arg Asp Met Phe Cys Ala Gly Arg Val Pro Glu Glu Asp Leu Lys
305                 310                 315                 320

Arg Thr Met Met Ala Cys Gly Gly Ser Ile Gln Thr Ser Val Asn Ala
                325                 330                 335

Leu Ser Pro Asp Val Leu Gly Arg Cys Gln Val Phe Glu Glu Thr Gln
            340                 345                 350

Ile Gly Gly Glu Arg Tyr Asn Phe Phe Thr Gly Cys Pro Lys Ala Lys
        355                 360                 365

Thr Cys Thr Phe Ile Leu Arg Gly Gly Ala Glu Gln Phe Met Glu Glu
    370                 375                 380

Thr Glu Arg Ser Leu His Asp Ala Ile Met Ile Val Arg Arg Ala Ile
385                 390                 395                 400

Lys Asn Asp Ser Val Val Ala Gly Gly Gly Ala Ile Glu Met Glu Leu
                405                 410                 415

Ser Lys Tyr Leu Arg Asp Tyr Ser Arg Thr Ile Pro Gly Lys Gln Gln
            420                 425                 430

Leu Leu Ile Gly Ala Tyr Ala Lys Ala Leu Glu Ile Ile Pro Arg Gln
        435                 440                 445

Leu Cys Asp Asn Ala Gly Phe Asp Ala Thr Asn Ile Leu Asn Lys Leu
    450                 455                 460

Arg Ala Arg His Ala Gln Gly Gly Met Trp Tyr Gly Val Asp Ile Asn
465                 470                 475                 480

Asn Glu Asp Ile Ala Asp Asn Phe Glu Ala Phe Val Trp Glu Pro Ala
                485                 490                 495

Met Val Arg Ile Asn Ala Leu Thr Ala Ala Ser Glu Ala Ala Cys Leu
            500                 505                 510

Ile Val Ser Val Asp Glu Thr Ile Lys Asn Pro Arg Ser Thr Val Asp
        515                 520                 525

Ala Pro Pro Ala Ala Gly Arg Gly Arg Gly Arg Gly Arg Pro His
    530                 535                 540


<210> SEQ ID NO 10
<211> LENGTH: 376
<212> TYPE: PRT
<213> ORGANISM: Oryctolagus cuniculus

<400> SEQUENCE: 10

Met Cys Glu Glu Glu Asp Ser Thr Ala Leu Val Cys Asp Asn Gly Ser
1               5                   10                  15

Gly Leu Cys Lys Ala Gly Phe Ala Gly Asp Asp Ala Pro Arg Ala Val
            20                  25                  30

Phe Pro Ser Ile Val Gly Arg Pro Arg His Gln Gly Val Met Val Gly
        35                  40                  45

Met Gly Gln Lys Asp Ser Tyr Val Gly Asp Glu Ala Gln Ser Lys Arg
    50                  55                  60

Gly Ile Leu Thr Leu Lys Tyr Pro Ile Glu His Gly Ile Ile Thr Asn
65                  70                  75                  80
```

-continued

```
Trp Asp Asp Met Glu Lys Ile Trp His His Ser Phe Tyr Asn Glu Leu
                85                  90                  95

Arg Val Ala Pro Glu Glu His Pro Thr Leu Leu Thr Glu Ala Pro Leu
            100                 105                 110

Asn Pro Lys Ala Asn Arg Glu Lys Met Thr Gln Ile Met Phe Glu Thr
        115                 120                 125

Phe Asn Val Pro Ala Met Tyr Val Ala Ile Gln Ala Val Leu Ser Leu
    130                 135                 140

Tyr Ala Ser Gly Arg Thr Thr Gly Ile Val Leu Asp Ser Gly Asp Gly
145                 150                 155                 160

Val Thr His Asn Val Pro Ile Tyr Glu Gly Tyr Ala Leu Pro His Ala
                165                 170                 175

Ile Met Arg Leu Asp Leu Ala Gly Arg Asp Leu Thr Asp Tyr Leu Met
            180                 185                 190

Lys Ile Leu Thr Glu Arg Gly Tyr Ser Phe Val Thr Thr Ala Glu Arg
        195                 200                 205

Glu Ile Val Arg Asp Ile Lys Glu Lys Leu Cys Tyr Val Ala Leu Asp
    210                 215                 220

Phe Glu Asn Glu Met Ala Thr Ala Ala Ser Ser Ser Ser Leu Glu Lys
225                 230                 235                 240

Ser Tyr Glu Leu Pro Asp Gly Gln Val Ile Thr Ile Gly Asn Glu Arg
                245                 250                 255

Phe Arg Cys Pro Glu Thr Leu Phe Gln Pro Ser Phe Ile Gly Met Glu
            260                 265                 270

Ser Ala Gly His Glu Thr Thr Tyr Asn Ser Ile Met Lys Cys Asp Ile
        275                 280                 285

Asp Ile Arg Lys Asp Leu Tyr Ala Asn Asn Val Leu Ser Gly Gly Thr
    290                 295                 300

Thr Met Tyr Pro Gly Ile Ala Asp Arg Met Gln Lys Glu Ile Thr Ala
305                 310                 315                 320

Leu Ala Pro Ser Thr Met Lys Ile Lys Ile Ile Ala Pro Pro Glu Arg
                325                 330                 335

Lys Tyr Ser Val Trp Ile Gly Gly Ser Ile Leu Ala Ser Leu Ser Thr
            340                 345                 350

Phe Gln Gln Met Trp Ile Ser Lys Gln Glu Tyr Asp Glu Ala Gly Pro
        355                 360                 365

Ser Ile Val His Arg Lys Cys Phe
    370                 375
```

<210> SEQ ID NO 11
<211> LENGTH: 1336
<212> TYPE: DNA
<213> ORGANISM: Homo sapiens

<400> SEQUENCE: 11

```
atagagtagc ggaagtggtc cgttctcttc ctctcccggc ccaagcttct gggtatttct      60

attgcgcgag gcattgtggg ttgctgggcg gcccggtctc ggagaagagg ggagagtggc     120

gggccgctga ataagcttcc aaaatgatgg attctcagct ggtagctggt gttgcattca     180

agaagacttt ctcttacgct gggtttgaaa tgcaacccaa aaagtaccac aatcccaaga     240

ttgccctttt gaatgtcgag ctcgagttga aagctgagaa agacaatgct gagataagag     300

tccacacagt tgaggattat caggcaattg ttgatgctga gtggaacatt ctctatgaca     360

agttagagaa gatccatcat tctggagcca aagttgtctt gtccaaactc cccattgggg     420
```

atgtggccac ccagtacttt gctgacaggg acatgttctg tgctggccga gtacctgagg 480
aggatctgaa gaggacaatg atggcctgtg gaggctcaat ccagaccagt gtgaatgctc 540
tgtcagcaga tgtgctgggt cgatgccagg tgtttgaaga gacccagatt ggaggcgaga 600
ggtacaattt ttttactggc tgccccaagg ccaagacatg caccttcatt ctccgtggcg 660
gcgccgagca gtttatggag gagacagagc ggtccctgca tgatgccatc atgatcgtca 720
ggagggccat caagaatgat tcagtggtgg ctggtggcgg ggccattgag atggaactct 780
ccaagtacct gcgggattac tcaaggacta ttccaggaaa acagcagctg ttgattgggg 840
catatgccaa ggccttggag attatcccac gccagctgtg tgacaatgct ggctttgatg 900
ccacaaacat tctcaacaag ctgcgggctc ggcatgccca ggggggtaca tggtatggag 960
tagacatcaa caacgaggac attgctgaca actttgaagc tttcgtgtgg gagccagcta 1020
tggtgcggat caatgcgctg acagcagcct ctgaggctgc gtgcctgatc gtgtctgtag 1080
atgaaaccat caagaacccc cgctcgactg tggatgctcc cacagcagca ggccggggcc 1140
gtggtcgtgg ccgcccccac tgagaggcac ccccacccatc acatggctgg ctggctgctg 1200
ggtgcactta ccctccttgg cttggttact tcattttaca aggaaggggt agtaattggc 1260
ccactctctt cttactggag gctatttaaa taaaatgtaa gacttcagat aactttgtaa 1320
attaaaaaaa aaaaaa 1336

<210> SEQ ID NO 12
<211> LENGTH: 1687
<212> TYPE: DNA
<213> ORGANISM: Homo sapiens

<400> SEQUENCE: 12
atagagtagc ggaagtggtc cgttctcttc ctctcccggc ccaagcttct gggtatttct 60
attgcgcgag gcattgtggg ttgctgggcg gcccggtctc ggagaagagg ggagagtggc 120
gggccgctga ataagcttcc aaaatgatgg tgggtgatgg caccacctca gtgaccttgc 180
tggctgcaga gtttctgaag caggtgaaac cctatgtgga ggaaggttta cacccccaga 240
tcatcattcg agctttccgc acagccaccc agctggcagt taacaagatc aaagagattg 300
ctgtgaccgt gaagaaggca gataaagtgg agcagaggaa gctgctggaa aagtgtgcca 360
tgaccgctct gagctccaag ctgatctccc agcagaaagc tttctttgct aagatggtgg 420
tggatgcagt gatgatgctc gatgatttgc tgcagcttaa aatgattgga atcaagaagg 480
tacagggtgg agccctcgag gattctcagc tggtagctgg tgttgcattc aagaagactt 540
tctcttacgc tgggtttgaa atgcaaccca aaaagtacca caatcccaag attgcccttt 600
tgaatgtcga gctcgagttg aaagctgaga aagacaatgc tgagataaga gtccacacag 660
ttgaggatta tcaggcaatt gttgatgctg agtggaacat tctctatgac aagttagaga 720
agatccatca ttctggagcc aaagttgtct tgtccaaact ccccattggg gatgtggcca 780
cccagtactt tgctgacagg gacatgttct gtgctggccg agtacctgag gaggatctga 840
agaggacaat gatggcctgt ggaggctcaa tccagaccag tgtgaatgct ctgtcagcag 900
atgtgctggg tcgatgccag gtgtttgaag agacccagat tggaggcgag aggtacaatt 960
tttttactgg ctgccccaag gccaagacat gcaccttcat tctccgtggc ggcgccgagc 1020
agtttatgga ggagacagag cggtccctgc atgatgccat catgatcgtc aggagggcca 1080
tcaagaatga ttcagtggtg gctggtggcg gggccattga gatggaactc tccaagtacc 1140
tgcgggatta ctcaaggact attccaggaa aacagcagct gttgattggg gcatatgcca 1200

-continued aggccttgga gattatccca cgccagctgt gtgacaatgc tggctttgat gccacaaaca 1260
ttctcaacaa gctgcgggct cggcatgccc agggggtac atggtatgga gtagacatca 1320
acaacgagga cattgctgac aactttgaag ctttcgtgtg ggagccagct atggtgcgga 1380
tcaatgcgct gacagcagcc tctgaggctg cgtgcctgat cgtgtctgta gatgaaacca 1440
tcaagaaccc ccgctcgact gtggatgctc ccacagcagc aggccggggc cgtggtcgtg 1500
gccgccccca ctgagaggca ccccacccat cacatggctg gctggctgct gggtgcactt 1560
accctccttg gcttggttac ttcattttac aaggaagggg tagtaattgg cccactctct 1620
tcttactgga ggctatttaa ataaaatgta agacttcaga taactttgta aattaaaaaa 1680
aaaaaaa 1687

<210> SEQ ID NO 13
<211> LENGTH: 2044
<212> TYPE: DNA
<213> ORGANISM: Homo sapiens

<400> SEQUENCE: 13
atagagtagc ggaagtggtc cgttctcttc ctctcccggc ccaagcttct gggtatttct 60
attgcgcgag gcattgtggg ttgctgggcg gcccggtctc ggagaagagg ggagagtggc 120
gggccgctga ataagcttcc aaaatgatgc attgctcatt cttgaagtcg tcttcatctt 180
ctgtgcagag gcagcatagt acagcagttg agagtaaggc ctctggagct acactgaatg 240
cctagcccac accagttatc ctattgaaag aggggactga tagctcccaa ggcatccccc 300
agcttgtgag taacatcagt gcctgccagg tgattgctga ggctgtaaga actaccctgg 360
gtccccgtgg catggacaag cttattgtag atggcagagg caaagcaaca atttctaatg 420
atggggccac aattctgaaa cttcttgatg ttgtccatcc tgcagcaaag actttggtag 480
acattgccaa atcccaagat gctgaggtgg gtgatggcac cacctcagtg accttgctgg 540
ctgcagagtt tctgaagcag gtgaaaccct atgtggagga aggtttacac ccccagatca 600
tcattcgagc tttccgcaca gccacccagc tggcagttaa caagatcaaa gagattgctg 660
tgaccgtgaa gaaggcagat aaagtggagc agaggaagct gctggaaaag tgtgccatga 720
ccgctctgag ctccaagctg atctcccagc agaaagcttt ctttgctaag atggtggtgg 780
atgcagtgat gatgctcgat gatttgctgc agcttaaaat gattggaatc aagaaggtac 840
agggtggagc cctcgaggat tctcagctgg tagctggtgt tgcattcaag aagacttttct 900 cttacgctgg gtttgaaatg caacccaaaa agtaccacaa tcccaagatt gccctttttga 960 atgtcgagct cgagttgaaa gctgagaaag acaatgctga gataagagtc cacacagttg 1020
aggattatca ggcaattgtt gatgctgagt ggaacattct ctatgacaag ttagagaaga 1080
tccatcattc tggagccaaa gttgtcttgt ccaaactccc cattggggat gtggccaccc 1140
agtactttgc tgacagggac atgttctgtg ctggccgagt acctgaggag gatctgaaga 1200
ggacaatgat ggcctgtgga ggctcaatcc agaccagtgt gaatgctctg tcagcagatg 1260
tgctgggtcg atgccaggtg tttgaagaga cccagattgg aggcgagagg tacaattttt 1320
ttactggctg ccccaaggcc aagacatgca ccttcattct ccgtggcggc gccgagcagt 1380
ttatggagga gacagagcgg tccctgcatg atgccatcat gatcgtcagg agggccatca 1440
agaatgattc agtggtggct ggtggcgggg ccattgagat ggaactctcc aagtacctgc 1500
gggattactc aaggactatt ccaggaaaac agcagctgtt gattggggca tatgccaagg 1560

-continued ccttggagat tatcccacgc cagctgtgtg acaatgctgg ctttgatgcc acaaacattc 1620
tcaacaagct gcgggctcgg catgcccagg ggggtacatg gtatggagta gacatcaaca 1680
acgaggacat tgctgacaac tttgaagctt tcgtgtggga gccagctatg gtgcggatca 1740
atgcgctgac agcagcctct gaggctgcgt gcctgatcgt gtctgtagat gaaaccatca 1800
agaacccccg ctcgactgtg gatgctccca cagcagcagg ccggggccgt ggtcgtggcc 1860
gcccccactg agaggcaccc cacccatcac atggctggct ggctgctggg tgcacttacc 1920
ctccttggct tggttacttc attttacaag gaaggggtag taattggccc actctcttct 1980
tactggaggc tatttaaata aaatgtaaga cttcagataa ctttgtaaat taaaaaaaaa 2040
aaaa 2044

<210> SEQ ID NO 14
<211> LENGTH: 1948
<212> TYPE: DNA
<213> ORGANISM: Homo sapiens

<400> SEQUENCE: 14
atagagtagc ggaagtggtc cgttctcttc ctctcccggc ccaagcttct gggtatttct 60
attgcgcgag gcattgtggg ttgctgggcg gcccggtctc ggagaagagg ggagagtggc 120
gggccgctga ataagcttcc aaaatgatgc ccacaccagt tatcctattg aaagagggga 180
ctgatagctc ccaaggcatc ccccagcttg tgagtaacat cagtgcctgc caggtgattg 240
ctgaggctgt aagaactacc ctgggtcccc gtggcatgga caagcttatt gtagatggca 300
gaggcaaagc aacaatttct aatgatgggg ccacaattct gaaacttctt gatgttgtcc 360
atcctgcagc aaagactttg gtagacattg ccaaatccca agatgctgag gtgggtgatg 420
gcaccacctc agtgaccttg ctggctgcag agtttctgaa gcaggtgaaa ccctatgtgg 480
aggaaggttt acaccccccag atcatcattc gagctttccg cacagccacc cagctggcag 540
ttaacaagat caaagagatt gctgtgaccg tgaagaaggc agataaagtg gagcagagga 600
agctgctgga aaagtgtgcc atgaccgctc tgagctccaa gctgatctcc cagcagaaag 660
ctttctttgc taagatggtg gtggatgcag tgatgatgct cgatgatttg ctgcagctta 720
aaatgattgg aatcaagaag gtacagggtg gagccctcga ggattctcag ctggtagctg 780
gtgttgcatt caagaagact ttctcttacg ctgggtttga aatgcaaccc aaaaagtacc 840
acaatcccaa gattgccctt ttgaatgtcg agctcgagtt gaaagctgag aaagacaatg 900
ctgagataag agtccacaca gttgaggatt atcaggcaat tgttgatgct gagtggaaca 960
ttctctatga caagttagag aagatccatc attctggagc caaagttgtc ttgtccaaac 1020
tccccattgg ggatgtggcc acccagtact ttgctgacag ggacatgttc tgtgctggcc 1080
gagtacctga ggaggatctg aagaggacaa tgatggcctg tggaggctca atccagacca 1140
gtgtgaatgc tctgtcagca gatgtgctgg gtcgatgcca ggtgtttgaa gagacccaga 1200
ttggaggcga gaggtacaat ttttttactg gctgccccaa ggccaagaca tgcaccttca 1260
ttctccgtgg cggcgccgag cagtttatgg aggagacaga gcggtccctg catgatgcca 1320
tcatgatcgt caggagggcc atcaagaatg attcagtggt ggctggtggc ggggccattg 1380
agatggaact ctccaagtac ctgcgggatt actcaaggac tattccagga aaacagcagc 1440
tgttgattgg ggcatatgcc aaggccttgg agattatccc acgccagctg tgtgacaatg 1500
ctggctttga tgccacaaac attctcaaca agctgcgggc tcggcatgcc caggggggta 1560
catggtatgg agtagacatc aacaacgagg acattgctga caactttgaa gctttcgtgt 1620
gggagccagc tatggtgcgg atcaatgcgc tgacagcagc ctctgaggct gcgtgcctga 1680
tcgtgtctgt agatgaaacc atcaagaacc cccgctcgac tgtggatgct cccacagcag 1740
caggccgggg ccgtggtcgt ggccgccccc actgagaggc accccaccca tcacatggct 1800
ggctggctgc tgggtgcact taccctcctt ggcttggtta cttcatttta caaggaaggg 1860
gtagtaattg gcccactctc ttcttactgg aggctattta aataaaatgt aagacttcag 1920
ataactttgt aaattaaaaa aaaaaaaa 1948

<210> SEQ ID NO 15
<211> LENGTH: 339
<212> TYPE: PRT
<213> ORGANISM: Homo sapiens

<400> SEQUENCE: 15

Met Met Asp Ser Gln Leu Val Ala Gly Val Ala Phe Lys Lys Thr Phe
1 5 10 15

Ser Tyr Ala Gly Phe Glu Met Gln Pro Lys Lys Tyr His Asn Pro Lys
20 25 30

Ile Ala Leu Leu Asn Val Glu Leu Glu Leu Lys Ala Glu Lys Asp Asn
35 40 45

Ala Glu Ile Arg Val His Thr Val Glu Asp Tyr Gln Ala Ile Val Asp
50 55 60

Ala Glu Trp Asn Ile Leu Tyr Asp Lys Leu Glu Lys Ile His His Ser
65 70 75 80

Gly Ala Lys Val Val Leu Ser Lys Leu Pro Ile Gly Asp Val Ala Thr
85 90 95

Gln Tyr Phe Ala Asp Arg Asp Met Phe Cys Ala Gly Arg Val Pro Glu
100 105 110

Glu Asp Leu Lys Arg Thr Met Met Ala Cys Gly Gly Ser Ile Gln Thr
115 120 125

Ser Val Asn Ala Leu Ser Ala Asp Val Leu Gly Arg Cys Gln Val Phe
130 135 140

Glu Glu Thr Gln Ile Gly Gly Glu Arg Tyr Asn Phe Phe Thr Gly Cys
145 150 155 160

Pro Lys Ala Lys Thr Cys Thr Phe Ile Leu Arg Gly Gly Ala Glu Gln
165 170 175

Phe Met Glu Glu Thr Glu Arg Ser Leu His Asp Ala Ile Met Ile Val
180 185 190

Arg Arg Ala Ile Lys Asn Asp Ser Val Val Ala Gly Gly Gly Ala Ile
195 200 205

Glu Met Glu Leu Ser Lys Tyr Leu Arg Asp Tyr Ser Arg Thr Ile Pro
210 215 220

Gly Lys Gln Gln Leu Leu Ile Gly Ala Tyr Ala Lys Ala Leu Glu Ile
225 230 235 240

Ile Pro Arg Gln Leu Cys Asp Asn Ala Gly Phe Asp Ala Thr Asn Ile
245 250 255

Leu Asn Lys Leu Arg Ala Arg His Ala Gln Gly Gly Thr Trp Tyr Gly
260 265 270

Val Asp Ile Asn Asn Glu Asp Ile Ala Asp Asn Phe Glu Ala Phe Val
275 280 285

Trp Glu Pro Ala Met Val Arg Ile Asn Ala Leu Thr Ala Ala Ser Glu
290 295 300

Ala Ala Cys Leu Ile Val Ser Val Asp Glu Thr Ile Lys Asn Pro Arg 305 310 315 320

Ser Thr Val Asp Ala Pro Thr Ala Ala Gly Arg Gly Arg Gly Arg Gly
325 330 335

Arg Pro His

<210> SEQ ID NO 16
<211> LENGTH: 456
<212> TYPE: PRT
<213> ORGANISM: Homo sapiens

<400> SEQUENCE: 16

Met Met Val Gly Asp Gly Thr Thr Ser Val Thr Leu Leu Ala Ala Glu
1 5 10 15

Phe Leu Lys Gln Val Lys Pro Tyr Val Glu Glu Gly Leu His Pro Gln
20 25 30

Ile Ile Ile Arg Ala Phe Arg Thr Ala Thr Gln Leu Ala Val Asn Lys
35 40 45

Ile Lys Glu Ile Ala Val Thr Val Lys Lys Ala Asp Lys Val Glu Gln
50 55 60

Arg Lys Leu Leu Glu Lys Cys Ala Met Thr Ala Leu Ser Ser Lys Leu
65 70 75 80

Ile Ser Gln Gln Lys Ala Phe Phe Ala Lys Met Val Val Asp Ala Val
85 90 95

Met Met Leu Asp Asp Leu Leu Gln Leu Lys Met Ile Gly Ile Lys Lys
100 105 110

Val Gln Gly Gly Ala Leu Glu Asp Ser Gln Leu Val Ala Gly Val Ala
115 120 125

Phe Lys Lys Thr Phe Ser Tyr Ala Gly Phe Glu Met Gln Pro Lys Lys
130 135 140

Tyr His Asn Pro Lys Ile Ala Leu Leu Asn Val Glu Leu Glu Leu Lys
145 150 155 160

Ala Glu Lys Asp Asn Ala Glu Ile Arg Val His Thr Val Glu Asp Tyr
165 170 175

Gln Ala Ile Val Asp Ala Glu Trp Asn Ile Leu Tyr Asp Lys Leu Glu
180 185 190

Lys Ile His His Ser Gly Ala Lys Val Val Leu Ser Lys Leu Pro Ile
195 200 205

Gly Asp Val Ala Thr Gln Tyr Phe Ala Asp Arg Asp Met Phe Cys Ala
210 215 220

Gly Arg Val Pro Glu Glu Asp Leu Lys Arg Thr Met Met Ala Cys Gly
225 230 235 240

Gly Ser Ile Gln Thr Ser Val Asn Ala Leu Ser Ala Asp Val Leu Gly
245 250 255

Arg Cys Gln Val Phe Glu Glu Thr Gln Ile Gly Gly Glu Arg Tyr Asn
260 265 270

Phe Phe Thr Gly Cys Pro Lys Ala Lys Thr Cys Thr Phe Ile Leu Arg
275 280 285

Gly Gly Ala Glu Gln Phe Met Glu Glu Thr Glu Arg Ser Leu His Asp
290 295 300

Ala Ile Met Ile Val Arg Arg Ala Ile Lys Asn Asp Ser Val Val Ala
305 310 315 320

Gly Gly Gly Ala Ile Glu Met Glu Leu Ser Lys Tyr Leu Arg Asp Tyr
325 330 335

Ser Arg Thr Ile Pro Gly Lys Gln Gln Leu Leu Ile Gly Ala Tyr Ala

```
            340                 345                 350

Lys Ala Leu Glu Ile Ile Pro Arg Gln Leu Cys Asp Asn Ala Gly Phe
        355                 360                 365

Asp Ala Thr Asn Ile Leu Asn Lys Leu Arg Ala Arg His Ala Gln Gly
    370                 375                 380

Gly Thr Trp Tyr Gly Val Asp Ile Asn Asn Glu Asp Ile Ala Asp Asn
385                 390                 395                 400

Phe Glu Ala Phe Val Trp Glu Pro Ala Met Val Arg Ile Asn Ala Leu
                405                 410                 415

Thr Ala Ala Ser Glu Ala Ala Cys Leu Ile Val Ser Val Asp Glu Thr
            420                 425                 430

Ile Lys Asn Pro Arg Ser Thr Val Asp Ala Pro Thr Ala Ala Gly Arg
        435                 440                 445

Gly Arg Gly Arg Gly Arg Pro His
    450                 455


<210> SEQ ID NO 17
<211> LENGTH: 499
<212> TYPE: PRT
<213> ORGANISM: Homo sapiens

<400> SEQUENCE: 17

Met Asp Lys Leu Ile Val Asp Gly Arg Gly Lys Ala Thr Ile Ser Asn
1               5                   10                  15

Asp Gly Ala Thr Ile Leu Lys Leu Leu Asp Val Val His Pro Ala Ala
            20                  25                  30

Lys Thr Leu Val Asp Ile Ala Lys Ser Gln Asp Ala Glu Val Gly Asp
        35                  40                  45

Gly Thr Thr Ser Val Thr Leu Leu Ala Ala Glu Phe Leu Lys Gln Val
    50                  55                  60

Lys Pro Tyr Val Glu Glu Gly Leu His Pro Gln Ile Ile Ile Arg Ala
65                  70                  75                  80

Phe Arg Thr Ala Thr Gln Leu Ala Val Asn Lys Ile Lys Glu Ile Ala
                85                  90                  95

Val Thr Val Lys Lys Ala Asp Lys Val Glu Gln Arg Lys Leu Leu Glu
            100                 105                 110

Lys Cys Ala Met Thr Ala Leu Ser Ser Lys Leu Ile Ser Gln Gln Lys
        115                 120                 125

Ala Phe Phe Ala Lys Met Val Val Asp Ala Val Met Met Leu Asp Asp
    130                 135                 140

Leu Leu Gln Leu Lys Met Ile Gly Ile Lys Lys Val Gln Gly Gly Ala
145                 150                 155                 160

Leu Glu Asp Ser Gln Leu Val Ala Gly Val Ala Phe Lys Lys Thr Phe
                165                 170                 175

Ser Tyr Ala Gly Phe Glu Met Gln Pro Lys Lys Tyr His Asn Pro Lys
            180                 185                 190

Ile Ala Leu Leu Asn Val Glu Leu Glu Leu Lys Ala Glu Lys Asp Asn
        195                 200                 205

Ala Glu Ile Arg Val His Thr Val Glu Asp Tyr Gln Ala Ile Val Asp
    210                 215                 220

Ala Glu Trp Asn Ile Leu Tyr Asp Lys Leu Glu Lys Ile His His Ser
225                 230                 235                 240

Gly Ala Lys Val Val Leu Ser Lys Leu Pro Ile Gly Asp Val Ala Thr
                245                 250                 255
```

-continued

```
Gln Tyr Phe Ala Asp Arg Asp Met Phe Cys Ala Gly Arg Val Pro Glu
            260                 265                 270

Glu Asp Leu Lys Arg Thr Met Met Ala Cys Gly Gly Ser Ile Gln Thr
        275                 280                 285

Ser Val Asn Ala Leu Ser Ala Asp Val Leu Gly Arg Cys Gln Val Phe
    290                 295                 300

Glu Glu Thr Gln Ile Gly Gly Glu Arg Tyr Asn Phe Phe Thr Gly Cys
305                 310                 315                 320

Pro Lys Ala Lys Thr Cys Thr Phe Ile Leu Arg Gly Gly Ala Glu Gln
                325                 330                 335

Phe Met Glu Glu Thr Glu Arg Ser Leu His Asp Ala Ile Met Ile Val
            340                 345                 350

Arg Arg Ala Ile Lys Asn Asp Ser Val Val Ala Gly Gly Gly Ala Ile
        355                 360                 365

Glu Met Glu Leu Ser Lys Tyr Leu Arg Asp Tyr Ser Arg Thr Ile Pro
    370                 375                 380

Gly Lys Gln Gln Leu Leu Ile Gly Ala Tyr Ala Lys Ala Leu Glu Ile
385                 390                 395                 400

Ile Pro Arg Gln Leu Cys Asp Asn Ala Gly Phe Asp Ala Thr Asn Ile
                405                 410                 415

Leu Asn Lys Leu Arg Ala Arg His Ala Gln Gly Gly Thr Trp Tyr Gly
            420                 425                 430

Val Asp Ile Asn Asn Glu Asp Ile Ala Asp Asn Phe Glu Ala Phe Val
        435                 440                 445

Trp Glu Pro Ala Met Val Arg Ile Asn Ala Leu Thr Ala Ala Ser Glu
    450                 455                 460

Ala Ala Cys Leu Ile Val Ser Val Asp Glu Thr Ile Lys Asn Pro Arg
465                 470                 475                 480

Ser Thr Val Asp Ala Pro Thr Ala Ala Gly Arg Gly Arg Gly Arg Gly
                485                 490                 495

Arg Pro His


<210> SEQ ID NO 18
<211> LENGTH: 543
<212> TYPE: PRT
<213> ORGANISM: Homo sapiens

<400> SEQUENCE: 18

Met Met Pro Thr Pro Val Ile Leu Leu Lys Glu Gly Thr Asp Ser Ser
1               5                   10                  15

Gln Gly Ile Pro Gln Leu Val Ser Asn Ile Ser Ala Cys Gln Val Ile
            20                  25                  30

Ala Glu Ala Val Arg Thr Thr Leu Gly Pro Arg Gly Met Asp Lys Leu
        35                  40                  45

Ile Val Asp Gly Arg Gly Lys Ala Thr Ile Ser Asn Asp Gly Ala Thr
    50                  55                  60

Ile Leu Lys Leu Leu Asp Val Val His Pro Ala Ala Lys Thr Leu Val
65                  70                  75                  80

Asp Ile Ala Lys Ser Gln Asp Ala Glu Val Gly Asp Gly Thr Thr Ser
                85                  90                  95

Val Thr Leu Leu Ala Ala Glu Phe Leu Lys Gln Val Lys Pro Tyr Val
            100                 105                 110

Glu Glu Gly Leu His Pro Gln Ile Ile Ile Arg Ala Phe Arg Thr Ala
        115                 120                 125
```

```
Thr Gln Leu Ala Val Asn Lys Ile Lys Glu Ile Ala Val Thr Val Lys
    130                 135                 140

Lys Ala Asp Lys Val Glu Gln Arg Lys Leu Leu Glu Lys Cys Ala Met
145                 150                 155                 160

Thr Ala Leu Ser Ser Lys Leu Ile Ser Gln Gln Lys Ala Phe Phe Ala
                165                 170                 175

Lys Met Val Val Asp Ala Val Met Met Leu Asp Asp Leu Leu Gln Leu
            180                 185                 190

Lys Met Ile Gly Ile Lys Lys Val Gln Gly Gly Ala Leu Glu Asp Ser
        195                 200                 205

Gln Leu Val Ala Gly Val Ala Phe Lys Lys Thr Phe Ser Tyr Ala Gly
    210                 215                 220

Phe Glu Met Gln Pro Lys Lys Tyr His Asn Pro Lys Ile Ala Leu Leu
225                 230                 235                 240

Asn Val Glu Leu Glu Leu Lys Ala Glu Lys Asp Asn Ala Glu Ile Arg
                245                 250                 255

Val His Thr Val Glu Asp Tyr Gln Ala Ile Val Asp Ala Glu Trp Asn
            260                 265                 270

Ile Leu Tyr Asp Lys Leu Glu Lys Ile His His Ser Gly Ala Lys Val
        275                 280                 285

Val Leu Ser Lys Leu Pro Ile Gly Asp Val Ala Thr Gln Tyr Phe Ala
    290                 295                 300

Asp Arg Asp Met Phe Cys Ala Gly Arg Val Pro Glu Glu Asp Leu Lys
305                 310                 315                 320

Arg Thr Met Met Ala Cys Gly Gly Ser Ile Gln Thr Ser Val Asn Ala
                325                 330                 335

Leu Ser Ala Asp Val Leu Gly Arg Cys Gln Val Phe Glu Glu Thr Gln
            340                 345                 350

Ile Gly Gly Glu Arg Tyr Asn Phe Phe Thr Gly Cys Pro Lys Ala Lys
        355                 360                 365

Thr Cys Thr Phe Ile Leu Arg Gly Gly Ala Glu Gln Phe Met Glu Glu
    370                 375                 380

Thr Glu Arg Ser Leu His Asp Ala Ile Met Ile Val Arg Arg Ala Ile
385                 390                 395                 400

Lys Asn Asp Ser Val Val Ala Gly Gly Gly Ala Ile Glu Met Glu Leu
                405                 410                 415

Ser Lys Tyr Leu Arg Asp Tyr Ser Arg Thr Ile Pro Gly Lys Gln Gln
            420                 425                 430

Leu Leu Ile Gly Ala Tyr Ala Lys Ala Leu Glu Ile Ile Pro Arg Gln
        435                 440                 445

Leu Cys Asp Asn Ala Gly Phe Asp Ala Thr Asn Ile Leu Asn Lys Leu
    450                 455                 460

Arg Ala Arg His Ala Gln Gly Gly Thr Trp Tyr Gly Val Asp Ile Asn
465                 470                 475                 480

Asn Glu Asp Ile Ala Asp Asn Phe Glu Ala Phe Val Trp Glu Pro Ala
                485                 490                 495

Met Val Arg Ile Asn Ala Leu Thr Ala Ala Ser Glu Ala Ala Cys Leu
            500                 505                 510

Ile Val Ser Val Asp Glu Thr Ile Lys Asn Pro Arg Ser Thr Val Asp
        515                 520                 525

Ala Pro Thr Ala Ala Gly Arg Gly Arg Gly Arg Gly Arg Pro His
    530                 535                 540
```

-continued

<210> SEQ ID NO 19
<211> LENGTH: 377
<212> TYPE: PRT
<213> ORGANISM: Homo sapiens

<400> SEQUENCE: 19

```
Met Cys Glu Glu Glu Asp Ser Thr Ala Leu Val Cys Asp Asn Gly Ser
1               5                   10                  15

Gly Leu Cys Lys Ala Gly Phe Ala Gly Asp Asp Ala Pro Arg Ala Val
            20                  25                  30

Phe Pro Ser Ile Val Gly Arg Pro Arg His Gln Gly Val Met Val Gly
        35                  40                  45

Met Gly Gln Lys Asp Ser Tyr Val Gly Asp Glu Ala Gln Ser Lys Arg
    50                  55                  60

Gly Ile Leu Thr Leu Lys Tyr Pro Ile Glu His Gly Ile Ile Thr Asn
65                  70                  75                  80

Trp Asp Asp Met Glu Lys Ile Trp His His Ser Phe Tyr Asn Glu Leu
                85                  90                  95

Arg Val Ala Pro Glu Glu His Pro Thr Leu Leu Thr Glu Ala Pro Leu
            100                 105                 110

Asn Pro Lys Ala Asn Arg Glu Lys Met Thr Gln Ile Met Phe Glu Thr
        115                 120                 125

Phe Asn Val Pro Ala Met Tyr Val Ala Ile Gln Ala Val Leu Ser Leu
    130                 135                 140

Tyr Ala Ser Gly Arg Thr Thr Gly Ile Val Leu Asp Ser Gly Asp Gly
145                 150                 155                 160

Val Thr His Asn Val Pro Ile Tyr Glu Gly Tyr Ala Leu Pro His Ala
                165                 170                 175

Ile Met Arg Leu Asp Leu Ala Gly Arg Asp Leu Thr Asp Tyr Leu Met
            180                 185                 190

Lys Ile Leu Thr Glu Arg Gly Tyr Ser Phe Val Thr Thr Ala Glu Arg
        195                 200                 205

Glu Ile Val Arg Asp Ile Lys Glu Lys Leu Cys Tyr Val Ala Leu Asp
    210                 215                 220

Phe Glu Asn Glu Met Ala Thr Ala Ala Ser Ser Ser Ser Leu Glu Lys
225                 230                 235                 240

Ser Tyr Glu Leu Pro Asp Gly Gln Val Ile Thr Ile Gly Asn Glu Arg
                245                 250                 255

Phe Arg Cys Pro Glu Thr Leu Phe Gln Pro Ser Phe Ile Gly Met Glu
            260                 265                 270

Ser Ala Gly Ile His Glu Thr Thr Tyr Asn Ser Ile Met Lys Cys Asp
        275                 280                 285

Ile Asp Ile Arg Lys Asp Leu Tyr Ala Asn Asn Val Leu Ser Gly Gly
    290                 295                 300

Thr Thr Met Tyr Pro Gly Ile Ala Asp Arg Met Gln Lys Glu Ile Thr
305                 310                 315                 320

Ala Leu Ala Pro Ser Thr Met Lys Ile Lys Ile Ile Ala Pro Pro Glu
                325                 330                 335

Arg Lys Tyr Ser Val Trp Ile Gly Gly Ser Ile Leu Ala Ser Leu Ser
            340                 345                 350

Thr Phe Gln Gln Met Trp Ile Ser Lys Gln Glu Tyr Asp Glu Ala Gly
        355                 360                 365

Pro Ser Ile Val His Arg Lys Cys Phe
    370                 375
```

<210> SEQ ID NO 20
<211> LENGTH: 377
<212> TYPE: PRT
<213> ORGANISM: Homo sapiens

<400> SEQUENCE: 20

```
Met Cys Glu Glu Glu Asp Ser Thr Ala Leu Val Cys Asp Asn Gly Ser
1               5                   10                  15

Gly Leu Cys Lys Ala Gly Phe Ala Gly Asp Asp Ala Pro Arg Ala Val
            20                  25                  30

Phe Pro Ser Ile Val Gly Arg Pro Arg His Gln Gly Val Met Val Gly
        35                  40                  45

Met Gly Gln Lys Asp Ser Tyr Val Gly Asp Glu Ala Gln Ser Lys Arg
    50                  55                  60

Gly Ile Leu Thr Leu Lys Tyr Pro Ile Glu His Gly Ile Ile Thr Asn
65                  70                  75                  80

Trp Asp Asp Met Glu Lys Ile Trp His His Ser Phe Tyr Asn Glu Leu
                85                  90                  95

Arg Val Ala Pro Glu Glu His Pro Thr Leu Leu Thr Glu Ala Pro Leu
            100                 105                 110

Asn Pro Lys Ala Asn Arg Glu Lys Met Thr Gln Ile Met Phe Glu Thr
        115                 120                 125

Phe Asn Val Pro Ala Met Tyr Val Ala Ile Gln Ala Val Leu Ser Leu
    130                 135                 140

Tyr Ala Ser Gly Arg Thr Thr Gly Ile Val Leu Asp Ser Gly Asp Gly
145                 150                 155                 160

Val Thr His Asn Val Pro Ile Tyr Glu Gly Tyr Ala Leu Pro His Ala
                165                 170                 175

Ile Met Arg Leu Asp Leu Ala Gly Arg Asp Leu Thr Asp Tyr Leu Met
            180                 185                 190

Lys Ile Leu Thr Glu Arg Gly Tyr Ser Phe Val Thr Thr Ala Glu Arg
        195                 200                 205

Glu Ile Val Arg Asp Ile Lys Glu Lys Leu Cys Tyr Val Ala Leu Asp
    210                 215                 220

Phe Glu Asn Glu Met Ala Thr Ala Ala Ser Ser Ser Ser Leu Glu Lys
225                 230                 235                 240

Ser Tyr Glu Leu Pro Asp Gly Gln Val Ile Thr Ile Gly Asn Glu Arg
                245                 250                 255

Phe Arg Cys Pro Glu Thr Leu Phe Gln Pro Ser Phe Ile Gly Met Glu
            260                 265                 270

Ser Ala Gly Ile His Glu Thr Thr Tyr Asn Ser Ile Met Lys Cys Asp
        275                 280                 285

Ile Asp Ile Arg Lys Asp Leu Tyr Ala Asn Asn Val Leu Ser Gly Gly
    290                 295                 300

Thr Thr Met Tyr Pro Gly Ile Ala Asp Arg Met Gln Lys Glu Ile Thr
305                 310                 315                 320

Ala Leu Ala Pro Ser Thr Met Lys Ile Lys Ile Ile Ala Pro Pro Glu
                325                 330                 335

Arg Lys Tyr Ser Val Trp Ile Gly Gly Ser Ile Leu Ala Ser Leu Ser
            340                 345                 350

Thr Phe Gln Gln Met Trp Ile Ser Lys Gln Glu Tyr Asp Glu Ala Gly
        355                 360                 365

Pro Ser Ile Val His Arg Lys Cys Phe
    370                 375
```

<210> SEQ ID NO 21
<211> LENGTH: 1798
<212> TYPE: DNA
<213> ORGANISM: Homo sapiens

<400> SEQUENCE: 21
ctctccccgc ccccgcgggg cggcgcgcac tcacccaccc gcgccggagc ggacctttgg 60
cttggcttgt cagggcttgt ccaggagttc cgctcctctc tccaaccggg gtccccctcc 120
agcgacccta aagcttccca gacttccgct tcaattcctg tccgcacccc acgcccacct 180
caacgtggag cgcagtggtc tccgaggagc gccggagctg ccccgcctgc ccagcggggt 240
cagcacttcg catcaaggcc caagaaaagc aagtcctcca gcgttctgag cacccgggcc 300
tgagggaagg tcctaacagc cccggggagc cagtctccaa cgcctcccgc agcagcccgc 360
cgctcccagg tgcccgcgtg cgccgctgcc gccgcaatcc cgcacgcgtc ccgcgcccgc 420
cccactttgc ctatccccgg gactaagacg ggaatcctgt gaagcagctc cagctatgtg 480
tgaagaagag gacagcactg ccttggtgtg tgacaatggc tctgggctct gtaaggccgg 540
ctttgctggg gacgatgctc ccagggctgt tttcccatcc attgtgggac gtcccagaca 600 tcaggggggtg atggtgggaa tgggacaaaa agacagctac gtgggtgacg aagcacagag 660
caaaagagga atcctgaccc tgaagtaccc gatagaacat ggcatcatca ccaactggga 720
cgacatggaa aagatctggc accactcttt ctacaatgag cttcgtgttg cccctgaaga 780
gcatcccacc ctgctcacgg aggcacccct gaaccccaag gccaaccggg agaaaatgac 840
tcaaattatg tttgagactt tcaatgtccc agccatgtat gtggctatcc aggcggtgct 900
gtctctctat gcctctggac gcacaactgg catcgtgctg gactctggag atggtgtcac 960
ccacaatgtc cccatctatg agggctatgc cttgccccat gccatcatgc gtctggatct 1020
ggctggccga gatctcactg actacctcat gaagatcctg actgagcgtg gctattcctt 1080
cgttactact gctgagcgtg agattgtccg ggacatcaag gagaaactgt gttatgtagc 1140
tctggacttt gaaaatgaga tggccactgc cgcatcctca tcctcccttg agaagagtta 1200
cgagttgcct gatgggcaag tgatcaccat cggaaatgaa cgtttccgct gcccagagac 1260
cctgttccag ccatccttca tcgggatgga gtctgctggc atccatgaaa ccacctacaa 1320
cagcatcatg aagtgtgata ttgacatcag gaaggacctc tatgctaaca atgtcctatc 1380
agggggcacc actatgtacc ctggcattgc cgaccgaatg cagaaggaga tcacggccct 1440
agcacccagc accatgaaga tcaagatcat tgcccctccg gagcgcaaat actctgtctg 1500
gatcggtggc tccatcctgg cctctctgtc caccttccag cagatgtgga tcagcaaaca 1560
ggaatacgat gaagccgggc cttccattgt ccaccgcaaa tgcttctaaa acactttcct 1620
gctcctctct gtctctagca cacaactgtg aatgtcctgt ggaattatgc cttcagttct 1680
tttccaaatc attcctagcc aaagctctga ctcgttacct atgtgttttt taataaatct 1740
gaaataggct actggtaaaa aaaaaaaaaa aaaaaaaaaa aaaaaaaaaa aaaaaaaa 1798

<210> SEQ ID NO 22
<211> LENGTH: 1415
<212> TYPE: DNA
<213> ORGANISM: Homo sapiens

<400> SEQUENCE: 22
gaggagagca ggccaagggg ctatataacc cttcagcttt cagcttccct gaacaccacc 60

-continued

```
cagtgtggag cagcccagcc aagcactgtc aggaatcctg tgaagcagct ccagctatgt    120

gtgaagaaga ggacagcact gccttggtgt gtgacaatgg ctctgggctc tgtaaggccg    180

gctttgctgg ggacgatgct cccagggctg ttttcccatc cattgtggga cgtcccagac    240

atcagggggt gatggtggga atgggacaaa aagacagcta cgtgggtgac gaagcacaga    300

gcaaaagagg aatcctgacc ctgaagtacc cgatagaaca tggcatcatc accaactggg    360

acgacatgga aaagatctgg caccactctt tctacaatga gcttcgtgtt gcccctgaag    420

agcatcccac cctgctcacg gaggcacccc tgaaccccaa ggccaaccgg gagaaaatga    480

ctcaaattat gtttgagact ttcaatgtcc cagccatgta tgtggctatc caggcggtgc    540

tgtctctcta tgcctctgga cgcacaactg gcatcgtgct ggactctgga gatggtgtca    600

cccacaatgt ccccatctat gagggctatg ccttgcccca tgccatcatg cgtctggatc    660

tggctggccg agatctcact gactacctca tgaagatcct gactgagcgt ggctattcct    720

tcgttactac tgctgagcgt gagattgtcc gggacatcaa ggagaaactg tgttatgtag    780

ctctggactt tgaaaatgag atggccactg ccgcatcctc atcctccctt gagaagagtt    840

acgagttgcc tgatgggcaa gtgatcacca tcggaaatga acgtttccgc tgcccagaga    900

ccctgttcca gccatccttc atcgggatgg agtctgctgg catccatgaa accacctaca    960

acagcatcat gaagtgtgat attgacatca ggaaggacct ctatgctaac aatgtcctat   1020

caggggggcac cactatgtac cctggcattg ccgaccgaat gcagaaggag atcacggccc  1080

tagcacccag caccatgaag atcaagatca ttgcccctcc ggagcgcaaa tactctgtct   1140

ggatcggtgg ctccatcctg gcctctctgt ccaccttcca gcagatgtgg atcagcaaac   1200

aggaatacga tgaagccggg ccttccattg tccaccgcaa atgcttctaa aacactttcc   1260

tgctcctctc tgtctctagc acacaactgt gaatgtcctg tggaattatg ccttcagttc   1320

ttttccaaat cattcctagc caaagctctg actcgttacc tatgtgtttt ttaataaatc   1380

tgaaataggc tactggtaaa aaaaaaaaaa aaaaa                              1415
```

<210> SEQ ID NO 23
<211> LENGTH: 21
<212> TYPE: DNA
<213> ORGANISM: Artificial Sequence
<220> FEATURE:
<223> OTHER INFORMATION: Rabbit CCT-beta sense 5' to 3'

<400> SEQUENCE: 23

```
ggagaaaguu gaacguauut t                                               21
```

<210> SEQ ID NO 24
<211> LENGTH: 21
<212> TYPE: DNA
<213> ORGANISM: Artificial Sequence
<220> FEATURE:
<223> OTHER INFORMATION: Rabbit CCT-beta Antisense 5' to 3'

<400> SEQUENCE: 24

```
aauacguuca acuuucucct t                                               21
```

<210> SEQ ID NO 25
<211> LENGTH: 56
<212> TYPE: DNA
<213> ORGANISM: Artificial Sequence
<220> FEATURE:
<223> OTHER INFORMATION: mETA-1203siF DNA insert

<400> SEQUENCE: 25

-continued

```
gatccaagaa tgactctgtg gtggctttca agagaagcca ccacagagtc attctt        56


<210> SEQ ID NO 26
<211> LENGTH: 56
<212> TYPE: DNA
<213> ORGANISM: Artificial Sequence
<220> FEATURE:
<223> OTHER INFORMATION: mETA-1203siR DNA insert

<400> SEQUENCE: 26

agcttaagaa tgactctgtg gtggcttctc ttgaaagcca ccacagagtc attctt        56


<210> SEQ ID NO 27
<211> LENGTH: 55
<212> TYPE: DNA
<213> ORGANISM: Artificial Sequence
<220> FEATURE:
<223> OTHER INFORMATION: mEta-1205siF DNA insert

<400> SEQUENCE: 27

gatccgaatg actctgtggt ggctttcaag agaagccacc acagagtcat tctta         55


<210> SEQ ID NO 28
<211> LENGTH: 55
<212> TYPE: DNA
<213> ORGANISM: Artificial Sequence
<220> FEATURE:
<223> OTHER INFORMATION: mEta-1205siR DNA insert

<400> SEQUENCE: 28

agcttaagaa tgactctgtg gtggcttctc ttgaaagcca ccacagagtc attcg         55


<210> SEQ ID NO 29
<211> LENGTH: 66
<212> TYPE: DNA
<213> ORGANISM: Artificial Sequence
<220> FEATURE:
<223> OTHER INFORMATION: Luciferase siRNA DNA insert

<400> SEQUENCE: 29

ggatcctcgc ttaccgattc agaatggttg atatccgcca ttctgaatcg gtaagcgacg    60

aagctt                                                               66
```

COMPOSITION AND METHODS FOR REDUCED SCARRING AND TREATMENT OF FIBROSIS

CROSS-REFERENCE TO RELATED APPLICATIONS

This divisional application claims the benefit under 35 U.S.C. § 120 of U.S. application Ser. No. 13/643,975, filed on Jan. 14, 2013, entitled COMPOSITION AND METHODS FOR REDUCED SCARRING AND FOR TREATMENT OF FIBROSIS, which further claims the benefit of U.S. Provisional Application No. 61/328,957 entitled "Compositions and Methods for Reduced Scarring in Healing Wounds and for Treatment and Prevention of Fibrosis" filed Apr. 28, 2010, which is herein incorporated in its entirety.

STATEMENT PURSUANT TO 37 CFR 1.821(f)

The Sequence Listing information recorded in computer readable form and filed on Dec. 20, 2013 in association with the parent application, United States Patent and Trademark Office in U.S. application Ser. No. 13/643,975, filed on Jan. 14, 2013, is identical to the written sequence listing.

GOVERNMENT INTERESTS

This research was conducted with support from the U.S. government under grants from the Armed Forces Institute of Regenerative Medicine (contract number W81XWH-08-2-0032) and National Institute of Health (contract number 1K08DE014780). The U.S. government has certain rights in the invention.

SUMMARY

Embodiments of the present disclosure relate generally to methods of treating or preventing fibrosis or reducing scarring in healing wounds comprising administering a therapeutic molecular agent selected from the group consisting of an agent to inhibit expression and function of the mRNA for chaperonin containing T-complex polypeptide subunit eta polypeptide ("CCT-eta"), an agent to inhibit CCT-eta protein, an agent to inhibit expression and/or function of the α-Smooth Muscle Actin ("α-SMA") mRNA, an agent to inhibit the α-Smooth Muscle Actin protein and combinations thereof.

Embodiments of this invention relate to the regulation of gene expression by small interfering RNA ("siRNA"), in particular for reducing scarring in wounds. Embodiments of this invention relate to the regulation of gene expression by antisense oligonucleotides, in particular for reducing scarring in wounds. Further embodiments of this invention relate to the regulation of gene expression by ribozymes, in particular for reducing scarring in wounds. Embodiments of this invention relate to the regulation of proteins by antibodies, in particular for reducing scarring in wounds.

Embodiments of this invention relate to the regulation of gene expression by siRNA, in particular for treating or preventing fibrosis. Embodiments of this invention relate to the regulation of gene expression by antisense oligonucleotides, in particular for treating or preventing fibrosis. Further embodiments of this invention relate to the regulation of gene expression by ribozymes, in particular for treating or preventing fibrosis. Embodiments of this invention relate to the regulation of proteins by antibodies, in particular for treating or preventing fibrosis.

Embodiments of this invention relate to the regulation of gene expression by siRNA, in particular for treating or preventing Dupuytren's contracture. Embodiments of this invention relate to the regulation of gene expression by antisense oligonucleotides, in particular for treating or preventing Dupuytren's contracture. Further embodiments of this invention relate to the regulation of gene expression by ribozymes, in particular for treating or preventing Dupuytren's contracture. Embodiments of this invention relate to the regulation of proteins by antibodies, in particular for treating or preventing Dupuytren's contracture.

In one embodiment, a method of treating or preventing fibrosis or reducing scarring comprising administrating to a subject an effective amount of an siRNA targeted to inhibit expression of CCT-eta is provided.

In another embodiment, a method of treating or preventing fibrosis or reducing scarring comprising administrating to a subject an effective amount of an siRNA targeted to inhibit expression of α-SMA is provided.

In another embodiment, a method of treating or preventing fibrosis or reducing scarring comprising administrating to a subject an effective amount of a plasmid vector designed to produce siRNA targeted to inhibit expression of CCT-eta is provided.

In another embodiment, a method of treating or preventing fibrosis or reducing scarring comprising administrating to a subject an effective amount of a plasmid vector designed to produce siRNA targeted to inhibit expression of α-SMA is provided.

In another embodiment, a method of treating or preventing fibrosis or reducing scarring comprising administrating to a subject an effective amount of a viral vector designed to produce siRNA targeted to inhibit expression of CCT-eta is provided.

In another embodiment, a method of treating or preventing fibrosis or reducing scarring comprising administrating to a subject an effective amount of a viral vector designed to produce siRNA targeted to inhibit expression of α-SMA is provided.

In another embodiment, a method of treating or preventing fibrosis or reducing scarring comprising administrating to a subject an effective amount of an antisense oligonucleotide targeted to inhibit expression of CCT-eta is provided.

In another embodiment, a method of treating or preventing fibrosis or reducing scarring comprising administrating to a subject an effective amount an antisense oligonucleotide targeted to inhibit expression of α-SMA is provided.

In another embodiment, a method of treating or preventing fibrosis or reducing scarring comprising administrating to a subject an effective amount of a plasmid vector designed to produce antisense oligonucleotide targeted to inhibit expression of CCT-eta is provided.

In another embodiment, a method of treating or preventing fibrosis or reducing scarring comprising administrating to a subject an effective amount of a plasmid vector designed to produce antisense oligonucleotide targeted to inhibit expression of α-SMA is provided.

In another embodiment, a method of treating or preventing fibrosis or reducing scarring comprising administrating to a subject an effective amount of a viral vector designed to produce antisense oligonucleotide targeted to inhibit expression of CCT-eta is provided.

In another embodiment, a method of treating or preventing fibrosis or reducing scarring comprising administrating to a subject an effective amount of a viral vector designed to produce antisense oligonucleotide targeted to inhibit expression of α-SMA is provided.

In another embodiment, a method of treating or preventing fibrosis or reducing scarring comprising administrating to a subject an effective amount of a ribozyme targeted to inhibit expression of CCT-eta is provided.

In another embodiment, a method of treating or preventing fibrosis or reducing scarring comprising administrating to a subject an effective amount a ribozyme targeted to inhibit expression of α-SMA is provided.

In another embodiment, a method of treating or preventing fibrosis or reducing scarring comprising administrating to a subject an effective amount of a plasmid vector designed to produce a ribozyme targeted to inhibit expression of CCT-eta is provided.

In another embodiment, a method of treating or preventing fibrosis or reducing scarring comprising administrating to a subject an effective amount of a plasmid vector designed to produce a ribozyme targeted to inhibit expression of α-SMA is provided.

In another embodiment, a method of treating or preventing fibrosis or reducing scarring comprising administrating to a subject an effective amount of a viral vector designed to produce a ribozyme targeted to inhibit expression of CCT-eta is provided.

In another embodiment, a method of treating or preventing fibrosis or reducing scarring comprising administrating to a subject an effective amount of a viral vector designed to produce a ribozyme targeted to inhibit expression of α-SMA is provided.

In another embodiment, a method of treating or preventing fibrosis or reducing scarring comprising administrating to a subject an effective amount of an antibody targeted to inhibition of CCT-eta is provided.

In another embodiment, a method of treating or preventing fibrosis or reducing scarring comprising administrating to a subject an effective amount of an antibody targeted to inhibition of α-SMA is provided.

These and other features provided by the present disclosure are set forth herein.

DESCRIPTION OF DRAWINGS

For a fuller understanding of the nature and advantages of the present disclosure, reference should be had to the following detailed description taken in connection with the accompanying drawings, in which.

DETAILED DESCRIPTION

Figure 1:
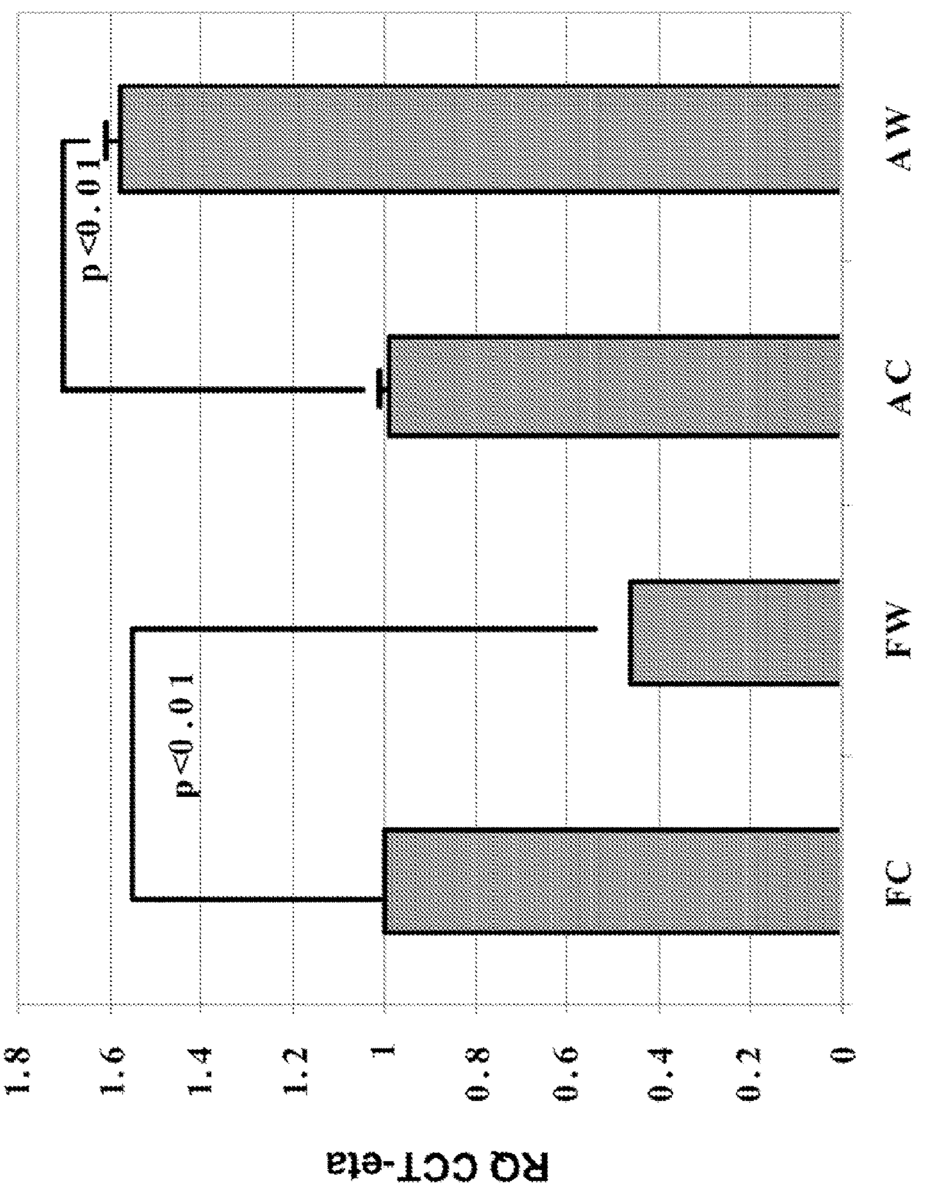
FIG. 1 illustrates qRT-PCR measurement of CCT-eta mRNA abundance in healing fetal and adult wounds.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present disclosure which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "molecular agent" is a reference to one or more molecular agents and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a molecular agent, can include, but is not limited to, providing a molecular agent into or onto the target tissue; providing an a molecular agent systemically to a patient by, e.g., intravenous injection whereby the therapeutic reaches the target tissue; or providing a molecular agent in the form of the encoding sequence thereof to the target tissue (e.g., by so-called gene-therapy techniques).

The term "animal," "patient," or "subject," as used herein, includes, but is not limited to, humans and non-human vertebrates such as wild, domestic and farm animals. In some embodiments, the term refers to humans and other higher animals and laboratory models, such as, for example, mice and rats. In some embodiments, the term refers to humans.

As used herein, an "effective amount" of the molecular agent is an amount sufficient to either cause degradation or neutralization of the target mRNA in a cell or cause degradation or neutralization of the target protein. The term clinically effective amount is an amount that when administered to a subject, will inhibit, decrease or prevent scarring in a subject.

The term "improves" is used to convey that the present disclosure changes either the appearance, form, characteristics and/or the physical attributes of the tissue to which it is being provided, applied or administered. The change in form may be demonstrated by any of the following alone or in combination: enhanced appearance of the skin; decreased scarring of the skin; decreased scar contraction; increased softness of the skin; decreased puckering of the skin; or, increased firmness and resiliency of the skin.

The term "inhibiting" includes the administration of a molecular agent of the present disclosure to treat or prevent the expression of the target mRNA or target nucleic acid.

As used herein, "target mRNA" means an mRNA comprising a complementary sense sequence to an siRNA antisense strand. Target mRNA can be non-human animal or human mRNA. Preferably, the target mRNA is human. Such a target mRNA need not be 100% homologous to the siRNA antisense strand, as long as the siRNA functions to silence or otherwise form a RISC complex with the target mRNA. For example, in certain embodiments, the siRNA sense strand may differ from the target mRNA by one to five nucleotides, from one to four nucleotides, from one to three nucleotides, from one to two nucleotides or one, two, three, four or five nucleotides. Target mRNAs of particular use in the methods of the disclosure include, for example, CCT-eta, α-SMA and combinations thereof. For example, target mRNAs of use in the methods include mRNAs of SEQ ID Nos. 7, 8, 11, 12, 13, 14, 21 and 22.

The term "molecular agent" may include, for example and without limitation, siRNAs, ribozymes, antisense oligonucleotides and antibodies.

The term "nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (such as deoxyribonucleotides and ribonucleotides), or analogs of naturally-occurring nucleotides (e.g., α-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

Embodiments of the invention also comprise administration of pharmaceutical compositions (or "medicaments"). These compositions may comprise any of the above described molecular agents, particularly siRNAs, ribozymes, antisense oligonucleotides, DNA molecules, antibodies, vectors or host cells, along with a pharmaceutically or physiologically acceptable carrier, excipient, or, diluent.

By "pharmaceutically acceptable", it is meant the carrier, diluent or excipient must be compatible with the other ingredients of the formulation and not deleterious to the recipient thereof.

Unless otherwise indicated, the term "skin" means that outer integument or covering of the body, consisting of the dermis and the epidermis and resting upon subcutaneous tissue.

Generally speaking, the term "vector" refers to an assembly which is capable of expressing the ribozyme, antisense oligonucleotide or siRNA of interest. The vector may be composed of either deoxyribonucleic acids ("DNA") or ribonucleic acids ("RNA"). Optionally, the vector may include a polyadenylation sequence, one or more restriction sites, as well as one or more selectable markers such as neomycin phosphotransferase, hygromycin phosphotransferase or puromycin-N-acetyl-transferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, prevention of scar or cicatrix formation; diminishment of the scar or cicatrix formed; stabilization (i.e., not worsening) of scar or cicatrix formation; delay in onset or slowing of the progression of the scar or cicatrix; amelioration of the scar or cicatrix; and enhancement or improvement of the scar or cicatrix. Treatment includes eliciting a clinically significant response without excessive levels of side effects.

For example, in some aspects, the invention is directed to a pharmaceutical composition comprising a molecular agent, as defined above, and a pharmaceutically acceptable carrier or diluent, or an effective amount of a pharmaceutical composition comprising a molecular agent as defined above.

Adult mammalian tissues respond to injury by healing with scar formation; in contrast, mammalian fetuses demonstrate an ability to heal without scar, a process that has been likened to regeneration. Although scar formation allows for the rapid sealing of an injured area, the resulting cicatrix can frequently prove the source of persistent pathology in the organism, eg. restricting movement, narrowing viscera etc. At the phenotypic level adult and fetal wound healing differ in multiple important respects: adult wound healing is marked by a prominent initial acute inflammatory response, which is absent in fetal wound healing, and fetal wound healing displays no accumulation of intermediary granulation tissue as found in healing adult wounds. Additionally, healing adult wounds are characterized by a marked contraction of the wound substance, thought to be mediated by tissue fibroblasts (and their cellular derivatives, myofibroblasts), whereas in fetal wounds no such contraction occurs. Fibroblasts/myofibroblasts may effect wound contraction either by acting together as a contractile unit, or more likely by acting individually to apply traction to a wound in the process of cell locomotion.

Scarring may be a significant source of disfigurement, pain, and increased medical costs for affected patients. There exist numerous conditions of fibrosis and scar contracture in which embodiments of the present disclosure may prove useful, of which skin wound healing is only the most apparent application. For example, a scar forms after abdominal surgery in the viscera, after tendon injury, in the joints and muscles, after eardrum injury, after corneal (eye) injury, in Dupuytren contracture and Peyronie's disease, etc.

Dupuytren's contracture is a fixed flexion contracture of the hand where the fingers bend towards the palm and cannot be fully extended (straightened). Dupuytren's contracture is caused by underlying contractures of the palmar fascia. The ring finger and little finger are the fingers most commonly affected. The middle finger may be affected in advanced cases, but the index finger and the thumb are nearly always spared. Dupuytren's contracture progresses slowly and is usually painless. In patients with this condition, the tissues under the skin on the palm of the hand thicken and shorten so that the tendons connected to the fingers cannot move freely. The palmar aponeurosis becomes hyperplastic and undergoes contracture.

In surgery, scar tissue formation and contraction is a major clinical problem. Likewise, scarring following accidental burning or other injuries or trauma often has serious results, causing impaired function and unsightly aesthetic effects. Currently, there are no satisfactory treatments to prevent scarring. Accordingly, there is a need for an effective treatment to reduce or prevent scarring or fibrosis. Additionally, there is a need for a method of treating diseases characterized by scarring or fibrosis, such as Dupuytren's contracture, Peyronie's disease, pulmonary fibrosis, cirrhosis, interstitial lung disease and scarring alopecia.

Some embodiments of the present disclosure may be directed to the reduction or prevention of scarring. Some embodiments of the present disclosure may be directed to treatment or prevention of fibrosis. Fibrosis is the formation or development of excess fibrous connective tissue in an organ or tissue as a reparative or reactive process, as opposed to a formation of fibrous tissue as a normal constituent of an organ or tissue. Fibrosis may occur due to injury, treatment and/or disease. Scarring is confluent fibrosis that obliterates the architecture of the underlying organ or tissue.

Without wishing to be bound by theory, it is believed that CCT-eta (SEQ ID Nos. 9 and 15-18), the eta subunit of chaperonin containing T-complex polypeptide, may be elevated during adult (scirrhous) wound healing but is downregulated in healing fetal wound milieu. The CCT molecule is the major cytosolic chaperonin in eukaryotes and has been estimated to interact with up to 15% of all cellular proteins. The structure of the CCT holoenzyme is unique among chaperonins; it includes two rings each comprised of eight discrete subunits: alpha, beta, gamma, delta, epsilon, eta, theta, and zeta (zeta 2, a variant of zeta, is highly expressed only in testis). The eight polypeptide subunits are encoded by eight different genes. The molecular weight of the complete assemblage is approximately 900 kD, but there is evidence that subunits may also localize and function separately as monomers or oligomers.

The primary substrates for CCT appear to be the cytoskeletal proteins (eg. tubulin and actin), but the CCT complex is estimated to interact with up to 15% of all cellular proteins and has been implicated in a variety of processes including embyrogenesis, ciliary biogenesis, cell viability and cell proliferation. Alterations in CCT components, therefore, have the potential to cause pleiotropic effects on cellular physiology. Without wishing to be bound by theory, it is believed that fibroblasts from fetal skin tissues express substantially less CCT-eta mRNA than do fibroblasts from adult skin.

CCT-eta is also an inhibitory co-factor for the soluble guanylyl cyclase (sGC), the co-factor for the soluble guanylyl cyclase (sGC), the chief intracellular mediator of nitric oxide (NO) signaling. Without being bound by theory, since CCT-eta is elevated in healing adult wounds, it may be supposed that sGC activity may be therefore suppressed, suggesting an inhibition of nitric oxide signaling in wound milieu in toto. Since arginine (and other agents that stimulate nitric oxide signaling pathways) have been shown to have favorable effects on wound healing, the increase in CCT-eta may contribute to the scirrhous nature of adult wound healing by inhibiting nitrous oxide-mediated effects.

Cellular actin, the major cytoskeletal element in cellular locomotion and traction, may be a major substrate of the CCT holoenzyme. Fibroblasts express two actin isoforms (namely β- and γ-actin), which are similarly expressed in all eukaryotic cell types. However, under certain conditions, fibroblasts may also express the alpha-smooth muscle isoform of actin (α-SMA), for example, when stimulated by serum in tissue culture or when stimulated during adult wound healing in vivo to function as "myofibroblasts," the derivative cell type most closely associated with wound contraction and scar formation. The presence of α-SMA has also been found to closely correlate with the appearance of scar formation even in fetal tissues that have already transitioned to the adult scar-forming phenotype in late gestation. It is believed that α-SMA mRNA and protein levels are persistently elevated in healing adult wounds, whereas α-SMA is largely absent from earlier scarlessly healing fetal wounds.

Without being bound by theory, it is believed that CCT-eta (SEQ ID Nos. 9 and 15-18) modulates the expression of α-SMA (SEQ ID No. 10 and 19-20), which is required for initiating and maintaining scar contraction. Targeting CCT-eta expression (and α-SMA expression as a consequence or directly) may inhibit the ability of fibroblast and myofibroblast cells, the chief effectors of cell formation, and may actively contract the wound substance, leading to less scar contracture. Accordingly, there is a need for a method of reducing scarring or fibrosis through the use of agents which selectively inhibit expression of CCT-eta or α-SMA.

Alpha smooth muscle actin (α-SMA), is a 42 kDa, 375 amino acids long protein coded by the ACTA2 gene (Gene map locus 10q22-q24) that is post-translationally modified (PTM) by N-terminal acetylation, methylation (tele-His75) and tyrosine nitration (Tyr296). α-SMA is a marker for the transformation of fibroblasts to myofibroblasts in a healing wound, with myofibroblasts thought to be the principal effector agents behind the contractile forces of a scar. Thus, increased CCT-eta may permit increased myofibroblast development and thereby increased scar contracture; α-SMA protein levels more or less track CCT-eta accumulation. Conversely the reduction of CCT-eta seen in healing fetal wounds may inhibit scar development by preventing fibroblastic transformation to myofibroblasts.

Myofibroblasts are terminally differentiated cells derived from fibroblasts, dedifferentiated smooth muscle cells (SMC) and possibly germ line transitions that play an important role in tissue fibrosis and epithelial cancer malignancies. α-SMA positive myofibroblasts have been found in the stroma of Dupuytren's nodule and a wide variety of carcinomas. The presence of α-SMA positive myofibroblasts is generally correlates with increased aggressiveness of the carcinoma and poor prognosis. α-SMA positive myofibroblasts are found in the stoma of non-malignant tissues during wound repair. Dysregulation of α-SMA positive myofibroblasts is linked to a wide variety of fibrotic diseases including atherosclerosis. α-SMA is expressed in a variety of myogenic soft tissue tumors, including leiomyomas, leiomyosarcomas and some rhabdomyosarcomas.

Fetal fibroblasts may express less constitutive α-SMA than adult cells, and reduction of CCT-eta may markedly diminish α-SMA protein levels, whereas reduction of CCT-beta may not have such effect. Direct reduction of α-SMA may lead to a similar decrease in both basal and growth-factor induced motility as seen with CCT-eta depletion, and may cause adult fibroblasts to mimic a more fetal pattern of behavior.

Compositions and methods comprising molecular agents targeted to CCT-eta mRNA and protein, and α-SMA mRNA and protein can be used to treat or prevent scarring in healing wounds or fibrosis. The molecular agent may cause the degradation or suppression of these mRNAs and proteins, so that CCT-eta and/or α-SMA is not produced or is produced in reduced amounts.

Thus, embodiments of the present disclosure are directed to methods of reducing scarring comprising administering a therapeutic molecular agent selected from an agent that inhibits chaperonin containing T-complex polypeptide subunit eta ("CCT-eta"), an agent that inhibits α-Smooth Muscle Actin ("α-SMA"), or a combination thereof. In some embodiments, scarring may include fibrosis. In some embodiments, the method of reducing scarring may comprise reducing scarring in wounds, preventing scar or cicatrix formation; diminishing any scar or cicatrix formed; stabilizing (i.e., not worsening) scar or cicatrix formation; delaying onset or slowing of the progression of the scar or cicatrix; ameliorating the scar or cicatrix; enhancing or improving the scar or cicatrix, reducing stiffness of scar or cicatrix, reducing fibrosis, treating fibrosis, or preventing fibrosis. In some embodiments, the method of reducing scarring may comprise reducing scarring, treating scarring, preventing scarring, reducing fibrosis, treating fibrosis, or preventing fibrosis. In some embodiments, the agent that inhibits CCT-eta may be selected from an agent that inhibits expression of CCT-eta mRNA, an agent that inhibits CCT-eta protein, or a combination thereof. In some embodiments, the agent that inhibits α-SMA may be selected from an agent that inhibits expression of α-SMA mRNA, an agent that inhibits α-SMA protein, or a combination thereof.

In some embodiments, the molecular agent may be selected from siRNA, ribozyme, antisense oligonucleotides, an antibody, or a combination thereof. In some embodiments, the agent that inhibits CCT-eta mRNA expression may be selected from siRNA, ribozymes, antisense oligonucleotides or a combination thereof. In some embodiments, the agent that inhibits α-SMA mRNA expression may be selected from siRNA, ribozymes, antisense oligonucleotides or a combination thereof. In some embodiments, the siRNA may comprise a sense strand and an antisense strand. In some embodiments, the sense strand may comprise SEQ ID No. 1 (for inhibition of CCT-eta mRNA) or 5 (for inhibition of α-SMA mRNA). In some embodiments, the antisense strand may comprise SEQ ID No. 2 (for inhibition of CCT-eta mRNA) or 6 (for inhibition of α-SMA mRNA). In some embodiments, the agent that inhibits CCT-eta mRNA comprises an siRNA comprising a sense strand comprising SEQ ID No. 1 or a variant thereof and an antisense strand comprising SEQ ID No. 2 or a variant thereof. In some embodiments, the agent that inhibits α-SMA mRNA comprises an siRNA comprising a sense strand comprising SEQ ID No. 5 or a variant thereof and an antisense strand comprising SEQ ID No. 6 or a variant thereof.

Variants of such molecular agents may be made by accommodating variations in sequences of different species (e.g. human mRNA or protein) and different target sequences within CCT-eta mRNA or alpha-SMA mRNA. Such techniques are within the skill of one in the art. As used herein, "variants" include sequences that have a homology to the disclosed sequence of from about 50% to about 99.9%, about 50% to about 99%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 99.9%, about 60% to about 99%, about 60% to about 95%, about 60% to about 90%, about 60% to about 85%, about 60% to about 80%, about 60% to about 75%, about 60% to about 70%, about 60% to about 65%, about 70% to about 99.9%, about 70% to about 99%, about 70% to about 95%, about 70% to about 90%, about 70% to about 85%, about 70% to about 80%, about 70% to about 75%, at least about 60%, at least about 70%, at least about 80%, at least about 85%, at least about 90%, at least about 95%, at least about 99% or ranges between any two of these values. For example, in some embodiments, a variant of a sense strand of an siRNA against CCT-eta may comprise variants with at least about 70%, about 80%, about 85%, about 90%, about 95%, or about 99% homology to SEQ ID No. 1. Likewise, in some embodiments, a variant of a antisense strand of an siRNA against CCT-eta may comprise variants with at least about 70%, about 80%, about 85%, about 90%, about 95%, or about 99% homology to SEQ ID No. 2.

As another example, in some embodiments, a variant of a sense strand of an siRNA against α-SMA may comprise variants with at least about 70%, about 80%, about 85%, about 90%, about 95%, or about 99% homology to SEQ ID No. 5. Likewise, in some embodiments, a variant of a antisense strand of an siRNA against α-SMA may comprise variants with at least about 70%, about 80%, about 85%, about 90%, about 95%, or about 99% homology to SEQ ID No. 6. As used herein, "homology" means the extent of sequence correlation between two sequences.

In some embodiments, the siRNA may be encoded within a vector. In some embodiments, the vector may be selected from a plasmid vector or a viral vector.

In some embodiments, the agent that inhibits CCT-eta mRNA comprises an siRNA that inhibits a target mRNA selected from SEQ ID No. 8, 11, 12, 13, 14, a variant thereof or a combination thereof. In some embodiments, the agent that inhibits CCT-eta mRNA comprises an siRNA that inhibits a target mRNA selected from SEQ ID No. 11, 12, 13, 14 or a combination thereof. In some embodiments, the agent that inhibits α-SMA mRNA comprises an siRNA that inhibits a target mRNA selected from SEQ ID No. 9, 21, 22, a variant thereof or a combination thereof. In some embodiments, the agent that inhibits α-SMA mRNA comprises an siRNA that inhibits a target mRNA selected from SEQ ID No. 21, 22, a variant thereof or a combination thereof.

In some embodiments, the agent that inhibits CCT-eta protein may be an antibody. In some embodiments, the antibody inhibits CCT-eta protein comprising SEQ ID No. 9, 15, 16, 17, 18, a variant thereof or a combination thereof. In some embodiments, the agent that inhibits α-SMA protein may be an antibody. In some embodiments, the antibody inhibits α-SMA protein comprising SEQ ID No. 10, 19, 20, a variant thereof or a combination thereof. In some embodiments, the antibody may be a monoclonal antibody or a polyclonal antibody.

Embodiments of the present disclosure are directed to methods of reducing scarring in healing wounds comprising administering a therapeutic molecular agent selected from the group consisting of an agent that inhibits expression of CCT-eta mRNA, an agent that inhibits CCT-eta protein, an agent to inhibit expression of α-SMA mRNA, and an agent to inhibit α-SMA protein.

Particular embodiments of this invention provide for the siRNA-mediated degradation of CCT-eta mRNA and/or α-SMA mRNA to inhibit the scarring process. Furthermore, embodiments of this invention provide for inhibition of CCT-eta mRNA and/or α-SMA mRNA using antisense oligonucleotides or ribozymes. Embodiments of the present disclosure also relate to antibodies directed to the CCT-eta and α-SMA proteins. Any location or circumstance in the body where scar or fibrosis occurs and causes pathology is potentially amenable to intervention targeting these gene products using siRNA or antisense or ribozyme or antibody technology.

In one embodiment, the siRNA comprises a sense RNA strand and a complementary antisense RNA strand annealed together by standard Watson-Crick base-pairing interactions (hereinafter "base-paired"). The sense strand may comprise a nucleic acid sequence which is identical or closely homologous to a target sequence contained within the target mRNA. In some embodiments, the sense and antisense strands of the siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form an siRNA of two individual base-paired RNA molecules.

Examples of sense strand encompassed by this invention include SEQ ID Nos. 1, 3, 5, a variant thereof or a combination thereof. Furthermore, variants of siRNA sense strand may include a nucleic acid sequence which is identical or closely homologous to any target sequence contained within the target mRNA. Though, particular sequences have been disclosed, methods of making variants of siRNA against target mRNA from a different species (e.g. human) or a different target sequence within the target mRNA are within the skill of one in the art. Examples of anti-sense strand encompassed by this invention include SEQ ID Nos. 2, 4 and 6. In some embodiments, the agent that inhibits CCT-eta or the agent that inhibits α-SMA may be an siRNA directed to target mRNA from a human. In some embodiments, the target mRNA may be selected from SEQ ID Nos. 7, 8, 11-14, 21-22, a variant thereof or a combination thereof. In some embodiments, the target mRNA may be selected from SEQ ID Nos. 7, 8, a variant thereof or a combination thereof. In some embodiments, the target mRNA may be selected from SEQ ID Nos. 11-14, 21-22, a variant thereof or a combination thereof.

RNA interference ("RNAi") is a method of post-transcriptional gene regulation that is conserved throughout many eukaryotic organisms. RNAi is induced by short (i.e., <30 nucleotide) double stranded RNA ("dsRNA") molecules which are present in the cell. These short dsRNA molecules, called "short interfering RNA" or "siRNA," cause the destruction of messenger RNA ("mRNA") which share sequence homology with the siRNA to within one nucleotide resolution. It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

One skilled in the art can readily determine an effective amount of the siRNA to be administered to a given subject, by taking into account factors such as the size and weight of the subject; the extent of the wound repair or disease penetration; the age, health and sex of the subject; the route of administration; and whether the administration is regional or systemic. Generally, an effective amount of the siRNA comprises an intercellular concentration at or near the wound repair site of from about 1 nanomolar (nM) to about 100 nM, preferably from about 2 nM to about 50 nM, more preferably from about 2.5 nM to about 10 nM. It is contemplated that greater or lesser amounts of siRNA can be administered.

Thus, an embodiment of this invention is directed to siRNAs which specifically target and cause RNAi-induced degradation of mRNA encoding CCT-eta or α-SMA. The siRNA compounds and compositions of the disclosure may be used to treat or prevent fibrosis or reduce scarring in wounds.

Embodiments of this invention also provide recombinant plasmids and viral vectors which express the siRNA disclosed herein, as well as pharmaceutical compositions comprising such an siRNA and a pharmaceutically acceptable carrier.

Selection of plasmids suitable for expressing siRNA, methods for inserting nucleic acid sequences for expressing the siRNA into the plasmid, and methods of delivering the recombinant plasmid to the cells of interest are within the skill in the art. See, for example Tuschl, T. (2002), *Nat. Biotechnol,* 20: 446-448; Brummelkamp T R et al. (2002), *Science* 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat. Biotechnol. 20: 505-508, the entire disclosures of which are herein incorporated by reference.

In some embodiments, the siRNA may be expressed from recombinant viral vectors intracellularly at or near the area of fibrosis or wound repair in vivo. The recombinant viral vectors of the invention comprise sequences encoding the siRNA and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. The use of recombinant viral vectors to deliver siRNA to cells in vivo is discussed in more detail below.

In some embodiments, siRNA may be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g. lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, methods for inserting nucleic acid sequences for expressing the siRNA into the vector, and methods of delivering the viral vector to the cells of interest are within the skill in the art. See, for example, Dornburg R (1995), *Gene Therap.* 2: 301-310; Eglitis M A (1988), *Biotechniques* 6: 608-614; Miller A D (1990), *Hum Gene Therap.* 1: 5-14; and Anderson W F (1998), *Nature* 392: 25-30, the entire disclosures of which are herein incorporated by reference.

Additionally, embodiments of the invention also contemplate a method of reducing scarring in wounds comprising administering to a subject an effective amount of a cocktail of siRNA targeted to both CCT-eta mRNA and α-SMA mRNA.

In some embodiments, administering siRNA targeted to CCT-eta mRNA may decrease hydroxyproline content of wounds. In some embodiments, administering siRNA targeted to CCT-eta mRNA may decrease α-SMA protein levels in wounds. In some embodiments, administering siRNA targeted to CCT-eta mRNA may decrease α-SMA mRNA levels.

In some embodiments, administering siRNA targeted to CCT-eta mRNA may decrease collagen content in wounds. In some embodiments, administering siRNA targeted to CCT-eta mRNA may normalize collagen content in wounds. In some embodiments, administering siRNA targeted to CCT-eta mRNA may decrease collagen content to about 60% to about 120%, about 60% to about 100%, about 60% to about 90%, about 60% to about 80%, about 70% to about 120%, about 70% to about 100%, about 70% to about 90%, about 70% to about 80%, about 80%, about 90%, or about 100% of unwounded skin.

In some embodiments, administering siRNA targeted to CCT-eta mRNA may increase tensile strength in wounds. In some embodiments, the administering siRNA targeted to CCT-eta mRNA may cause an increased re-accumulation of tensile strength compared to untreated wounds. In some embodiments, the wound may re-accumulate from about 30% to about 100% of the tensile strength of unwounded skin. In some embodiments, the wound may re-accumulate from about 30% to about 95%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, or about 30% to about 45% of the tensile strength of unwounded skin.

In some embodiments, administering siRNA targeted to α-SMA mRNA may increase tensile strength in wounds. In some embodiments, the administering siRNA targeted to α-SMA mRNA may cause an increased re-accumulation of tensile strength compared to untreated wounds. In some embodiments, the wound may re-accumulate from about 30% to about 100% of the tensile strength of unwounded skin. In some embodiments, the wound may re-accumulate from about 30% to about 95%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, or about 30% to about 45% of the tensile strength of unwounded skin.

Certain embodiments of the present disclosure are directed to a method of treating a disease characterized by scarring or fibrosis, such as, without limitation, Dupuytren's contracture, Peyronie's disease, pulmonary fibrosis, cirrhosis, interstitial lung disease or scarring alopecia comprising administering to a subject an effective amount of a therapeutic molecular agent selected from an agent that inhibits CCT-eta and an agent that inhibits α-SMA. In some embodiments, the therapeutic molecular agent may comprise an agent to inhibit expression and function of the CCT-eta mRNA, an agent to suppress CCT-eta protein, an agent to inhibit expression and function of the α-SMA mRNA, and an agent to suppress the α-SMA protein. Certain embodiments of the present disclosure are related to treatment or prevention of Dupuytren's contracture. Certain embodiments of the present disclosure are related to treatment or prevention of Peyronie's disease.

Embodiments of the present disclosure provide antisense oligonucleotides to prevent protein translation of CCT-eta or α-SMA mRNA strands. Antisense oligonucleotides are single-stranded RNA or DNA that are complementary to a mRNA strand transcribed within a cell. Antisense RNA/DNA may be introduced into a cell to inhibit translation of a complementary mRNA by base pairing to it and physically obstructing the translation machinery. In some embodiments, the antisense oligonucleotides may be complementary to target mRNA selected from SEQ ID Nos. 7, 8, 11, 12, 13, 14, 21, 22 or a combination thereof.

Embodiments of the present disclosure also provide a method of reducing scarring comprising administering to a subject an effective amount of a nucleic acid molecule, such as recombinant plasmids or viral vectors, which encode the antisense oligonucleotides disclosed herein, as well as pharmaceutical compositions comprising such antisense oligonucleotides and a pharmaceutically acceptable carrier.

Additionally, embodiments of the invention also contemplate a method of treating or preventing scarring in wounds comprising administering to a subject an effective amount of a cocktail of antisense oligonucleotides targeted to both CCT-eta mRNA (SEQ ID Nos. 7 and 11-14) and α-SMA mRNA (SEQ ID Nos. 8 and 21-22).

Embodiments of the present disclosure provide methods for treating or preventing scarring comprising the step of administering to a patient a therapeutically effective amount of ribozyme which cleaves RNA encoding CCT-eta or α-SMA. "Ribozyme" refers to a nucleic acid molecule which is capable of cleaving a specific nucleic acid sequence. Ribozymes may be composed of RNA, DNA, nucleic acid analogues (e.g., phosphorothioates), or any combination of these (e.g., DNA/RNA chimerics). Within particularly preferred embodiments, a ribozyme should be understood to refer to RNA molecules that contain antisense sequences for specific recognition, and an RNA-cleaving enzymatic activity. Ribozymes bind substrate RNAs through base-pairing interactions, cleave the bound target RNA, release the cleavage products, and are recycled so that they can repeat this process multiple times.

In certain embodiments, nucleic acid molecules encode the ribozymes provided herein. In some embodiments, the nucleic acid molecule may include a vector selected from a plasmid, a virus, retrotransposon, a cosmid, an adenovirus or a retrovirus.

In embodiments, the siRNA can be administered to the subject either as naked siRNA, in conjunction with a delivery reagent, or as a recombinant plasmid or viral vector which expresses the siRNA.

In certain embodiments, nucleic acid sequences for CCT-eta and α-SMA can be employed to design siRNA or antisense oligonucleotides that systematically "walk" down the sequence of interest. Though present disclosure does not specifically list all such possible sequences, they are within the scope of this invention. Methods for preparing such siRNA and antisense oligonucleotides of the invention are within the skill in the art.

Suitable delivery reagents for administration in conjunction with the present siRNA include the Mirus Transit TKO lipophilic reagent; atelocollagen; lipofectin; lipofectamine; cellfectin; or polycations (e.g., polylysine), or liposomes.

Liposomes can aid in the delivery of the siRNA to a particular tissue, such as retinal or tumor tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), Ann. Rev. Biophys. Bioeng. 9: 467; and U.S. Pat. Nos. 4,235,871, 4,501,728, 4,837,028, and 5,019,369, the entire disclosures of which are herein incorporated by reference.

Particularly preferably, the liposomes encapsulating the present siRNA are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

In some embodiments, the delivery agent may include atelocollagen. Atelocollagen is a form of highly purified calf dermal collagen subjected to pepsin digestion that is safe for a wide range of applications, including even some clinical (chiefly cosmetic) applications in humans.

In some embodiments, the delivery agent may be a gel-based formulation including siRNA-lipofectamine nanoparticulate complexes embedded in an agarose matrix.

In some embodiments, the delivery agent may be a calcium-phosphate based nanoparticle. Calcium-phosphate based nanoparticles may be formulated in a gel/salve consistency. Without wishing to be bound by theory, it is believed that a gel/salve consistency may render them ideal as a means of non-viral delivery of molecular agents (such as siRNAs) to a wound bed.

Recombinant plasmids which express siRNA are discussed above. In some embodiments, such recombinant plasmids may be administered directly or in conjunction with a suitable delivery reagent, including the Mirus Transit LT1 lipophilic reagent; lipofectin; lipofectamine; cellfectin; polycations (e.g., polylysine) or liposomes. Recombinant viral vectors which express siRNA are also discussed above, and methods for delivering such vectors to an area of fibrosis or wound repair in a patient are within the skill in the art.

The molecular agent may be administered to the subject by any means suitable for delivering the molecular agent to the cells of the tissue at or near the area of fibrosis or wound repair. For example, the molecular agents may be administered by gene gun, electroporation, or by other suitable parenteral, topical or enteral administration routes. In certain embodiments, injections or topical administrations of the molecular agent are given at or near the site of fibrosis or wound repair. In other embodiments, the molecular agent is administered intravenously.

Pharmaceutical formulations containing the molecular agent of the present invention and a suitable carrier may be solid dosage forms which include, but are not limited to, tablets, capsules, cachets, pellets, pills, powders and granules; and parenteral dosage forms which include, but are not limited to, solutions, suspensions, emulsions, and dry powder; comprising an effective amount of a molecular agent of the present invention.

In some embodiments, the molecular agent may be administered through topical administration. In some embodiments, topical dosage forms which include, but are not limited to, solutions, powders, fluid emulsions, fluid suspensions, semi-solids, ointments, pastes, creams, gels and jellies, and foams. In some embodiments, the molecular agents may be in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The molecular agent may be administered in a single dose or in multiple doses. Where the administration of the molecular agent is by infusion, the infusion can be a single sustained dose or can be delivered by multiple infusions. Injection of the agent may occur directly into the tissue at or near the site of fibrosis or wound repair or systemically. Multiple injections of the agent into the tissue at or near the site of fibrosis or wound repair or systemically are also provided.

One skilled in the art can also readily determine an appropriate dosage regimen for administering the molecular agent to a given subject. For example, the molecular agent can be administered to the subject once, such as by a single injection or deposition at or near the fibrosis or wound repair site. Alternatively, the molecular agent can be administered to a subject multiple times daily or weekly. Where a dosage regimen comprises multiple administrations, it is understood that the effective amount of molecular agent administered to the subject can comprise the total amount of molecular agent administered over the entire dosage regimen.

In certain embodiments, the molecular agent may be formulated as a pharmaceutical composition prior to administering to a subject, according to techniques known in the art. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

The molecular agents of the present disclosure can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the molecular agents of the present disclosure (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

The selection of the specific route of administration and the dose regimen is to be adjusted or titrated by the clinician according to methods known to the clinician in order to obtain the optimal clinical response. The amount of molecular agent to be administered is that amount which is therapeutically effective. The dosage to be administered will depend on the characteristics of the subject being treated, e.g., the particular subject treated, age, weight, health, types of concurrent treatment, if any, and frequency of treatments, and can be easily determined by one of skill in the art (e.g., by the clinician).

Pharmaceutical formulations containing the molecular agents of the present disclosure and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present disclosure. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

The molecular agents of the present disclosure can be formulated for parenteral administration by injection, e.g., by bolus injection or continuous infusion. Suitable parenteral administration routes include intravascular administration (e.g. intravenous bolus injection, intravenous infusion, intra-arterial bolus injection, intra-arterial infusion and catheter instillation into the vasculature); peri- and intra-tissue administration; subcutaneous injection or deposition including subcutaneous infusion (such as by osmotic pumps); direct (e.g., topical) application to the area at or near the site of fibrosis or wound repair; and inhalation.

Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present disclosure can also be formulated in rectal compositions such as suppositories or retention enemas, e.g., containing conventional suppository bases such as cocoa butter or other glycerides.

In addition to the formulations described previously, the compounds of the present disclosure can also be formulated as a depot preparation. Such long acting formulations can be administered by implantation (for example, subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present disclosure, for example, can be applied to a plaster, or can be applied by transdermal, therapeutic systems that are consequently supplied to the organism.

Pharmaceutical compositions of the molecular agents also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The molecular agents of the present disclosure can also be administered in combination with other active ingredients, such as, for example, adjuvants, protease inhibitors, or other compatible drugs or compounds where such combination is seen to be desirable or advantageous in achieving the desired effects of the methods described herein.

This invention and embodiments illustrating the method and materials used may be further understood by reference to the following non-limiting examples.

Example 1

Pregnant New Zealand white rabbits at 20-21 days gestation were operated via midline laparotomy under general anesthesia. The uterine horns were delivered and limited hysterotomies were performed so as to allow 1 cm linear full-thickness dorsal integumentary incisonal wounds to be placed on selected fetuses; no more than 2-3 fetuses were operated per animal. The amniotic volume was then replaced with pre-warmed saline or Plasmalyte solution, the hysterotomies sutured closed, and the laparotomy incision closed. The shaved dorsums of the adult rabbits were exposed and 2 cm full thickness incisional wounds were placed bilaterally, again taking care to not violate the subcutaneous tissue. These adult incisional wounds were covered by Opsite dressings to allow for undisturbed wound healing. After 12 hours, operated rabbits were reanesthetized and a 0.5-1 mm zone of tissue around the wound site was harvested (FW), as well as unwounded fetal skin (FC) from control littermates. Wounded and control adult skin tissue was also harvested and stored immediately at RNAlater® (Ambion, Austin, Tex.).

To monitor adult wound healing over a longer time course, non-pregnant rabbits carrying adult wounds only were followed to 28 days post-injury, with periodic sacrifice and harvesting of wound and control tissues at indicated intervals. The quality and quantity of total RNA extracted from fetal and adult wounded and control tissues were determined by measuring the OD 260/OD 280 ration using an ND-1000 spectrophotometer (Nanodrop Technologies, Inc., Wilmington, Del.) and by capillary electrophoresis with the Agilent 2100 BioAnalyzer (Agilent Technologies Inc., Palo Alto, Calif.).

The entire cDNA of rabbit CCT-eta was assembled by full length cloning and sequencing and then verified experimentally using end-sequence primers spanning the entire cDNA length. Total RNA extracted from FC, FW, adult control (AC) and adult wound (AW) tissues were subjected to quantitative comparative RT-PCR assays to determine the relative mRNA expression levels of CCT-eta as well as α-SMA. Using the comparative critical cycle (Ct) method and using GADPH as the endogenous control, the expression levels of the target gene products were normalized and relative abundance was calculated. Data were analyzed using the 7900 HT SDS software version 2.1 provided by Applied Biosystems.

Proteins were extracted from unwounded control and wounded adult skin using Tissue Protein Extraction Reagent (T-PER) obtained from Thermo Fisher Scientific (Rockford, Ill.). Protein concentration was measured using the Bradford assay. Equal quantities of protein extract were resolved by SDS-PAGE and transferred to a Whatman™ Protran pure nitrocellulose immobilization membrane. The membranes were probed with antibodies specific for CCT-eta and α-SMA, conjugated with HRP-labelled secondary antibody and the signals detected using western blotting. To confirm equal loading of proteins, immunoblots were probed against GADPH. The band intensity was measured using AlphaImager from Alpha Innotech Corporation (San Leandro, Calif.).

Results (FIG. 1): CCT-eta mRNA (SEQ ID No. 7) is reduced in fetal wounds and actually elevated in adult wounds. CCT-eta mRNA is persistently elevated in healing adult wounds. CCT-eta protein (SEQ ID No. 9) is elevated in adult wounds. α-SMA mRNA (SEQ ID No. 8) and protein (SEQ ID No. 10) are significantly increased in adult wounds.

Example 2

The role of CCT-eta (SEQ ID No. 9) in fibroblast motility and contractility, properties essential to wound healing and scar formation were examined. CCT-eta (but not CCT-beta) was found to be underexpressed in fetal fibroblasts compared to adult fibroblasts. An in vitro wound healing assay demonstrated that adult fibroblasts showed increased cell migration in response to epidermal growth factor (EGF) and platelet derived growth factor (PDGF) stimulation, whereas fetal fibroblasts were unresponsive.

Downregulation of CCT-eta in adult fibroblasts with short inhibitory RNA (siRNA) (SEQ. ID Nos. 1 and 2) reduced cellular motility, both basal and growth factor-induced; in contrast, siRNA against CCT-beta (SEQ ID Nos. 23 and 24) had no such effect.

Adult fibroblasts were more inherently contractile than fetal fibroblasts by cellular traction force microscopy; this contractility was increased by treatment with EGF and PDGF. CCT-eta siRNA (SEQ. ID Nos. 1 and 2) inhibited the PDGF-induction of adult fibroblast contractility, whereas CCT-beta siRNA (SEQ ID Nos. 23 and 24) had no such effect.

In each of these instances, the effect of downregulating CCT-eta was to modulate the behavior of adult fibroblasts so as to more closely approximate the characteristics of fetal fibroblasts.

Next, the effect of CCT-eta modulation on alpha-smooth muscle actin (α-SMA) expression, a gene product well known to play a critical role in adult wound healing, was examined. Fetal fibroblasts were found to constitutively express less α-SMA (SEQ ID No. 10) than adult cells. Reduction of CCT-eta with siRNA had minimal effect on cellular beta-actin but markedly decreased α-SMA; in contrast, reduction of CCT-beta had minimal effect on either actin isoform. Direct inhibition of α-SMA with siRNA reduced both basal and growth factor-induced fibroblast motility.

These results indicated that CCT-eta is a specific regulator of fibroblast motility and contractility and may be a key determinant of the scarless wound healing phenotype by means of its specific regulation of α-SMA expression.

Example 3

Methods: Healing adult wounds at eight days post-injury were harvested, sectioned and subjected to an in situ hybridization assay protocol using a CCT-eta-specific antisense probe.

Figure 2:
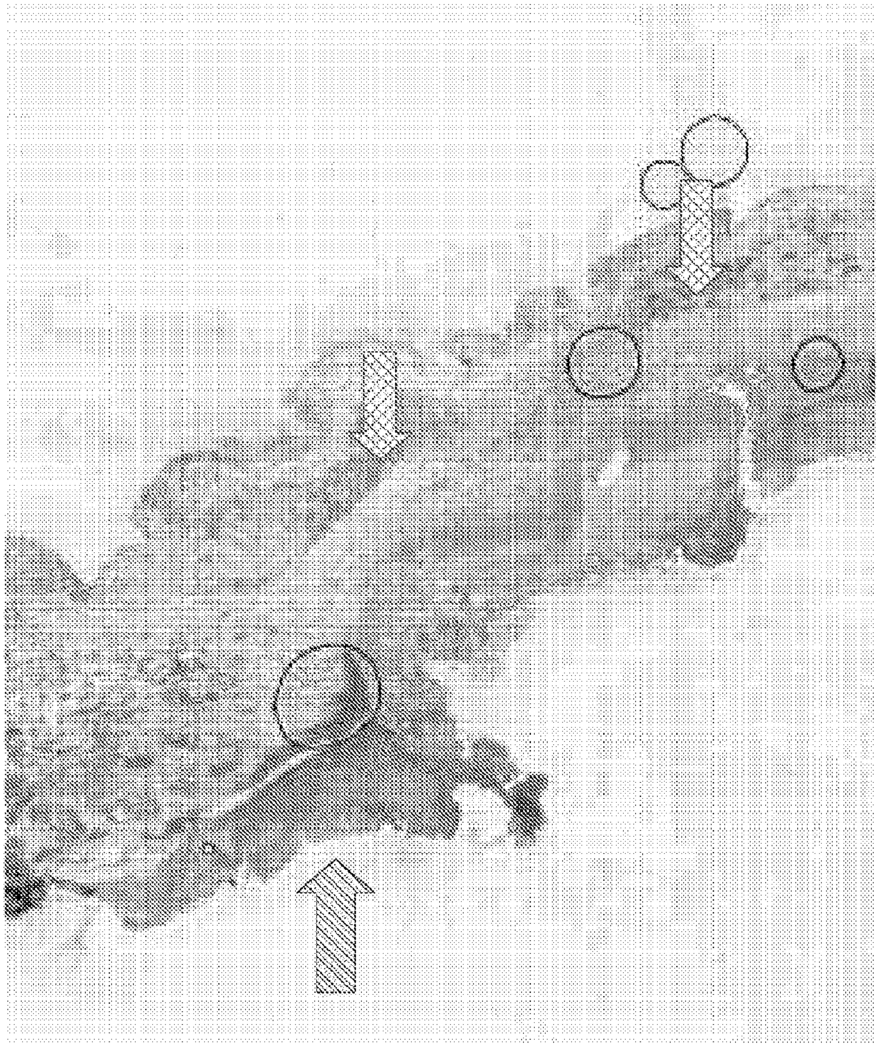
FIG. 2 illustrates in situ hybridization for CCT-eta in an adult wound.

Results (FIG. 2): CCT-eta elevation was clearly a local wound response, not a generalized systemic one. Multiple cell populations, including the leading edge of migrating keratinocytes, infiltrating fibroblasts, and even the muscle cells of the immediately neighboring panniculus carnosus all exhibited substantially increased levels of CCT-eta messenger expression.

Example 4

Purpose: The purpose of this study was to confirm that CCT-eta is increased at the protein level, not just at the message level.

Methods: Adult New Zealand white rabbits had incisional wounds placed on their dorsums and an occlusive dressing applied. Wounds were allowed to mature for up to 1 month, with some samples re-excised for analysis in the intervening period.

Figure 3:
FIG. 3 illustrates immunohistochemical demonstration of CCT-eta expression in a healing full-thickness integumentary wound.

Results: Immunohistochemistry on harvested healing wounds showed that, as seen in in situ experiments, CCT-eta expression was dramatically increased in the cell populations immediately bordering the zone of injury, including in the migrating tongue of epithelium (keratinocytes), in infiltrating fibroblasts, and in the underlying muscle tissue of the wounded panniculus carnosus (FIG. 3). Examination of the CCT-beta subunit as a control (see Table 1, SEQ ID Nos. 23 and 24) demonstrated no such increase by either in situ or immunohistochemistry.

Example 5

Purpose: To examine whether rabbit siRNA constructs designed to decrease rabbit CCT-eta expression can thereby decrease scar through the use of conventional liposome-mediated molecular transfection methods.

Methods: 5 μg of chemically synthesized rabbit siRNA against CCT-eta (SEQ. ID No. 1 and 2) was complexed with in vivo jetPEI reagent, a linear polyethylenimine. The N/P ratio (a measure of the ionic balance within the complexes) was set to 8, requiring 0.8 μl of jetPEI reagent, mixed with the siRNA and diluted to 5 μl using 10% glucose then incubated for 15 min at room temperature (in accordance with the manufacturer's instructions). When ready to inject the complexes were further diluted with normal saline to 200 μl and injected intradermally into dorsal incisional wounds placed on adult New Zealand white rabbits. Gross wound morphology and appearance were tracked for 28 days, at which time animals were sacrificed, wounds harvested, and micrographic histology also inspected.

Figure 4:
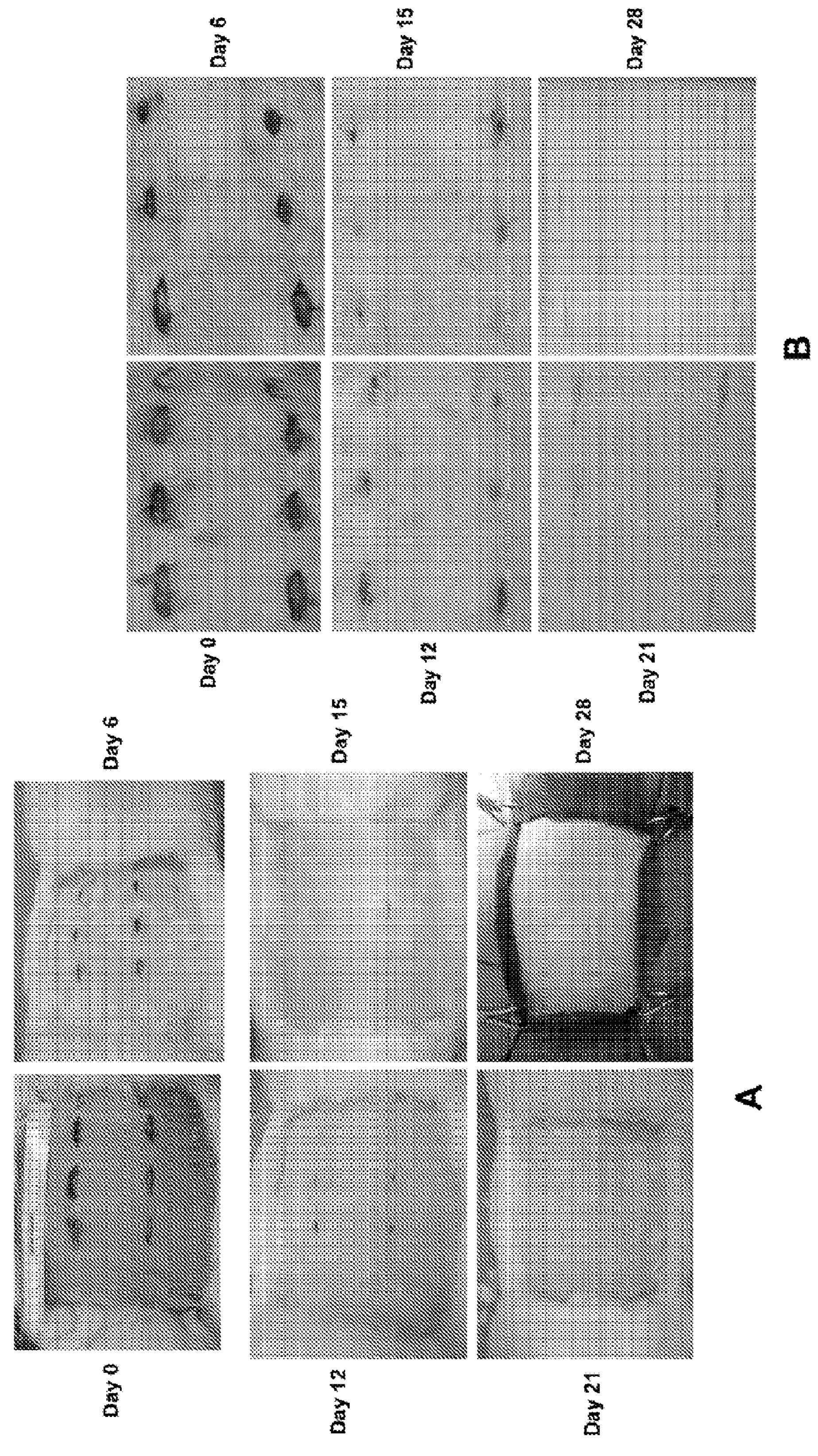
FIG. 4 illustrates healing rabbit wounds following intradermal administration of CCT-eta siRNA complexed with jetPEI liposomal reagent.

Results (FIGS. 4A and 4B): The jetPEI reagent/siRNA complex was well tolerated, eliciting no untoward inflammatory response or necrosis, with no evident attendant deleterious effect on wound healing. Grossly and micrographically, however, the effect on scar formation was minor at the concentration of chemical siRNA employed.

Example 6

Deliverable nanoparticles were formed from a complex of atelocollagen and siRNA by mixing the two solutions at 4°

C. where final concentrations of atelocollagen can range from 0.05% to 1.75%. Interestingly, at 4° C. atelocollagen is liquid, but at 37° C. it assumes a more gelatinous consistency. Thus, these nanoparticles can be locally administered topically in gel form (they can also be injected).

Methods: Nanoparticle complexes of atelocollagen with rabbit CCT-eta siRNA (SEQ ID Nos. 1 and 2) were evaluated as scar-reducing agents in our animal models. 5 μM rabbit siRNA solution was used topically and was also injected intradermally in full thickness dorsal incisional wounds. 400 μl of 10 μM CCT-eta siRNA (SEQ ID Nos. 1 and 2) was mixed with 400 μl of atelocollagen (Atelogene, Japan). The solution was mixed at 4 C for 20 minutes and 100 μl of the resulting mixture was applied either topically or directly injected into wound margins. In addition to an active rabbit CCT-eta siRNA (SEQ ID Nos. 1 and 2), a scrambled control rabbit siRNA (SEQ ID Nos. 3 and 4) was also applied (Table 1).

TABLE 1

| GENE | SEQUENCES |
|---|---|
| Rabbit CCT-eta | Sense- 5'-rGrArArCrGrArUrUrCrArGrUrArGrUrGrGrCrUTT 3' (SEQ ID No. 1)<br>Antisense- 5'rArGrCrCrArCrUrArCrUrGrArArUrCrGrUrUrCTT 3' (SEQ ID No. 2) |
| Rabbit CCT-beta | Sense- 5'-rGrGrArGrArArArGrUrUrGrArArCrGrUrArUrUTT-3' (SEQ ID No. 23)<br>Antisense- 5'-rArArUrArCrGrUrUrCrArArCrUrUrUrCrUrCrCTT-3' (SEQ ID No. 24) |
| Rabbit α-SMA | Sense- 5'rArGrArGrArArArUrUrGrUrGrCrUrArUrGrUrCTT3' (SEQ ID No. 5)<br>Antisense- 5'rGrArCrArUrArGrCrArCrArArUrUrUrCrUrCrUTT3' (SEQ ID No. 6) |
| Scramble Control CCT-eta | Sense- 5'rGrArArcrGrArUrUrCrGrArArUrGrCrUrGrGrUTT3' (SEQ ID No. 7)<br>Antisense- 5'rArCrCrArGrCrArUrUrCrGrArArUrCrGrUrUrCTT3' (SEQ ID No. 8) |

Animals were again allowed to heal for 28 days before the wounds/scars were re-excised and analysed for CCT-eta expression.

Figure 5:
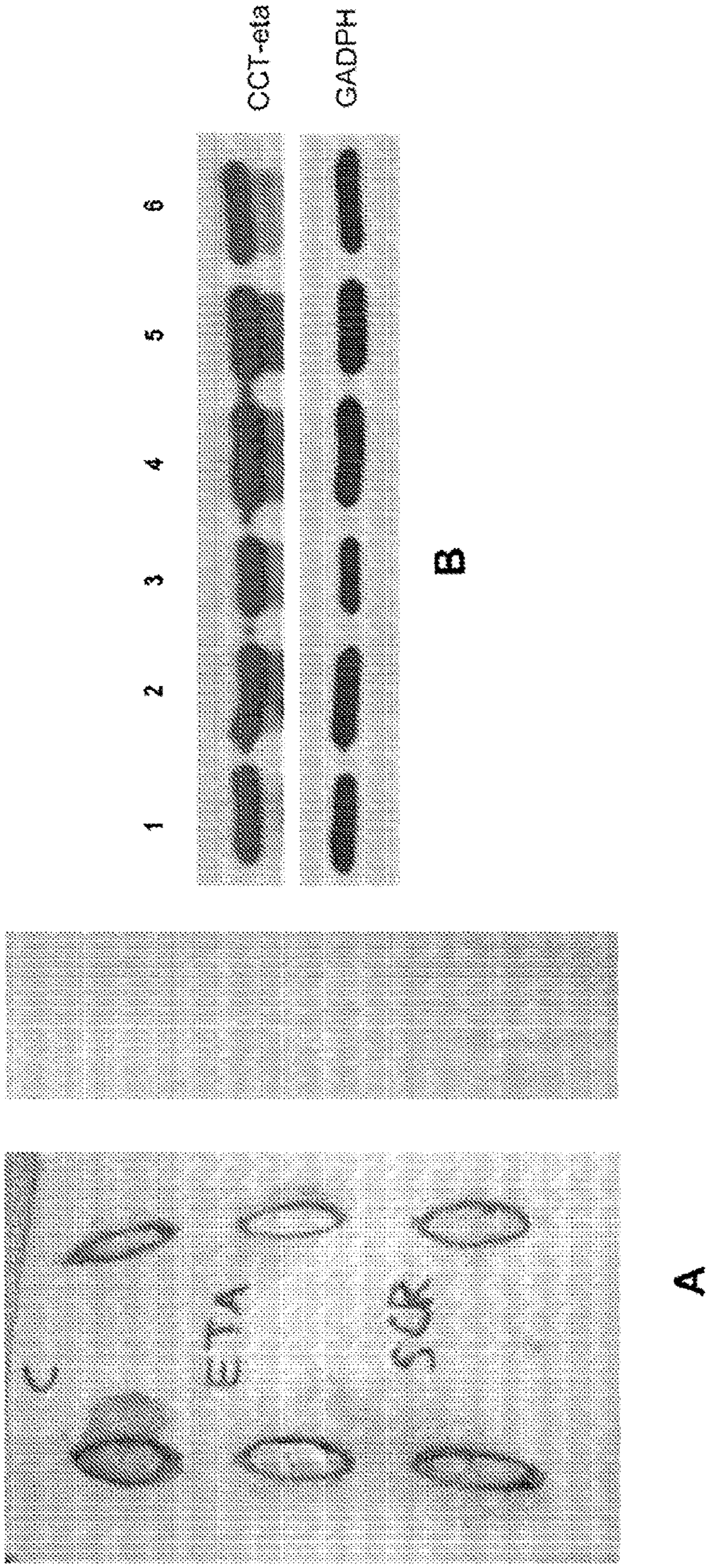
FIG. 5 illustrates healing rabbit wounds following intradermal administration of CCT-eta siRNA complexed with atelocollagen.

Results (FIG. 5): The data demonstrated that atelocollagen, either alone or complexed with siRNAs, is well tolerated by integumentary tissues, eliciting no abnormal tissue response with no resulting impairment of healing (FIG. 5A). Scar formation appeared to proceed similarly in all conditions tested at this dose of siRNA; no significant difference in CCT-eta expression was observed at 28 days (FIG. 5B).

Example 6

2 μl lipofectamine and 2.5 μl of rabbit CCT-eta siRNA (SEQ ID No. 1 and 2) were mixed with 100 μl of OptiMEM (corresponding to a final concentration of 50 pM). After incubating for 20 min at room temperature (to allow nanoparticles to assemble) the final rabbit siRNA/lipofectamine mixture was combined with 1% agarose stock solution to obtain 0.3% agarose transfection solution. After careful mixing the gel-based mixture was topically applied to 2 cm full thickness dorsal incisional wounds on adult New Zealand white rabbits. Wounds were allowed to heal over 28 days with periodic harvesting of selected wounds/animals in the interim. Harvested samples were analyzed for reduction of CCT-eta expression by qRT-PCR and Western blot.

Figure 6:
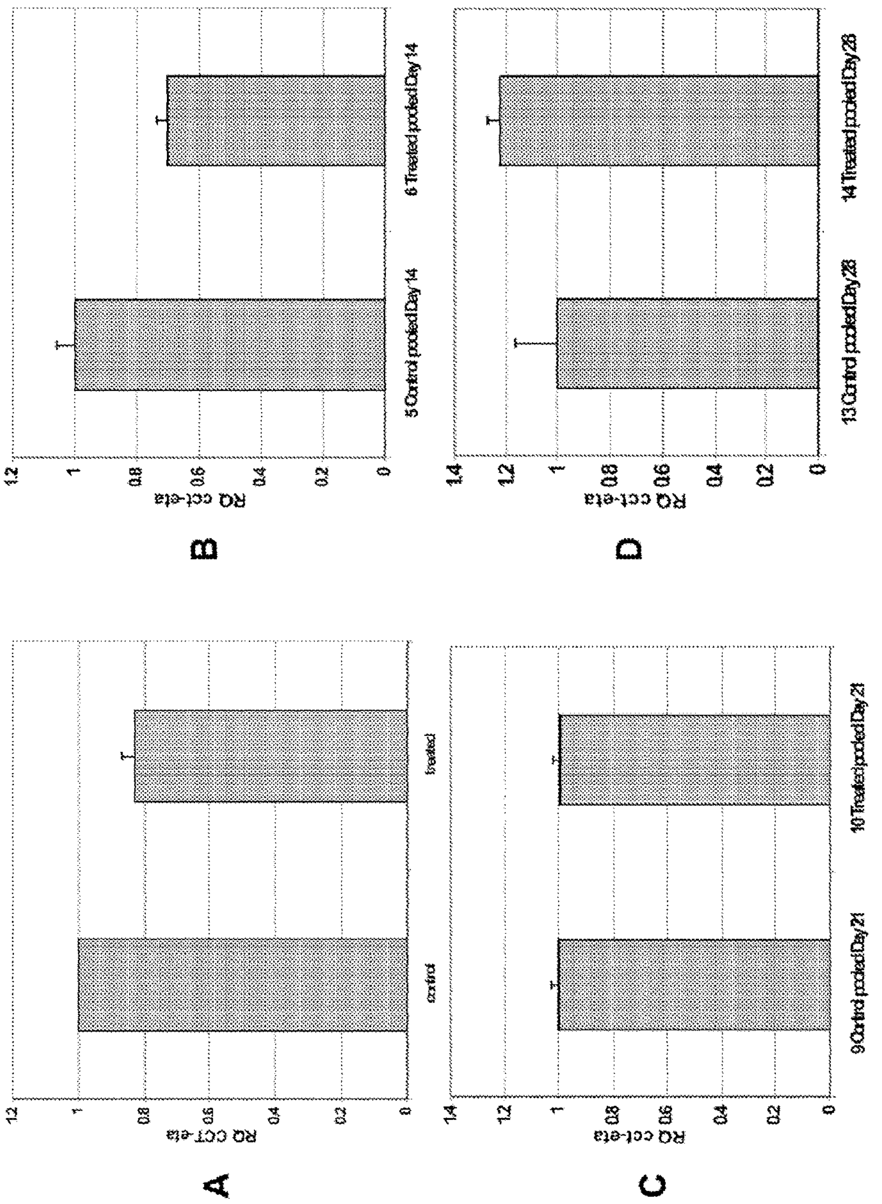
FIG. 6 illustrates quantitation of CCT-eta mRNA after administration of CCT-eta siRNA in an agarose gel matrix.

Results (FIG. 6): qRT-PCR demonstrated that there was a reduction of the CCT-eta message by up to 30% for a two week period after application (FIG. 6B). At day 21 (FIG. 6C) after application CCT-eta levels had returned to baseline in the treated compared to control groups, where they remained at the 28 day time point (FIG. 6D) as well. Quantitation of CCT-eta protein levels by Western blot essentially paralleled these results.

Example 7

Figure 7:
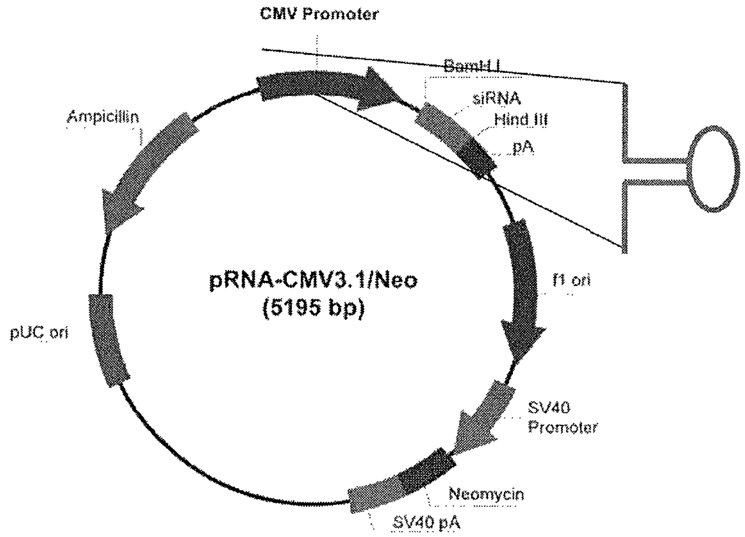
FIG. 7 illustrates the schematic depiction of pRNA-mEta 1203siRNA.

Using the rabbit siRNA sequence against CCT-eta (SEQ ID Nos. 1 and 2), the corresponding sequence from the mouse CCT-eta was used to design a DNA insert encoding a hairpin RNA targeting CCT-eta using the Ambion siRNA Converter program. This program generated two DNA sequences (see Table 2, SEQ ID Nos. 25-28) containing the hairpin/loop sequence flanked by restriction site cloning sequences. Two oligonucleotides comprising these sequences were obtained from IDT. The oligos were rendered doubled stranded following standard protocol (as per the manufacturer's recommendations) and cloned into pRNA-CMV3.1-Neo using BamIII/HindIII. The ligated plasmid was transformed into OneShot/TOP10 cells (Invitrogen) and individual clones were used to prepare plasmid DNA for sequencing and transfection. Sequencing of hairpin constructs may be difficult and often results in truncated sequencing due the obstructive double stranded topology; however, the recovered plasmid contained the cloned sequences up to the end of the sequencing read (approximately halfway through the ligated oligos). This plasmid was designated pRNA-mEta 1203siRNA (FIG. 7).

TABLE 2

| | |
|---|---|
| Mouse CCT-eta-1203siRNA | Forward- 5'-GATCCAAGAATGACTCTGTGGTGGCTTTCAAGAGAAGCCACCACAGAGTCATTCTTA-3' (SEQ ID No. 25)<br>Reverse- 5'-AGCTTAAGAATGACTCTGTGGTGGCTTCTCTTGAAAGCCACCACAGAGTCATTCTTG-3' (SEQ ID No. 26) |
| Mouse CCT-eta-1205siRNA | Forward- 5'-GATCCGAATGACTCTGTGGTGGCTTTCAAGAGAAGCCACCACAGAGTCATTCTTA-3' (SEQ ID No. 27)<br>Reverse- 5'-AGCTTAAGAATGACTCTGTGGTGGCTTCTCTTGAAAGCCACCACAGAGTCATTCG -3' (SEQ ID No. 28) |
| Luciferase (control) | 5'-GGATCCTCGCTTACCGATTCAGAATGGTTGATATCCGCCATTCTGAATCGGTAAGCGACGAAGCTT-3' (SEQ ID No. 29) |

The pRNA-CMV3.1 control plasmid contains the following DNA sequence: 5'-GGATCCTCGCTTACCGATTCA-GAATGGTTGATATCCGCCATTCTGAATCGGTA AGC-GACGAAGCTT-3' (SEQ ID No. 29), which encodes an siRNA that knocks down expression of luciferase. This was transfected into NIH3T3 fibroblasts to use as a control along with pRNA-mEta 1203siRNA, using standard protocols and Lipofectamine 2000 (Invitrogen). After 48 hours, cells were passaged and stable lines were established by growing cells for 3 weeks in the presence of 1 μg/mL G418. After 3 weeks, cells were passaged and approximately $1\times10^6$ cells were plated onto a 6-well plate. After 24 hrs, cells were washed once with PBS, then lysed for 5 minutes in-dish using m-PER reagent (Pierce), followed by centrifugation following manufacturer protocol. The soluble supernatant was transferred to ice, and then an aliquot was diluted with SDS-PAGE sample buffer and separated on a 4-20% gradient SDS-PAGE gel (ready-made, Bio-Rad). Samples were transferred to a PVDF membrane (Millipore ImmobilonP), and blocked for 1 hour at room temperature in TBST+5% Block. The blot was rinsed and incubated with rat anti-Eta (Serotek, 1:500) overnight at 4 C, rinsed and incubated with Goat anti-Rat (Biosource, 1:5,000) for 1 hour at room temperature. Blot was developed with Amersham ECL reagent. To determine loading efficiency, after detection the blot was incubated with mouse anti-GAPDH (ABCAM, 1:5,000) and incubated for 1 hour at room temperature in TBST, rinsed, and incubated with Goat anti-Mouse (Amersham, 1:5,000) for 1 hour at room temperature in TBST, before being developed with Amersham ECL reagent.

Figure 8:
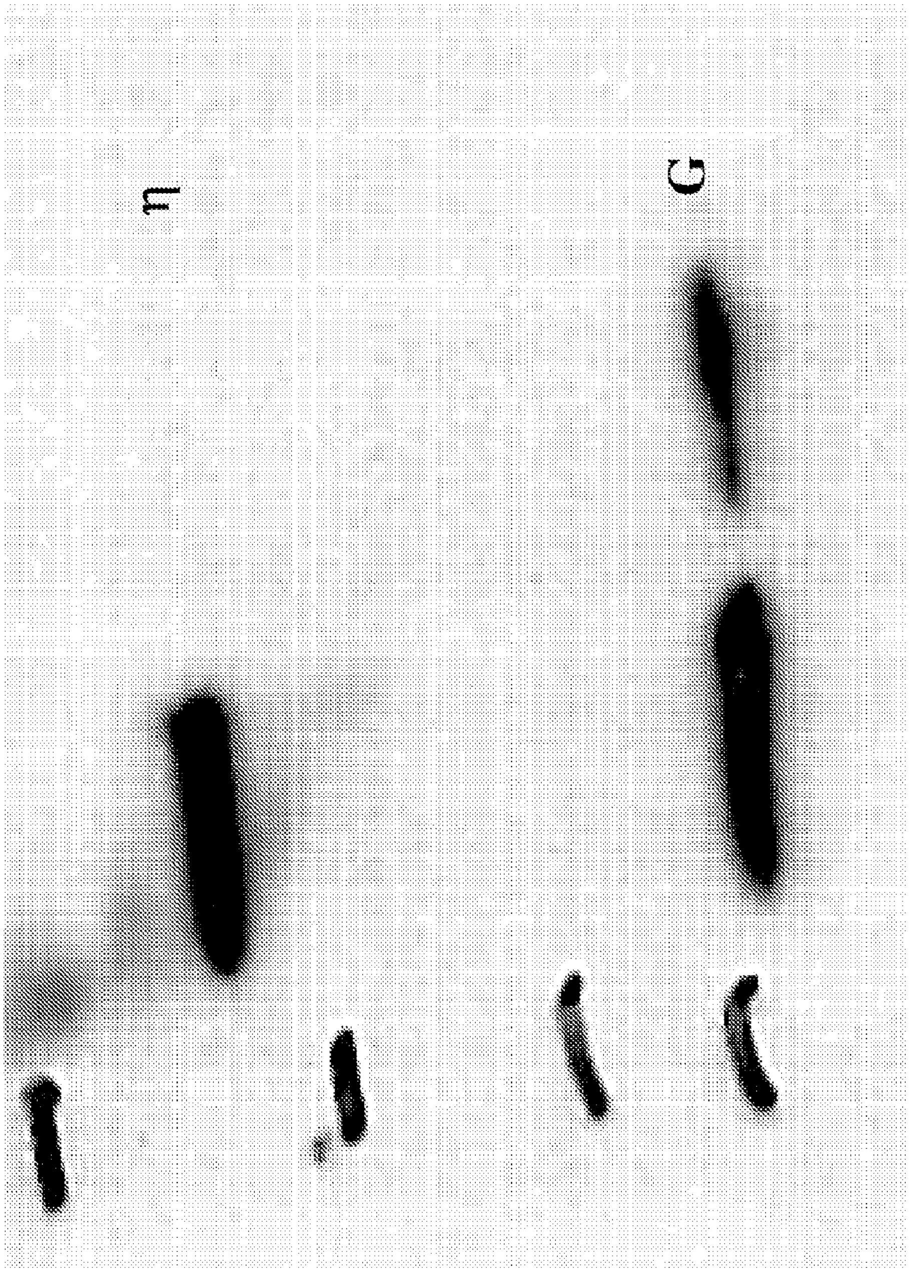
FIG. 8 illustrates Western blot results of NIH3T3 fibroblasts transfected with pRNA-CMV3.1 control plasmid (left lane) and pRNA-mEta 1203siRNA (right lane).

Results (FIG. 8): CCT-eta protein (SEQ ID No. 9) is readily detectable in the control cells but is markedly decreased (to the point of being virtually undetectable) in the cells carrying pRNA-mEta 1203siRNA. GAPDH used as a loading control is similar in both cell types. These data indicate that pRNA-mEta 1203siRNA is able to effectively suppress CCT-eta message and protein.

Example 8

Rabbit adult fibroblasts were cultured in RPMI 1640 supplemented with 10% fetal bovine serum. Transfection of rabbit siRNAs versus CCT-eta (SEQ ID Nos. 1 and 2) and CCT-beta (SEQ ID Nos. 23 and 24) was performed with the manufacturer's protocol using Lipofectamine 2000. Briefly, 7.5 μl of 20 μM siRNA was mixed with 200 μl of Opti-MEM; 4 μl of Lipofectamine 2000 was diluted into 200 μl of Opti-MEM and incubated at room temperature for 5 min. After the incubation, the diluted Lipofectamine 2000 was combined with the diluted rabbit siRNAs and then incubated for an additional 20 min (siRNA sequences targeting both CCT subunits and α-SMA were used at a concentration of 150 pM). A total of 400 μl of siRNA-Lipofectamine 2000 complexes was added to each well of cultured rabbit adult fibroblasts at ~90% confluence in a six well plate. After 24 h incubation at 37 C the cells were switched to quiescent media (RPMI 1640 medium containing 0.1% dialyzed FBS along with antibiotics) and left for 48 h. After 48 h of incubation in quiescent media cells were subjected to an in vitro scratch wounding protocol and followed for another 48 h; at this same time, cell populations were also stimulated either with EGF (1 nM)/PDGF (200 nM) or control. Thus, during the period of cell motility assayed these growth factors (or control, that is, no treatment) were continuously present. At the conclusion of this period, cells were harvested and total RNA and protein were isolated.

Quantitative reverse-transcription polymerase chain reaction (qRT-PCR) was then performed to confirm that the appropriate target CCT subunit mRNA was reduced (data not shown). Total cellular protein was examined by Western blot for accumulation of CCT-eta, CCT-beta, α-SMA, beta-actin, and GAPDH as a loading control.

Figure 9:
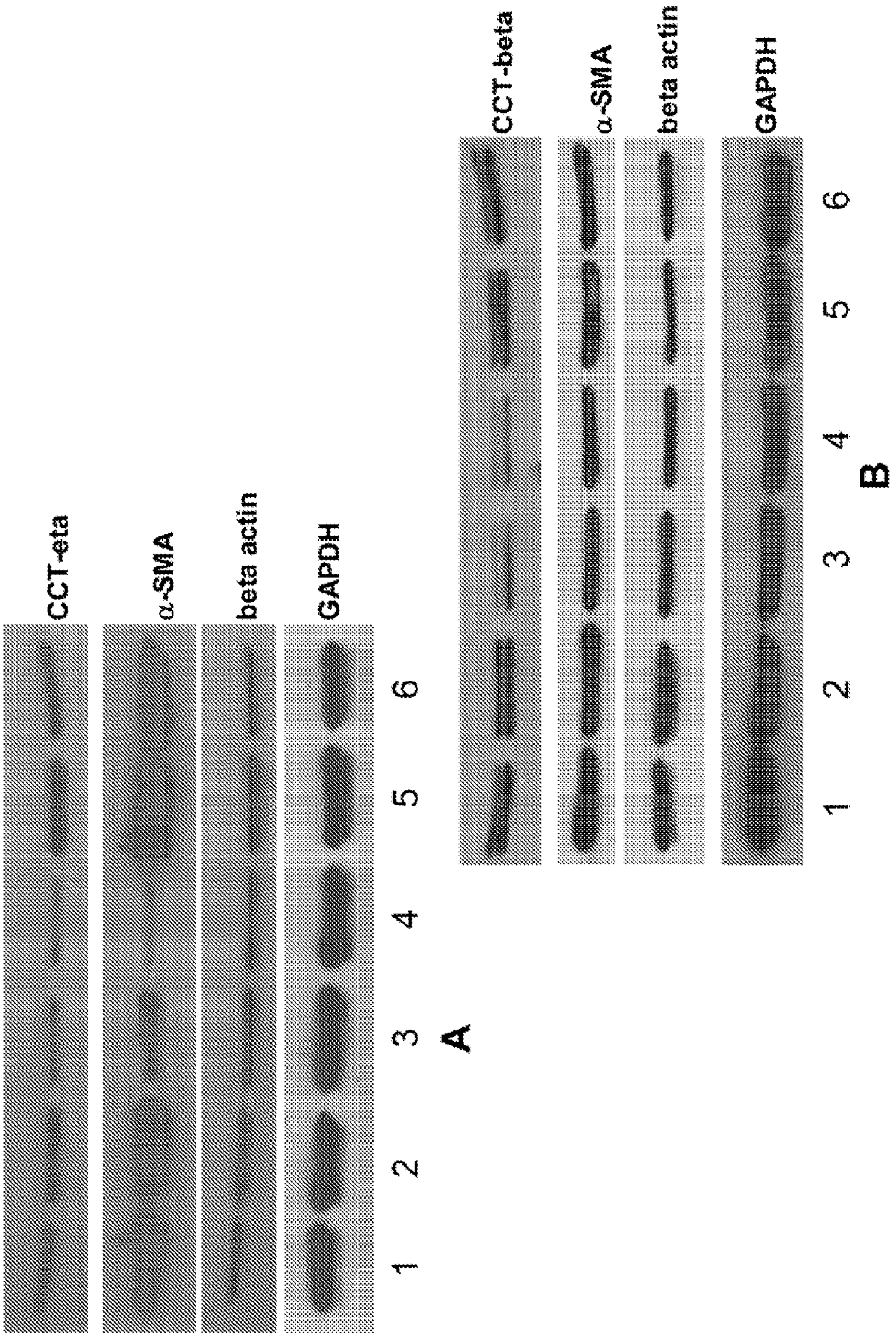
FIG. 9 illustrates the effect of siRNA versus CCT-eta and CCT-beta on cellular actin isoforms. (A) Representative Western blot of protein expression after administration of CCT-eta siRNA. 1=no treatment. 2=EGF alone. 3=CCT-eta siRNA alone. 4=CCT-eta siRNA+EGF. 5=Scrambled control siRNA alone. 6=Scrambled siRNA+EGF. Note that administration of CCT-eta siRNA drastically reduces the quantity of accumulated α-SMA. (B) Representative Western blot of protein expression after administration of CCT-beta siRNA. Lanes 1-6 are as in FIG. 9A, except CCT-beta rather than CCT-beta siRNA was used.
Figure 14:
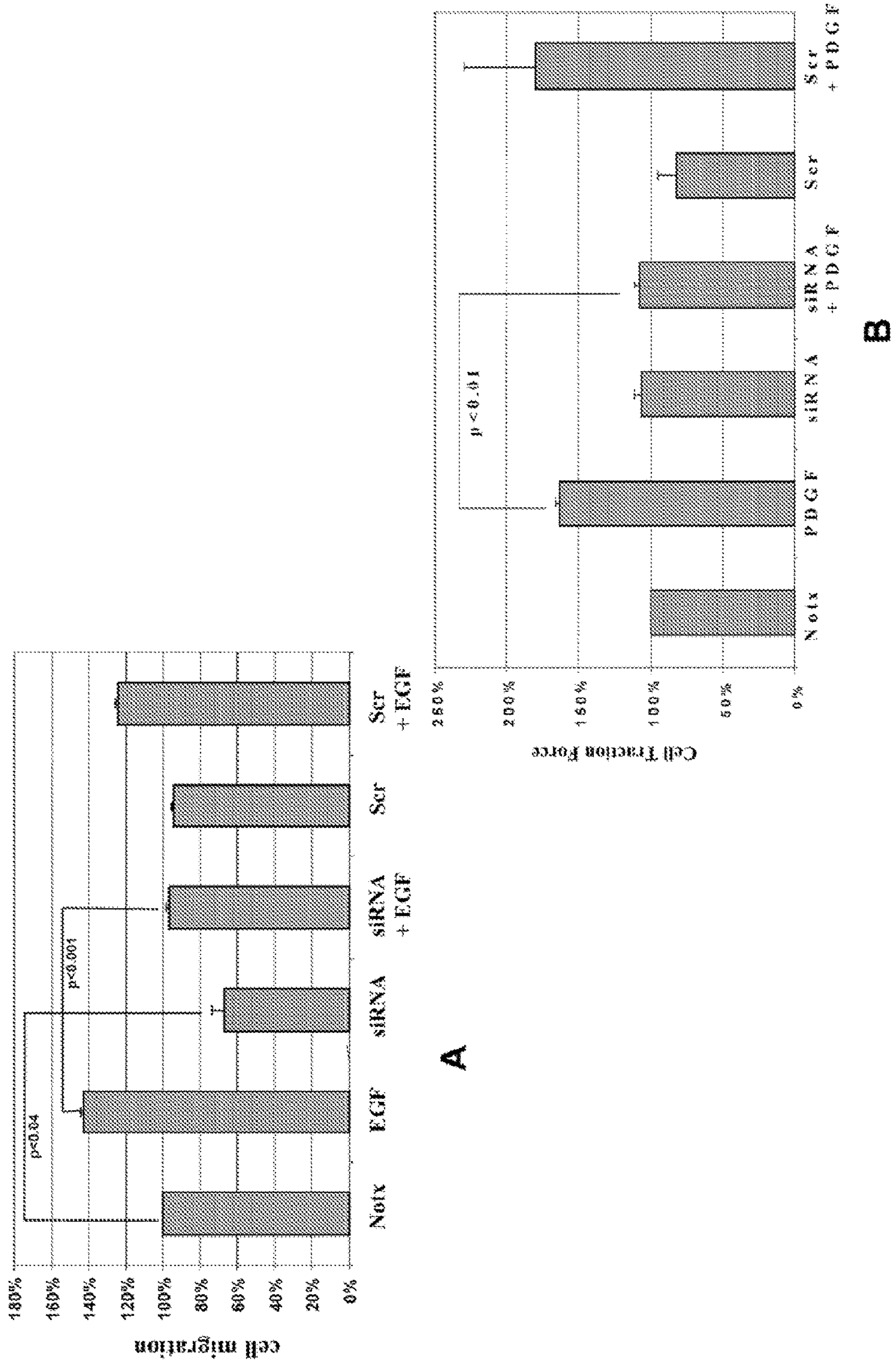
FIG. 14 illustrates siRNA versus CCT-eta's effect on adult fibroblast baseline motility and EGF-induced motility. (A) siRNA versus CCT-eta decreases adult fibroblast baseline motility and EGF-induced motility; a scrambled control siRNA does neither. (B) siRNA versus CCT-eta abolishes PDGF-induced contractility in adult fibroblasts; scrambled control has no such effect.

Results (FIGS. 9 and 14): siRNA versus CCT-eta and CCT-beta effectively decreased their target proteins. Beta-actin levels were unaffected by reduction of either CCT isoform. Notably however, α-SMA levels were markedly decreased when CCT-eta siRNA was employed, but were essentially unchanged with use of CCT-beta siRNA. Reduction of CCT-eta can alter the cytoskeletal properties of fibroblasts at the cellular level which, writ large onto the cellular population in a healing wound, may thereby result in altered tissue contractility as well.

siRNA versus CCT-eta (SEQ ID Nos. 1 and 2) decreases adult fibroblast baseline motility and EGF-induced motility (FIG. 14A), whereas a scrambled control siRNA (SEQ ID Nos. 3 and 4) does neither. siRNA versus CCT-eta (SEQ ID Nos. 1 and 2) abolishes PDGF-induced contractility in adult fibroblasts; scrambled control has no such effect (FIG. 14B).

Example 9 siRNA agarose/siRNA formulation, using siRNA against CCT-eta (SEQ ID Nos. 1 and 2), is applied topically to incisional/excisional wounds at the time of wounding, then again at 7 days post-injury, and again at 14 days post-injury. Wounds are then allowed to progress to complete closure, typically between 4-5 weeks after wounding. Wounds are then harvested for a variety of molecular, histologic and other analyses.

Results: There was no significant difference in rate of wound closure between treated and untreated control wounds with this protocol, and no signs of induced toxicity or necrosis on histologic examination.

Figure 10:
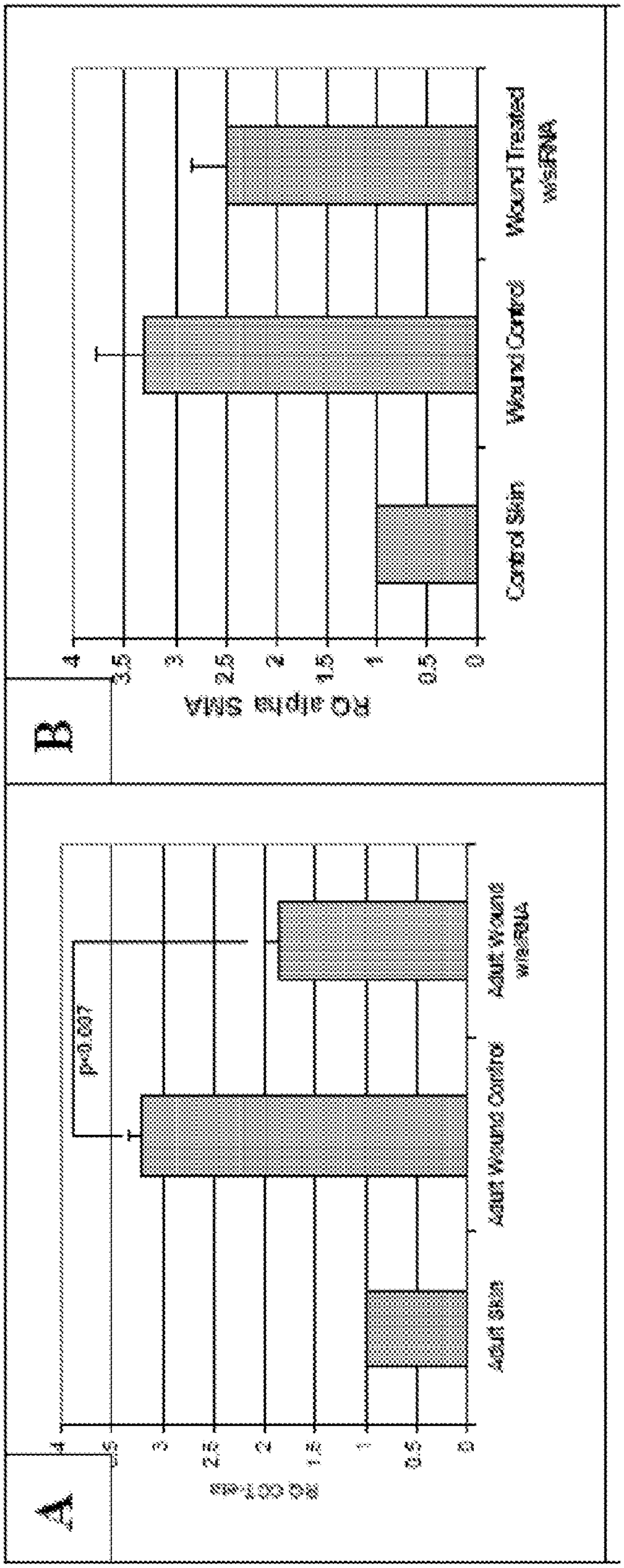
FIG. 10 illustrates the effect of siRNA on CCT-eta and α-SMA mRNA accumulation.

Next, qRT-PCR examination of control skin, untreated control wound, and rabbit siRNA-treated wound for rabbit CCT-eta mRNA expression confirmed that wounding caused a persistent elevation in CCT-eta at 4-5 weeks post-injury, and that this increase was significantly lessened by siRNA treatment. Thus, the protocol of repeated siRNA administration was apparently effective at suppressing CCT-eta expression for 4-5 weeks (FIG. 10A).

The effect of siRNA treatment on α-SMA RNA was also examined. There was a reduction of α-SMA RNA (FIG. 10B). Without intending to be bound by theory, it may be that downstream inhibition of α-SMA protein (by reduction of CCT-eta protein) leads to formation of α-SMA degradation products, and there is some evidence that such products may negatively regulate transcription.

Example 10

Purpose: To see if putative alteration of fibroblast physiology in vivo by our rabbit CCT-eta siRNA (SEQ ID Nos. 1 and 2) could diminish wound collagen accumulation.

Methods: Hydroxyproline assays were conducted to determine the total collagen content of the control versus treated wounds. Increased deposition of collagen is ultimately the most significant hallmark of scar formation.

Figure 11:
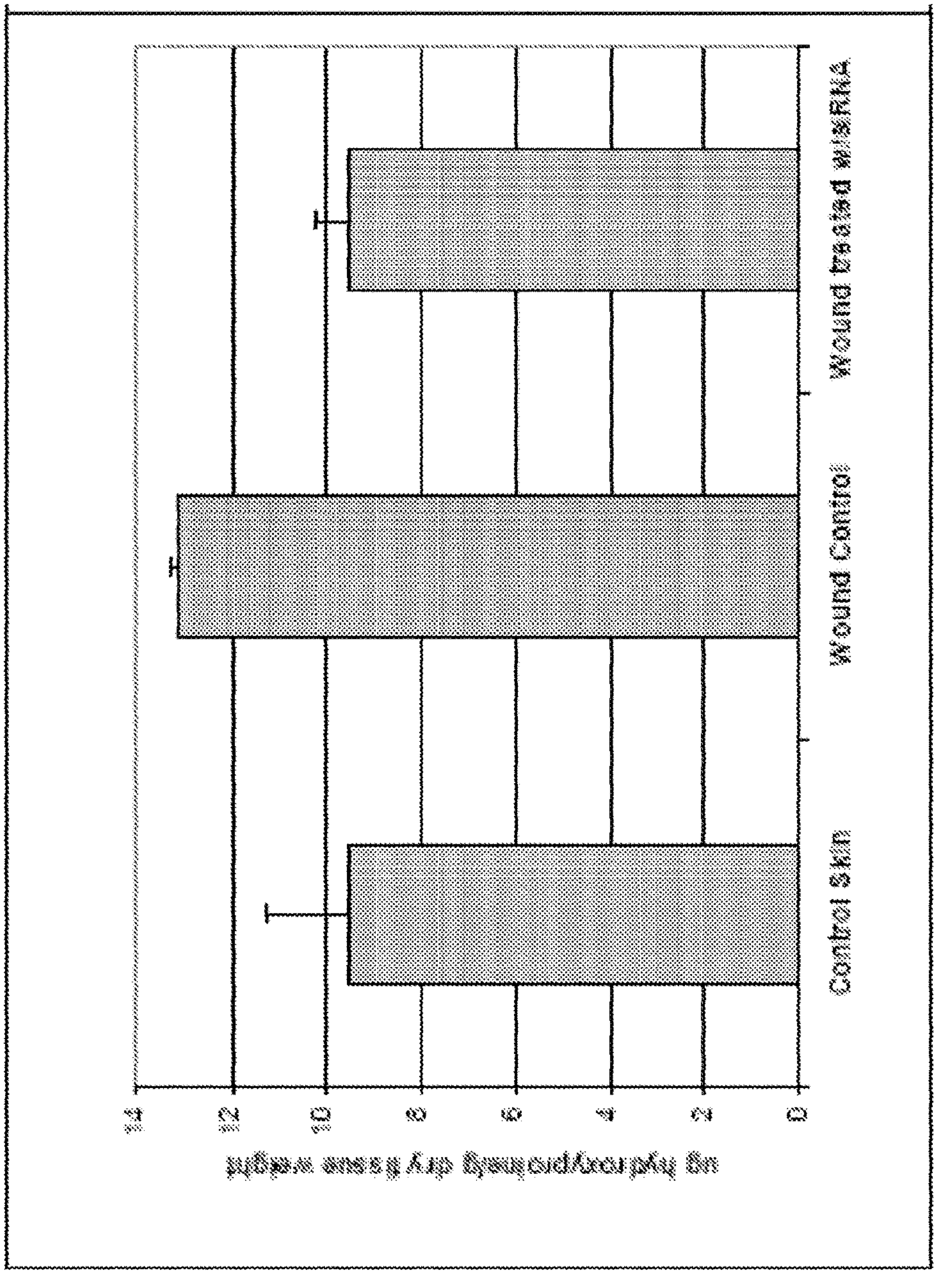
FIG. 11 illustrates the effect of CCT-eta siRNA on total wound collagen.

Results (FIG. 11): Treatment of healing wounds with rabbit CCT-eta siRNA (SEQ ID Nos. 1 and 2) significantly decreased the amount of collagen deposited in those wounds. These results establish a likely mechanism by which CCT-eta reduction can effect fibroblast physiology (and therefore wound physiology). They demonstrate that signature molecular markers of scar formation can be inhibited by rabbit siRNA versus CCT-eta (SEQ ID Nos. 1 and 2), and that a modest regimen of intermittent application of rabbit siRNA to the wound can have an effect that modulates the wound healing response through all of the inflammatory and most of the proliferative stages of wound healing.

Figure 12:
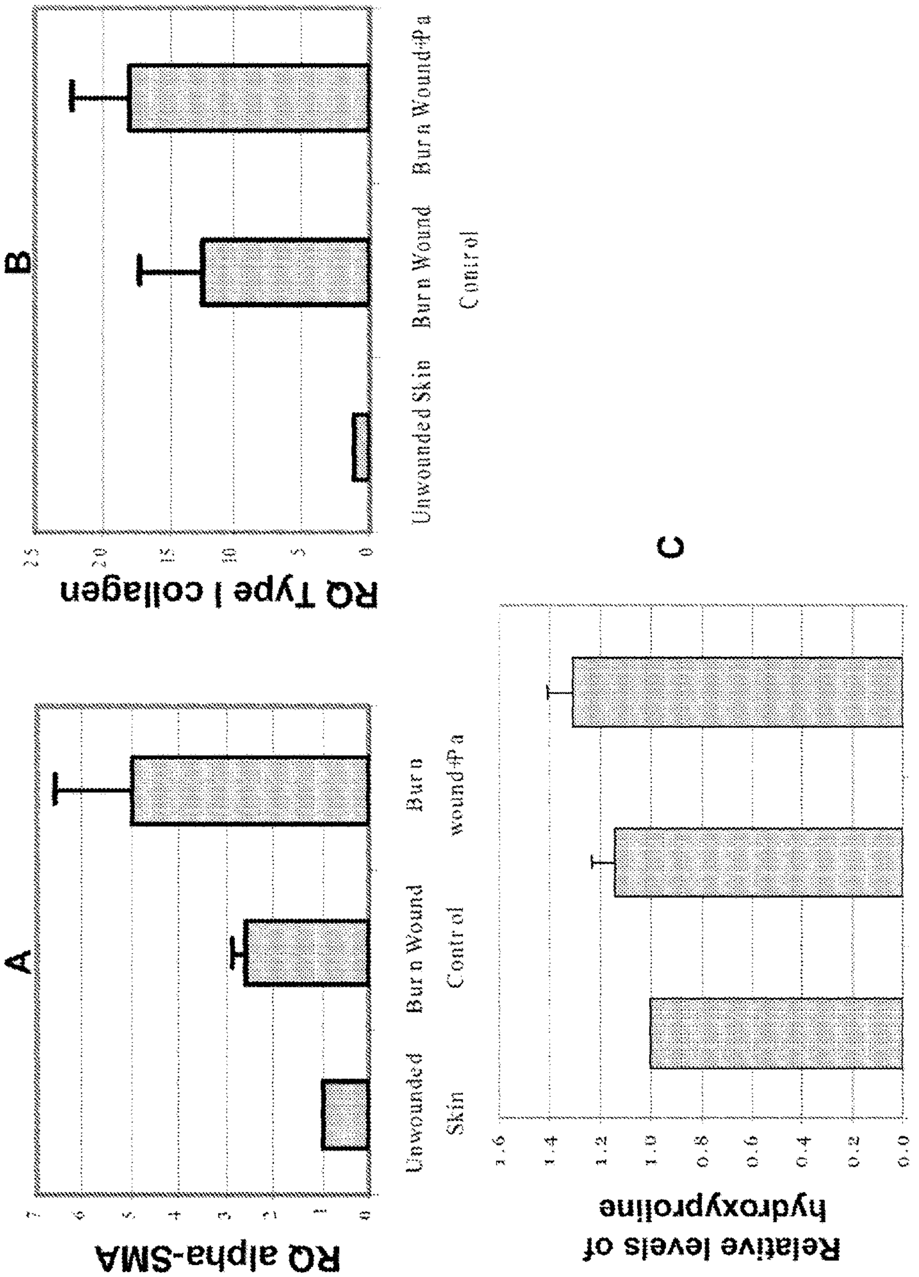
FIG. 12 illustrates the molecular evaluation of markers for scar formation in burn wound infection. (A) qRT-PCR of α-smooth muscle actin mRNA. (B) qRT-PCR of type I collagen mRNA. (C) Quantitation of tissue hydroxyproline (thereby quantifying collagen protein accumulation).
Figure 13:
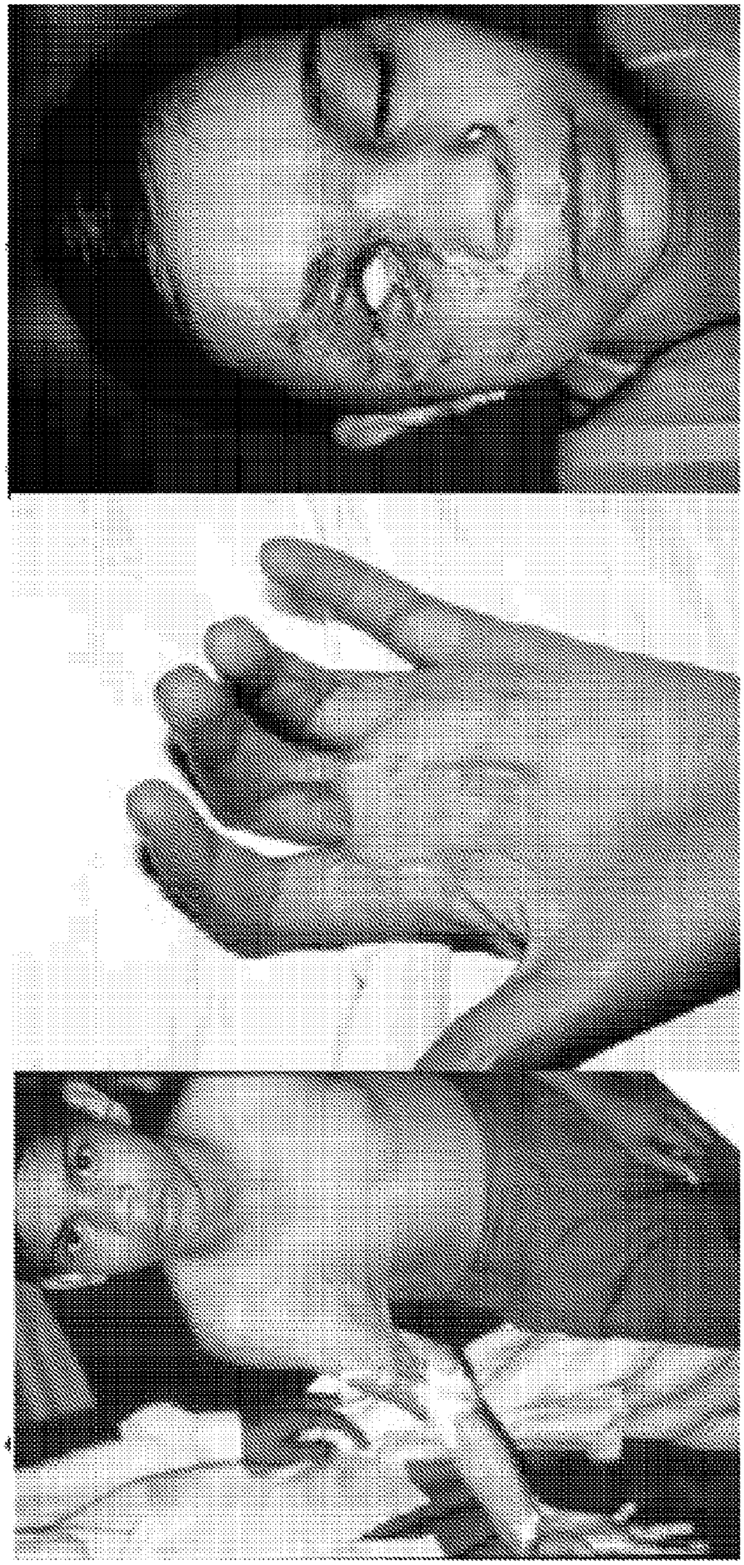
FIG. 13 illustrates three patients demonstrating crippling morbidity of scar due to burn and blunt injury to the face and extremities.

Burn wounds have much higher levels of α-SMA than control skin, with infected burn wounds much higher still (FIG. 12A). As with α-SMA, burn injury leads to a significant increase in collagen message accumulation, with infection significantly adding further to the increase (FIG. 12B). Burn injury leads to increased collagen protein, with infection leading to further collagen deposition, consistent with increased scarring (FIG. 12C).

Example 11

Figure 15:
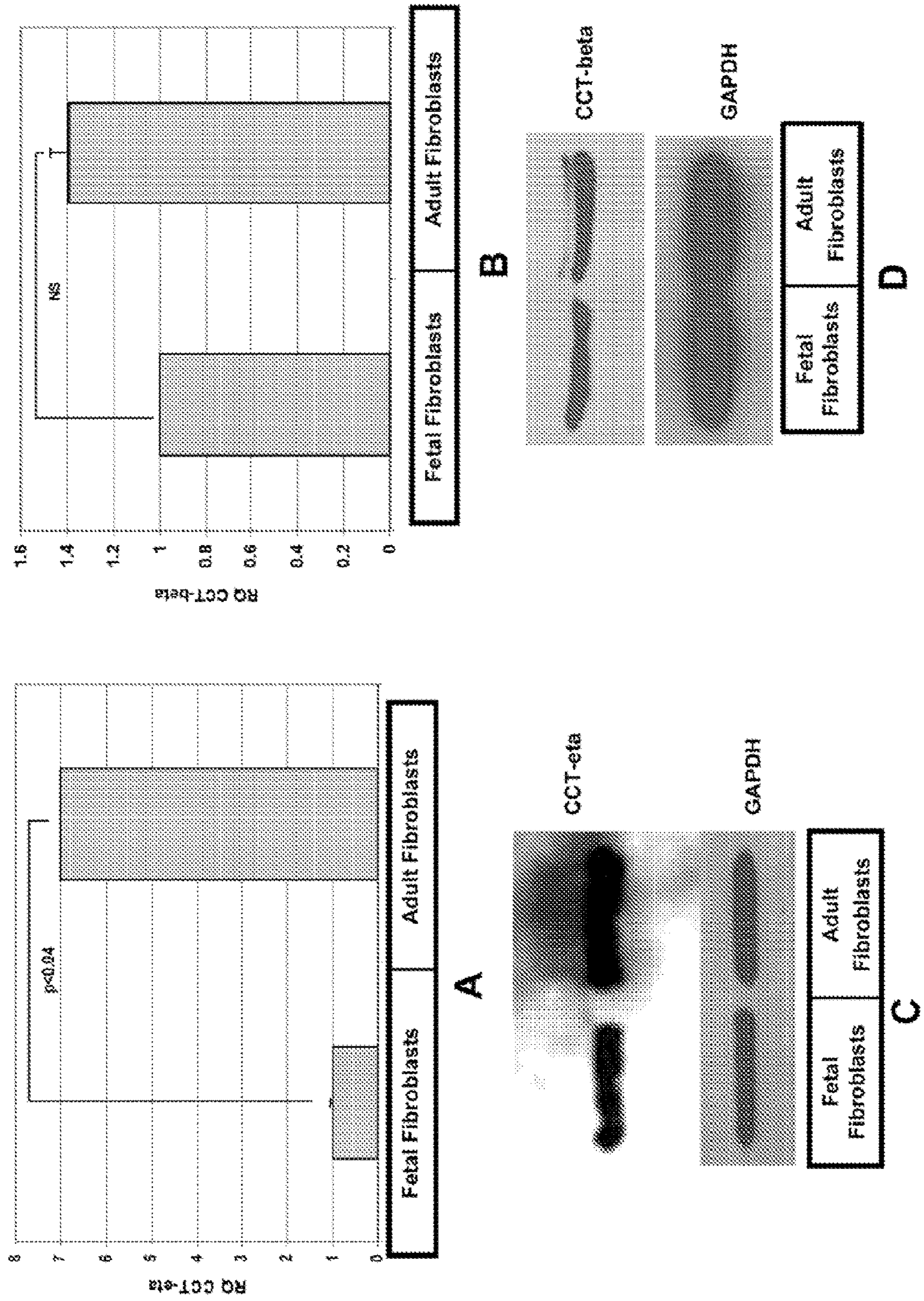
FIG. 15 illustrates that CCT-eta but not CCT-beta protein and mRNA are differentially expressed in fetal versus adult fibroblasts.

RNA and protein extracted from fetal and adult fibroblasts were subjected to qRT PCR (FIGS. 15A and 15B) and Western blot (FIGS. 15C and 15D) analyses respectively. CCT-eta mRNA (SEQ ID No. 7) was significantly more abundant in adult fibroblasts when compared to fetal fibroblasts (15A); there was no significant difference in CCT-beta message levels between fetal and adult fibroblasts (15B). Values are means±SEM of three independent studies performed in duplicate. Statistical analyses were performed using Student's t test. NS=non-significant. Equal amounts of protein loaded from fetal and adult fibroblasts showed that adult fibroblasts express significantly greater CCT-eta protein (15C). In contrast CCT-beta protein levels were not different between fetal and adult fibroblasts (15D). Blots shown are representative of at least three different experiments.

Figure 16:
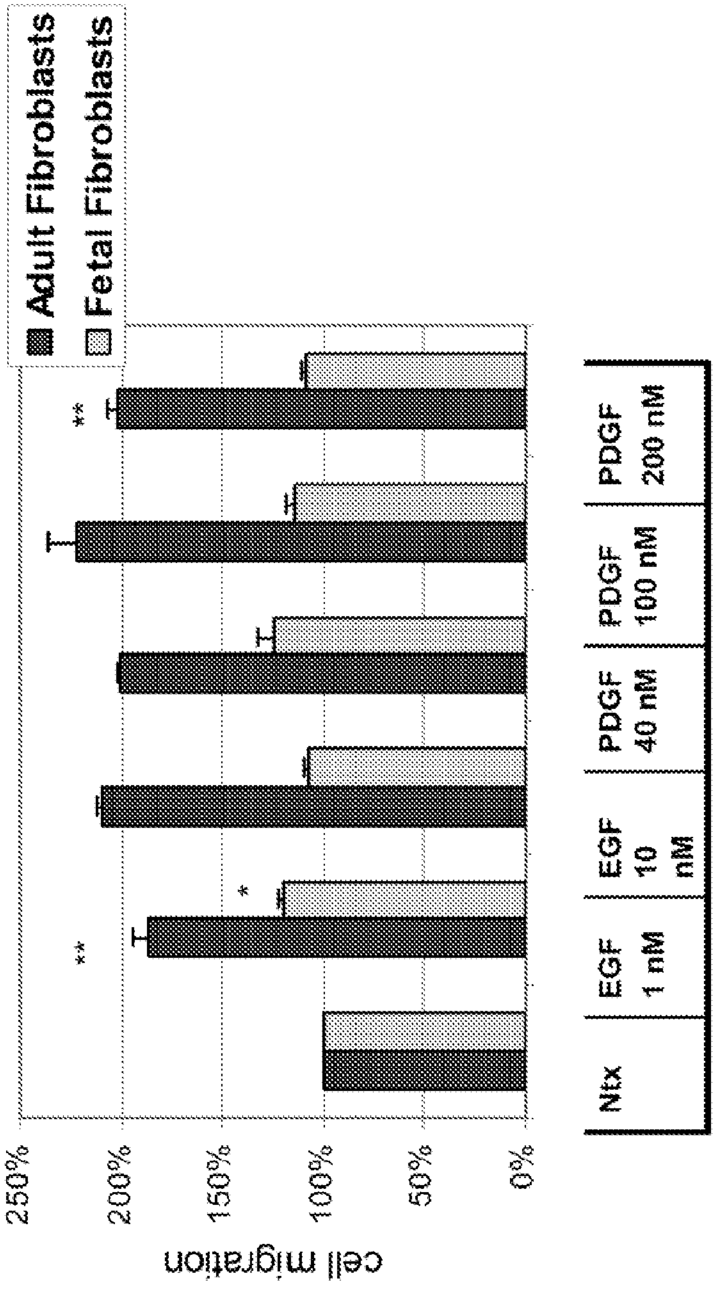
FIG. 16 illustrates that cell migration of adult but not fetal fibroblasts is responsive to EGF and PDGF induction.
Figure 17:
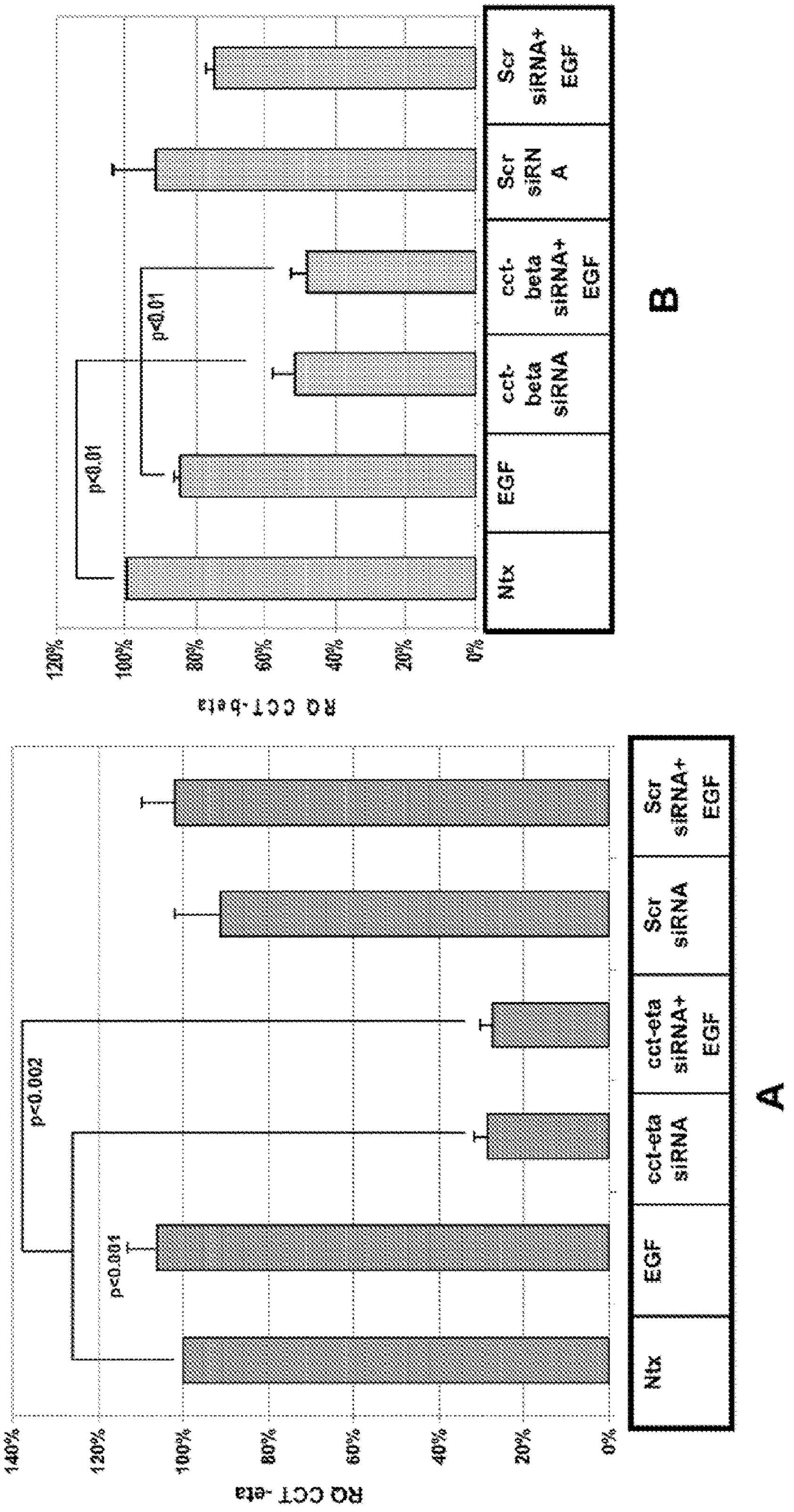
FIG. 17 illustrates siRNAs against CCT-eta and CCT-beta decrease both basal and EGF-induced mRNA and protein levels of their targets in fibroblasts.
Figure 17:
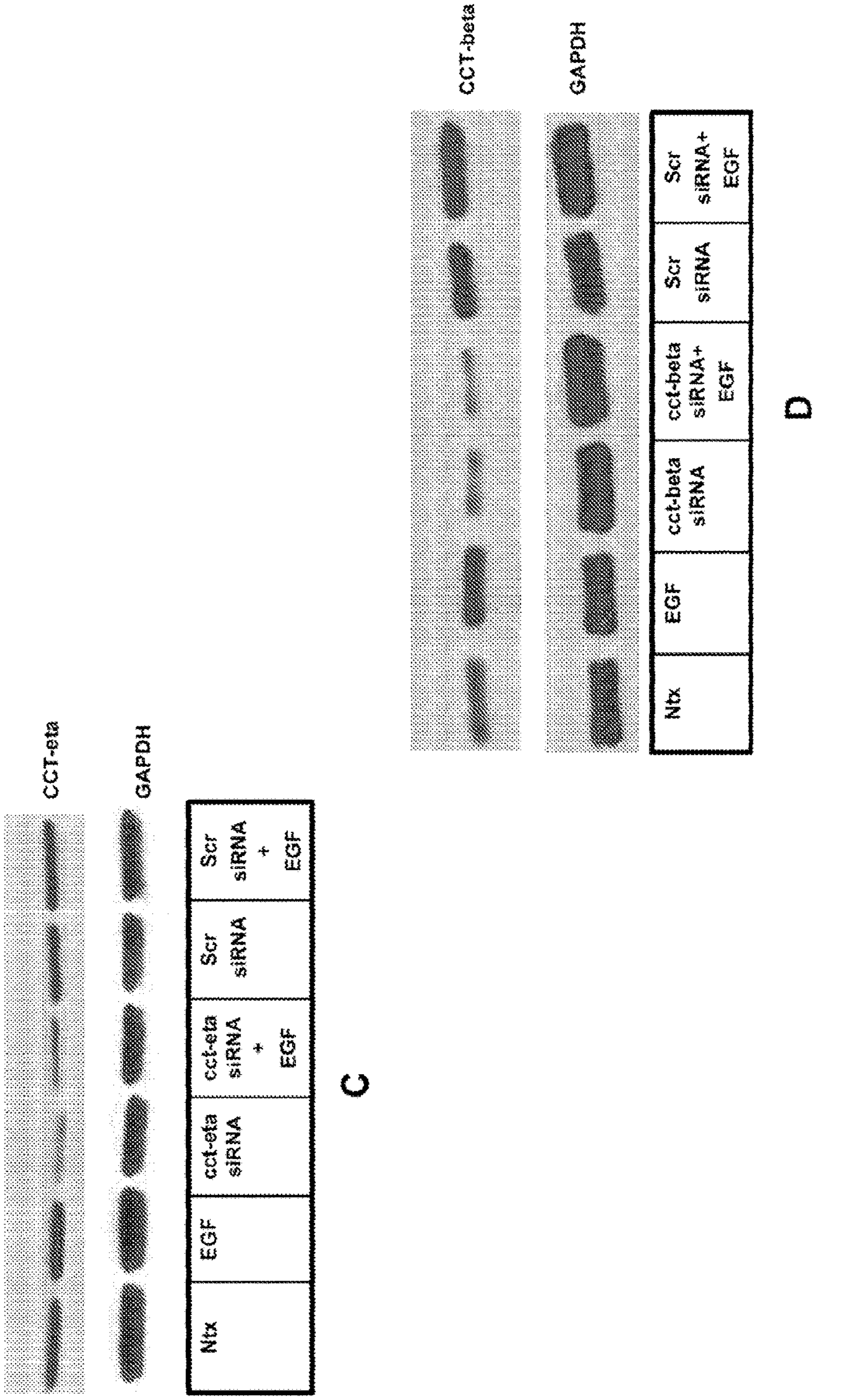

Primary cultures of fibroblasts obtained from fetal and adult rabbit skin were tested for motility in an in vitro wound healing assay (FIG. 16). Cells were treated with increasing concentrations of EGF and PDGF. The values are normalized to baseline motility and shown as EGF- and PDGF-induced cell motility at each concentration. Fetal and adult fibroblasts had essentially identical baseline motility, but only adult cells responded to growth factor stimulation. The values are mean±SEM of six independent studies each performed in triplicate. Statistical analyses were performed by Student's t-test.

qRT-PCR analysis of CCT-eta and CCT-beta mRNA levels showed effective inhibition of both basal expression and EGF-induction in siRNA-transfected adult fibroblasts (FIG. 17). siRNAs against CCT-eta (SEQ ID Nos. 1 and 2) and CCT-beta decrease both basal and EGF-induced mRNA and protein levels of their targets in fibroblasts. (FIGS. 17A and 17B). Results are expressed as relative quotient (RQ) of measured CCT-eta (SEQ ID No. 7) or CCT-beta mRNA and were calculated as a percentage of baseline control levels (100%). Values are means±SEM of six independent studies, each performed in duplicate. Statistical analyses were performed with Student's t test. Ntx-no transfection; EGF-EGF treatment (1 nM); siRNA-treatment with CCT-eta/CCT-beta siRNA; Scr-treatment with scrambled control siRNA. (FIGS. 17C and 17D). Western blot results using CCT-eta and CCT-beta antibody (1:500) showed effective reduction of CCT-eta and CCT-beta protein levels when siRNA was administered but no decrease when scrambled siRNA was employed. GAPDH was used as a loading control. In FIG. 17, a representative immunoblot of up to four similar such blots is shown for each analysis.

Figure 18:
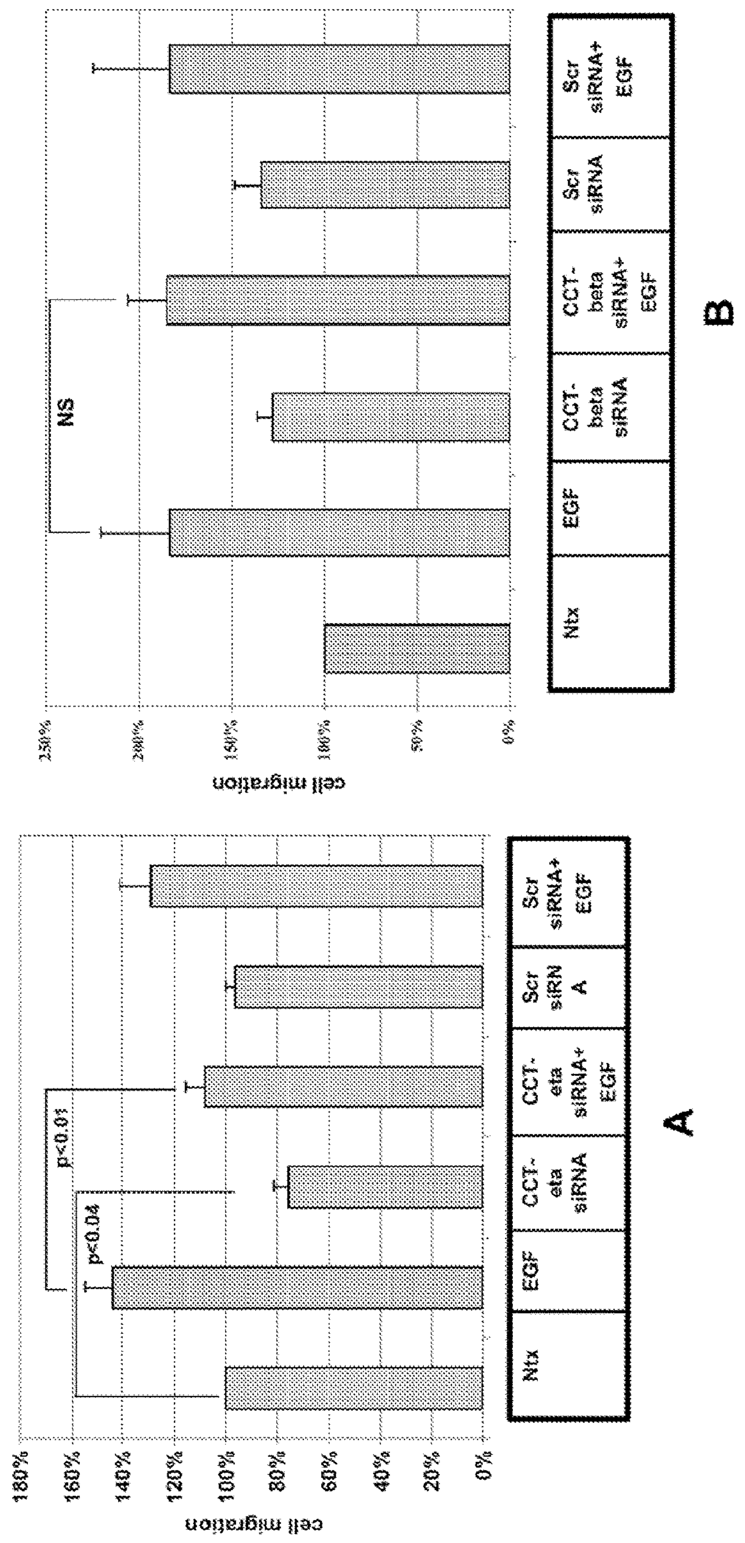
FIG. 18 illustrates siRNA against CCT-eta decreases EGF-induced fibroblast migration, whereas siRNA against CCT-beta does not appear to decrease EGF-induced fibroblast migration.
Figure 20:
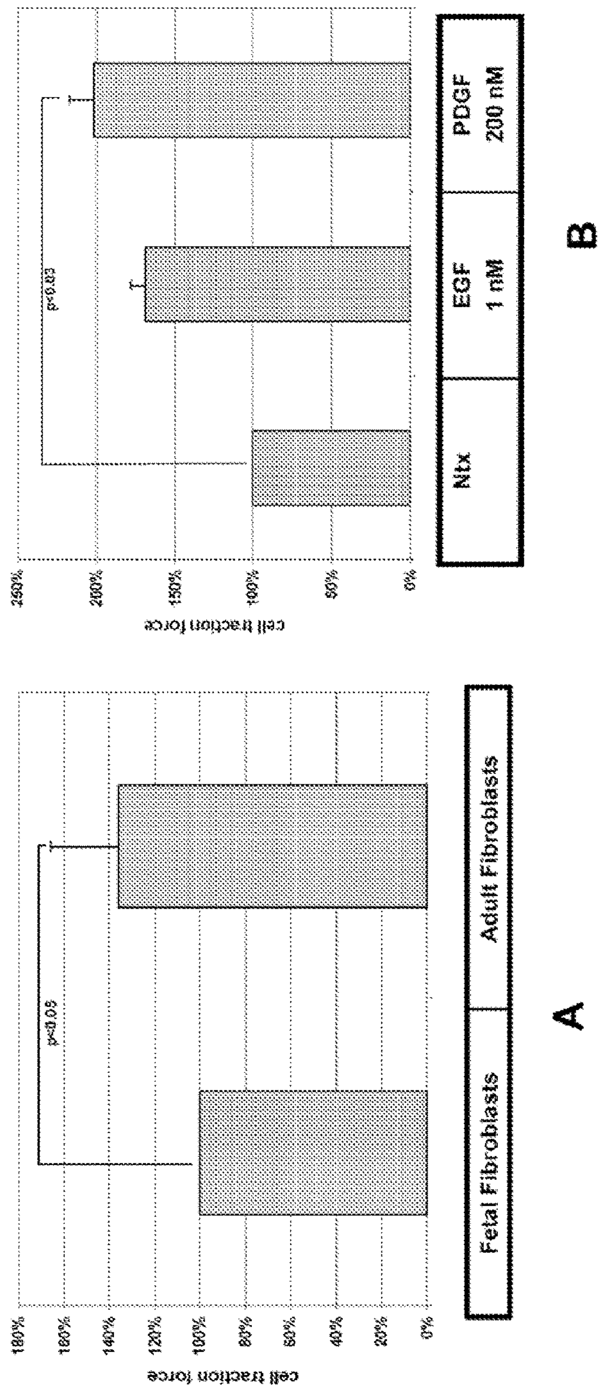
FIG. 20 illustrates that adult fibroblasts are more contractile than fetal fibroblasts.

Cells were incubated in the presence or absence of EGF (1 nM)+/−siRNA against CCT-eta (FIG. 18A) or CCT-beta (FIG. 18B) in an in vitro wound healing assay. siRNA against CCT-eta decreases EGF-induced fibroblast migration, whereas siRNA against CCT-beta does not. In all experiments, a subunit-specific scrambled siRNA sequence was used as control. In FIG. 18, cell motility is displayed as a relative percentage of baseline motility in the absence of EGF or siRNA exposure (100%). Active siRNA versus CCT-eta reduced both basal and EGF-induced motility; siRNA versus CCT-beta and scrambled controls had no effect. In FIG. 20, values are means±SEM of six independent studies, each performed in triplicate. Statistical analyses were performed with Student's t test.

Figure 19:
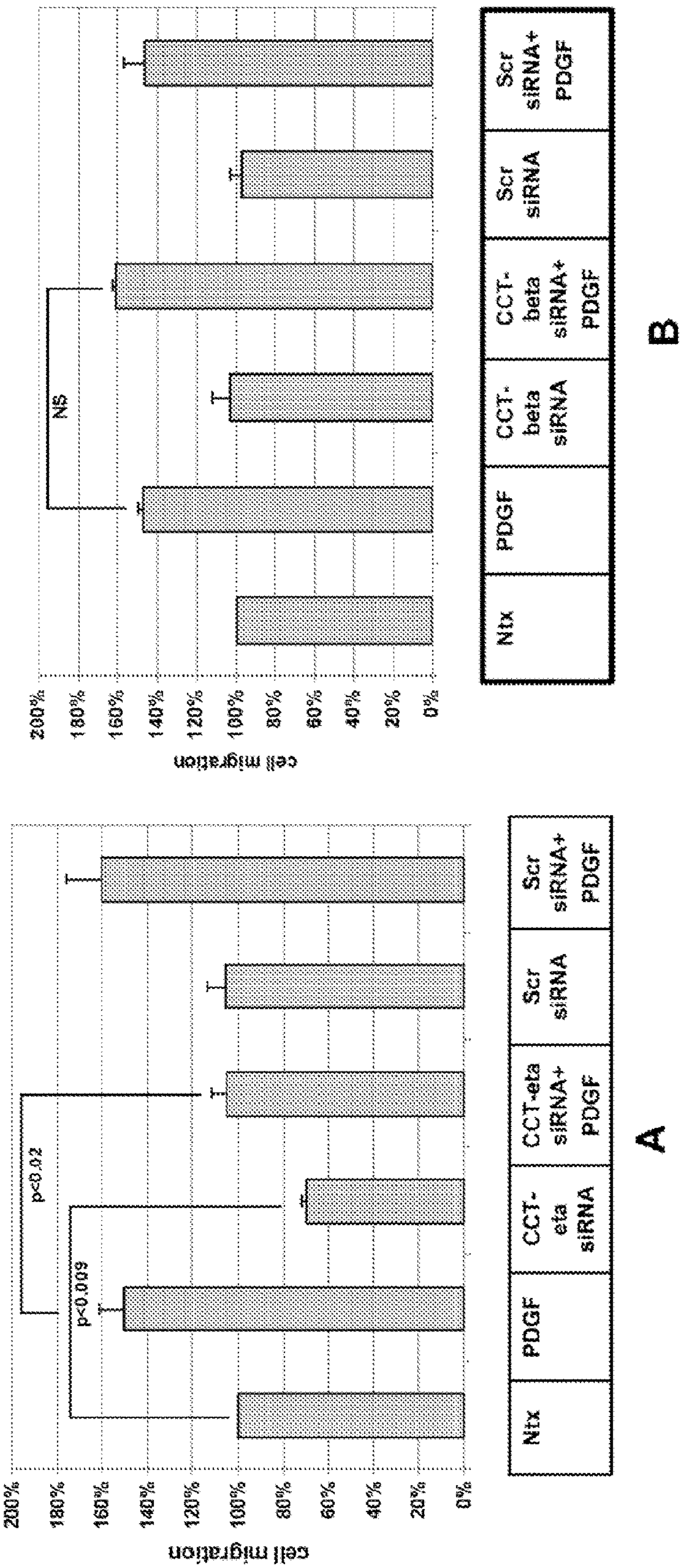
FIG. 19 illustrates siRNA against CCT-eta decreases PDGF-induced fibroblast migration, whereas siRNA against CCT-beta does not appear to decrease PDGF-induced fibroblast migration.

Cells were incubated in the presence or absence of PDGF (200 nM)+/−siRNA against CCT-eta (SEQ ID Nos. 1 and 2) (FIG. 19A) or CCT-beta (FIG. 19B) in an in vitro wound healing assay. siRNA against CCT-eta decreases PDGF-induced fibroblast migration, whereas siRNA against CCT-beta does not. In all experiments a subunit-specific scrambled siRNA sequence was used as control. In FIG. 19, cell motility is shown as a percentage of baseline migration in the absence of PDGF or siRNA exposure. As with EGF, active siRNA targeting CCT-eta inhibited basal and PDGF-induced motility, whereas CCT-beta siRNA and scrambled controls did not. Values are means±SEM of six independent studies, each performed in triplicate. Statistical analyses were performed with Student's t test.

Fetal fibroblasts are less contractile than adult fibroblasts as determined by traction force microscopy (FIG. 20A). Adult fibroblasts are more contractile than fetal fibroblasts. In FIG. 20A, each bar represents mean±SEM of more than 20 cells from two independent experiments. PDGF treatment of adult fibroblasts results in an increase in the observed cumulative traction force; EGF treatment results in a similar although smaller increase (FIG. 20B). In FIG. 20B, each bar represents mean±SEM of more than 25 cells from two different experiments. Statistical analyses were performed using Student's t test.

Figure 21:
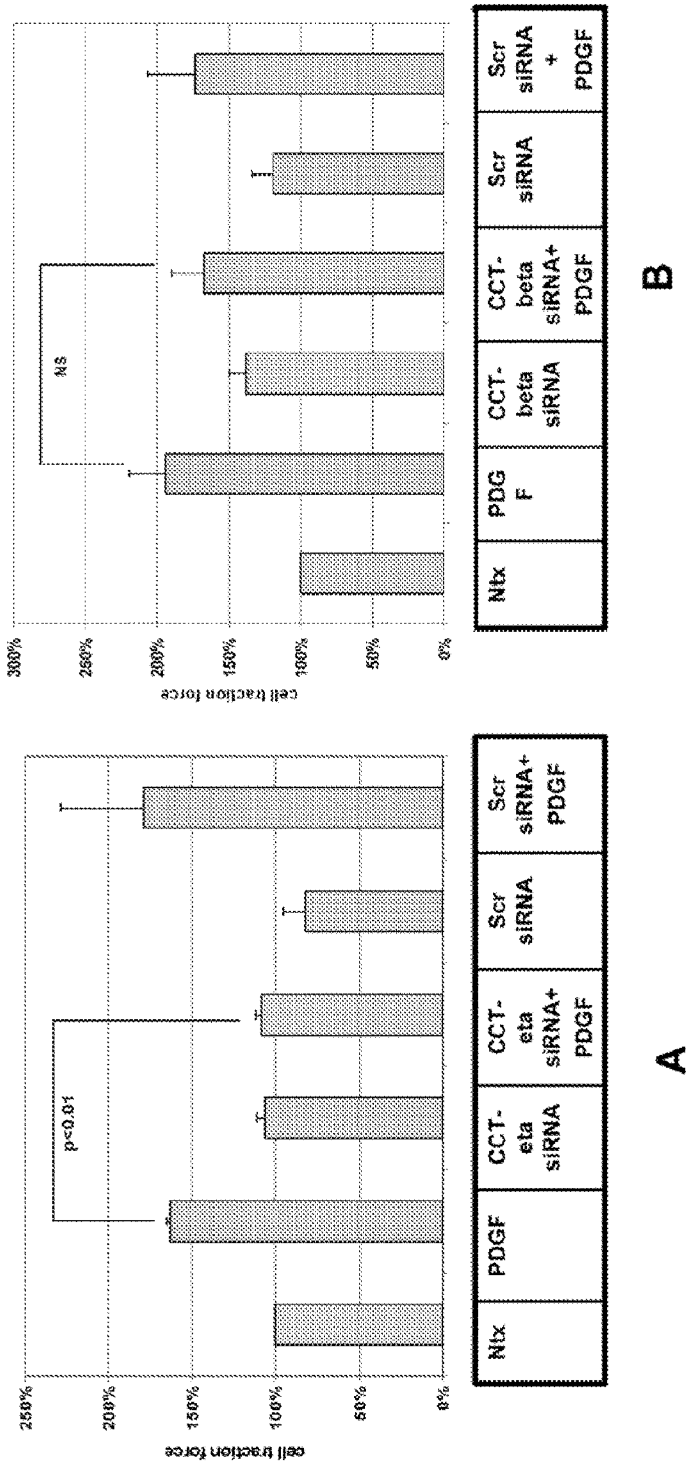
FIG. 21 illustrates siRNA against CCT-eta but not CCT-beta reduces PDGF-induced cellular traction force in adult fibroblasts.

Adult fibroblasts transfected with CCT-eta (SEQ ID Nos. 1 and 2) (FIG. 21A) or CCT-beta siRNA (FIG. 21B) along with pDSRed2-C1 were quantified for microdisplacement fields of red fluorescent cells on the green fluorescent substrate. siRNA against CCT-eta but not CCT-beta reduces PDGF-induced cellular traction force in adult fibroblasts. Each assay was repeated twice with more than 30 cells quantified in each experiment. CCT-eta siRNA abolished the increased cellular traction force seen with PDGF treatment (200 nM), whereas CCT-beta siRNA and scrambled controls did not. Values are means±SEM of two independent experiments with statistical analyses performed using Student's t test.

Figure 22:
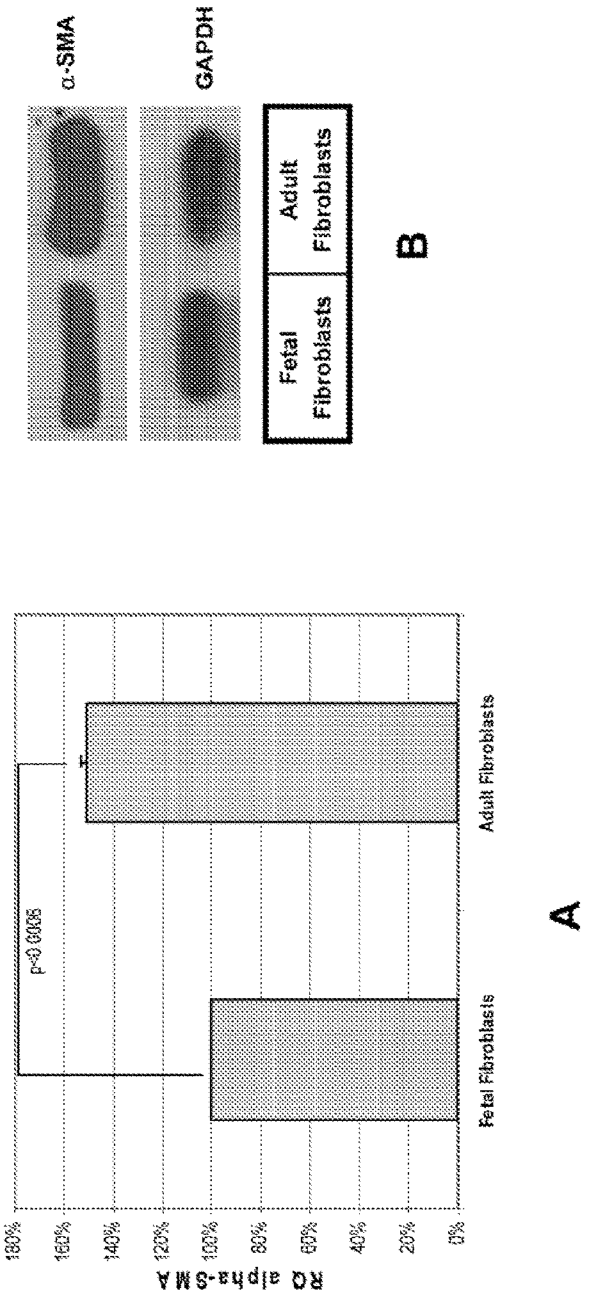
FIG. 22 illustrates that mRNA and protein levels show that α-SMA level is significantly increased in adult fibroblasts in comparison to fetal fibroblasts. NS=non-significant.
Figure 23:
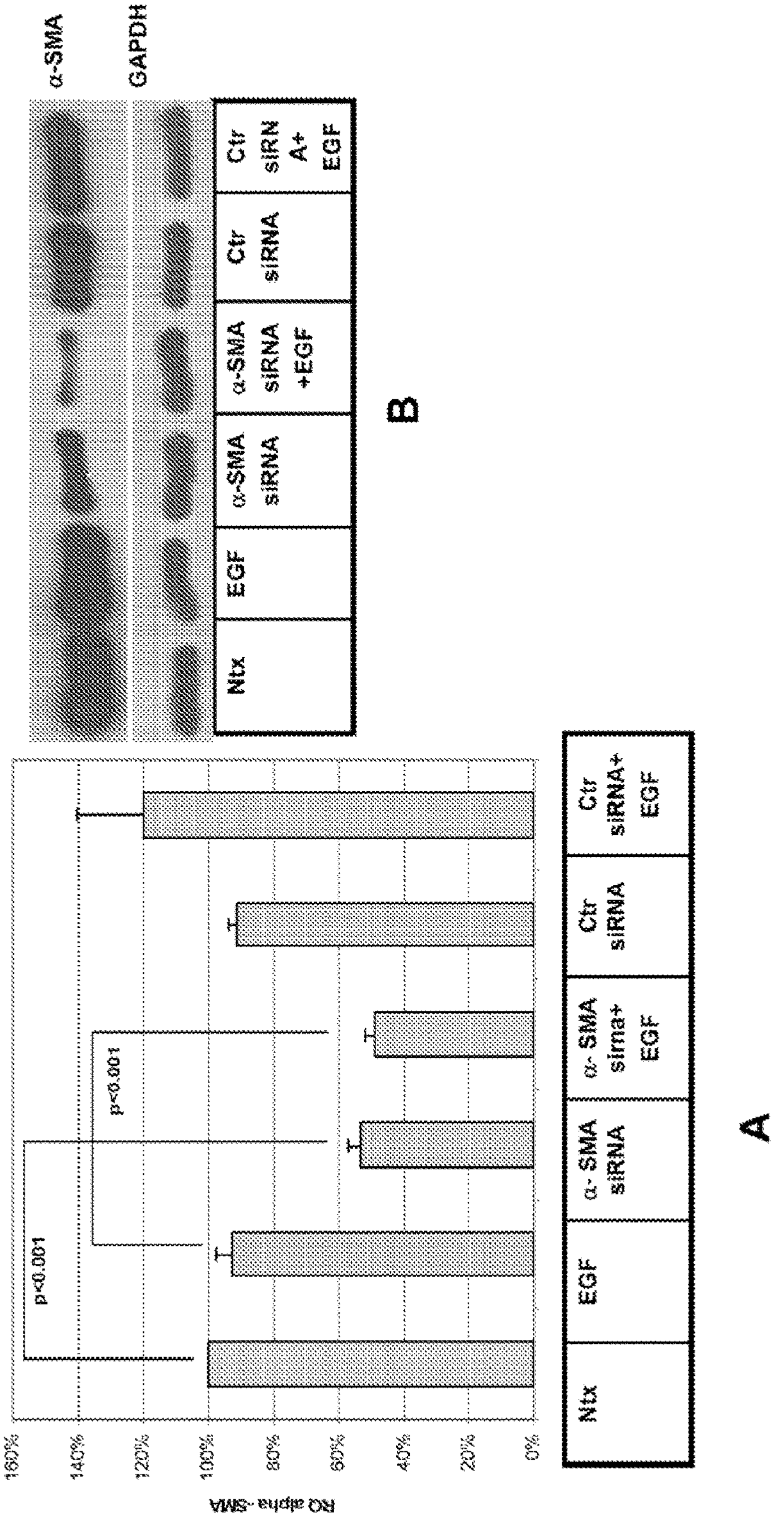
FIG. 23 illustrates siRNA against α-SMA specifically decreases both basal and EGF-induced mRNA and protein levels of α-SMA in adult fibroblasts.

RNA and protein extracted from fetal and adult fibroblasts were subjected to qRT PCR (FIG. 22A) and Western blot (FIG. 22B) analyses respectively. mRNA and protein levels show that α-SMA level is significantly increased in adult fibroblasts in comparison to fetal fibroblasts. The α-SMA mRNA levels (SEQ ID No. 8) were significantly more abundant in adult fibroblasts when compared to fetal fibroblasts (FIG. 22A). Values are means±SEM of three independent studies performed in duplicate. Statistical analyses were performed using Student's t test. Equal amounts of protein loaded from fetal and adult fibroblasts showed that adult fibroblasts express significantly greater α-SMA protein (SEQ ID No. 10) (FIG. 22B). GAPDH was used as loading control.

qRT-PCR analysis of α-SMA mRNA levels showed effective inhibition of both basal expression and EGF-induction in siRNA-transfected adult fibroblasts (FIG. 23A). Results are expressed as relative quotient (RQ) of measured α-SMA mRNA and were calculated as a percentage of baseline control levels (100%). Values are means±SEM of six independent studies, each performed in duplicate. Statistical analyses were performed with Student's t test. Ntx-no transfection; EGF-EGF treatment (1 nM); siRNA-treatment with α-SMA siRNA (SEQ ID Nos. 5 and 6); Ctr-treatment with a non-specific control siRNA. Western blot results using α-SMA antibody (1:500) showed effective reduction of α-SMA protein levels when siRNA was administered but no decrease when non-specific control siRNA was employed (FIG. 23B). GAPDH was used as a loading control. A representative immunoblot of up to four similar such blots is shown for each analysis. siRNA against α-SMA (SEQ ID Nos. 5 and 6) specifically decreases both basal and EGF-induced mRNA and protein levels of α-SMA in adult fibroblasts.

Figure 24:
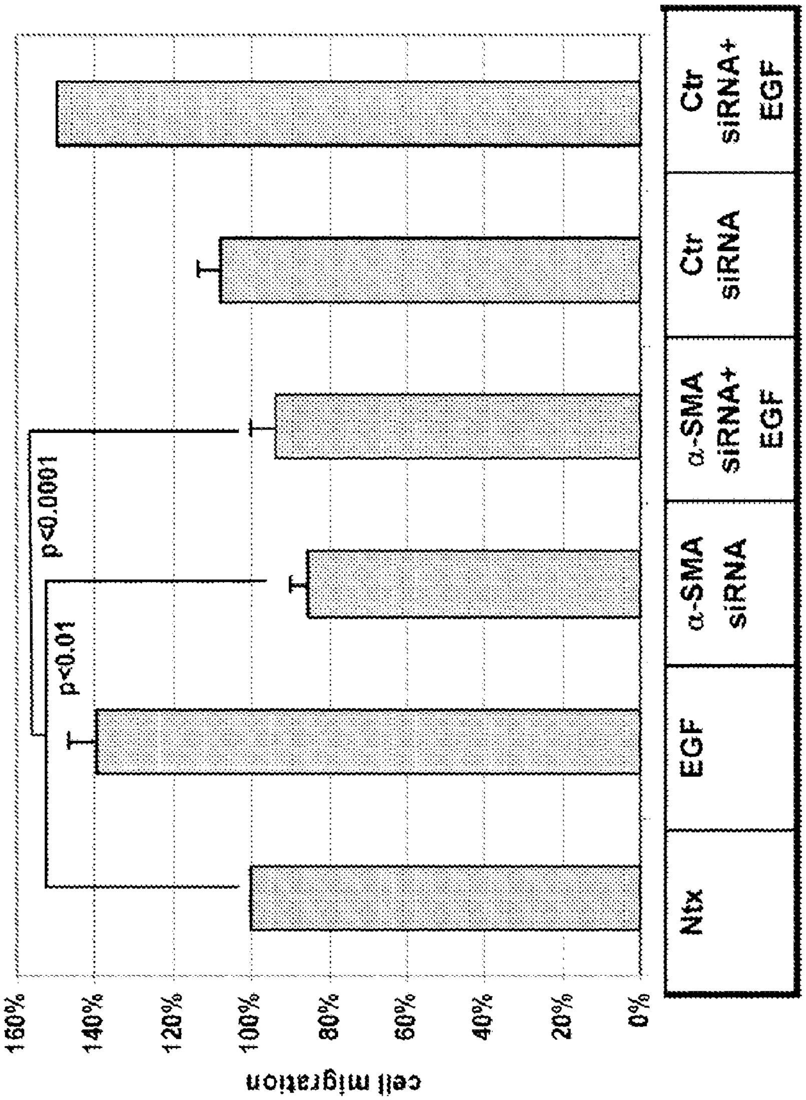
FIG. 24 illustrates siRNA against α-SMA inhibits both basal and EGF-induced cell migration in adult fibroblasts.

Cells were incubated in the presence or absence of EGF(1 nM)+/−siRNA against α-SMA in an in vitro wound healing assay (FIG. 24). In all experiments a non-specific control siRNA was used as a control. Cell motility is displayed as a relative percentage of baseline motility in the absence of EGF or siRNA exposure (100%). Active siRNA versus α-SMA reduced both basal and EGF-induced motility; a non-specific control siRNA had no such effect. Values are means±SEM of eight independent studies, each performed in duplicate. Statistical analyses were performed with Student's t test. siRNA against α-SMA (SEQ ID Nos. 5 and 6) inhibits both basal and EGF-induced cell migration in adult fibroblasts.

Example 12

The ability of siRNA versus CCT-eta (SEQ ID Nos. 1 and 2) delivered as a nanoparticle complex to modulate wound healing in a rabbit model was examined. The safety and efficacy of nanoparticle-mediated delivery of siRNA in reducing scar formation in animal models of skin injury was examined. Another objective was to determine the effect of CCT-eta down-regulation in a healing wound by examining its histological and biochemical properties.

Full-thickness incisional wounds on the dorsum of adult rabbits were topically treated with siRNA versus CCT-eta (SEQ ID No. 1 and 2) or control (scrambled siRNA) (SEQ ID Nos. 3 and 4) in an agarose matrix. Wounds were allowed to heal until closure (with attendant scar deposition) was complete, typically over about 4 weeks. Healed wound sites were then excised and were analyzed to characterize the resultant scar formation. With weekly administrations of active siRNA versus CCT-eta, persistently lowered CCT-eta and α-SMA mRNA and protein levels were found in comparison to scrambled siRNA. Hydroxyproline assay determined that total collagen content was less in CCT-eta siRNA treated wounds when compared to untreated and scrambled siRNA-treated wounds. Metamorph analysis of Masson's trichrome stained wound specimens similarly showed a decreased total collagen content in treated wounds. Tensiometry was used to examine the mechanical strength of healed wounds; surprisingly, wounds treated with CCT-eta siRNA actually showed increased tensile strength in comparison to untreated and scrambled siRNA-treated wounds. These data suggest that siRNA versus CCT-eta is an effective agent to mitigate scar formation and improve wound healing.

Methods: The dorsum of the adult rabbits was shaved and six-2 cm full-thickness incisional skin wounds were placed bilaterally, taking care to not violate the subcutaneous tissue.

CCT-eta siRNA Complexed in Low Melting Point Agarose:

siRNA was delivered to healing wounds via a gel-based formulation using prepared siRNA-lipofectamine nanoparticulate complexes embedded in an agarose matrix. 2.5 μl lipofectamine and 5.0 μl of CCT-eta siRNA (100 pmol) were mixed with 100 μl of OptiMEM. After incubating for 20 min at room temperature (to allow nanoparticles to assemble) the final siRNA/lipofectamine mixture was combined with 100 μl of 0.8% agarose transfection solution. After careful mixing 100 μl of gel-based mixture (final concentration: 50 pM siRNA in 0.4% agarose) was applied to 2 cm full thickness dorsal incisional wounds on adult New Zealand white rabbits. Animals were treated with the gel-based mixture on Day 0, Day 7, and Day 14. Wounds were allowed to heal over 28 days and the wounds were harvested on Day 29. Wound tissues were subjected to various biochemical and molecular analyses.

Hydroxyproline Analysis:

Total wound collagen accumulation on day 29 after administration of siRNA in rabbits was quantitatively analyzed using the hydroxyproline assay by Woessner's method 2. Results were expressed as micrograms of hydroxyproline per gm of wound/unwounded tissue.

Metamorph Analysis:

MetaMorph analysis software was used to assay the effect of CCT-eta siRNA on healing wound histology. This software scans the stained Masson's trichrome sections and summates its findings into a numerical value to evaluate the collagen deposits. Unwounded skin, control (untreated) wounds, and siRNA-treated wounds (CCT-eta or scrambled control) were compared.

Quantitative Real Time RT-PCR (qRT-PCR):

qRT-PCR was performed on 100 ng of total RNA isolated from control and treated tissue samples. The primers and Taqman probes for alpha SMA CCT-eta and CCT-beta were designed using Primer Express Software (Applied Biosystems, Foster City, Calif.). Forward and reverse primers were purchased from Integrated DNA Technologies (Coralville, Iowa) and fluorocoupled Taqman probes were purchased from Applied Biosystems. The reverse transcriptase (RT) reaction (using reverse primer) and subsequent real-time PCR assays were performed as previously described 3, 4, 5. Using the comparative critical cycle (Ct) method and using GAPDH as the endogenous control, the expression levels of the target genes were normalized and the relative abundance was calculated. Data were analyzed using the 7900 HT SDS software version 2.1 provided by Applied Biosystems.

Tensile Strength:

Tissue samples were bisected, wrapped flat in foil, snap-frozen in liquid nitrogen, and stored at −80° C. The frozen specimens were divided into three samples, the cross-sectional area was measured with calipers, and then the samples were clamped in a tensiometer and force-exerted until wound disruption. Measurements were recorded by a customized computer software program and tensile strength calculated using the formula: maximum tensiometer reading (converted to g) divided by cross-sectional area ($mm^2$) =tensile strength ($g/mm^2$) The results for individual specimens from one wound were combined to determine an average tensile strength per wound, which was tabulated for each group.

Figure 25:
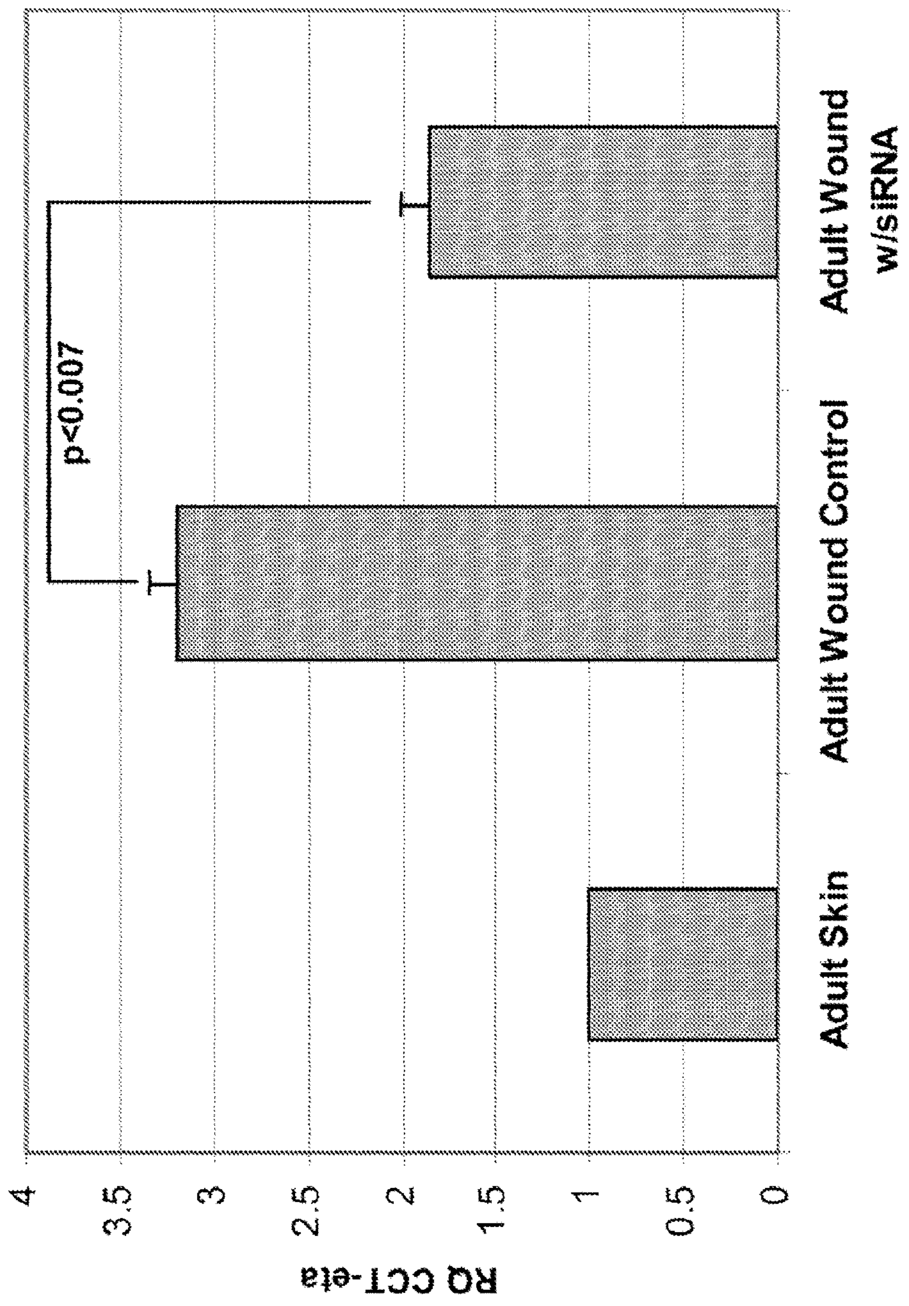
FIG. 25 illustrates the mRNA levels of CCT-eta in wounds treated with CCT-eta siRNA.
Figure 26:
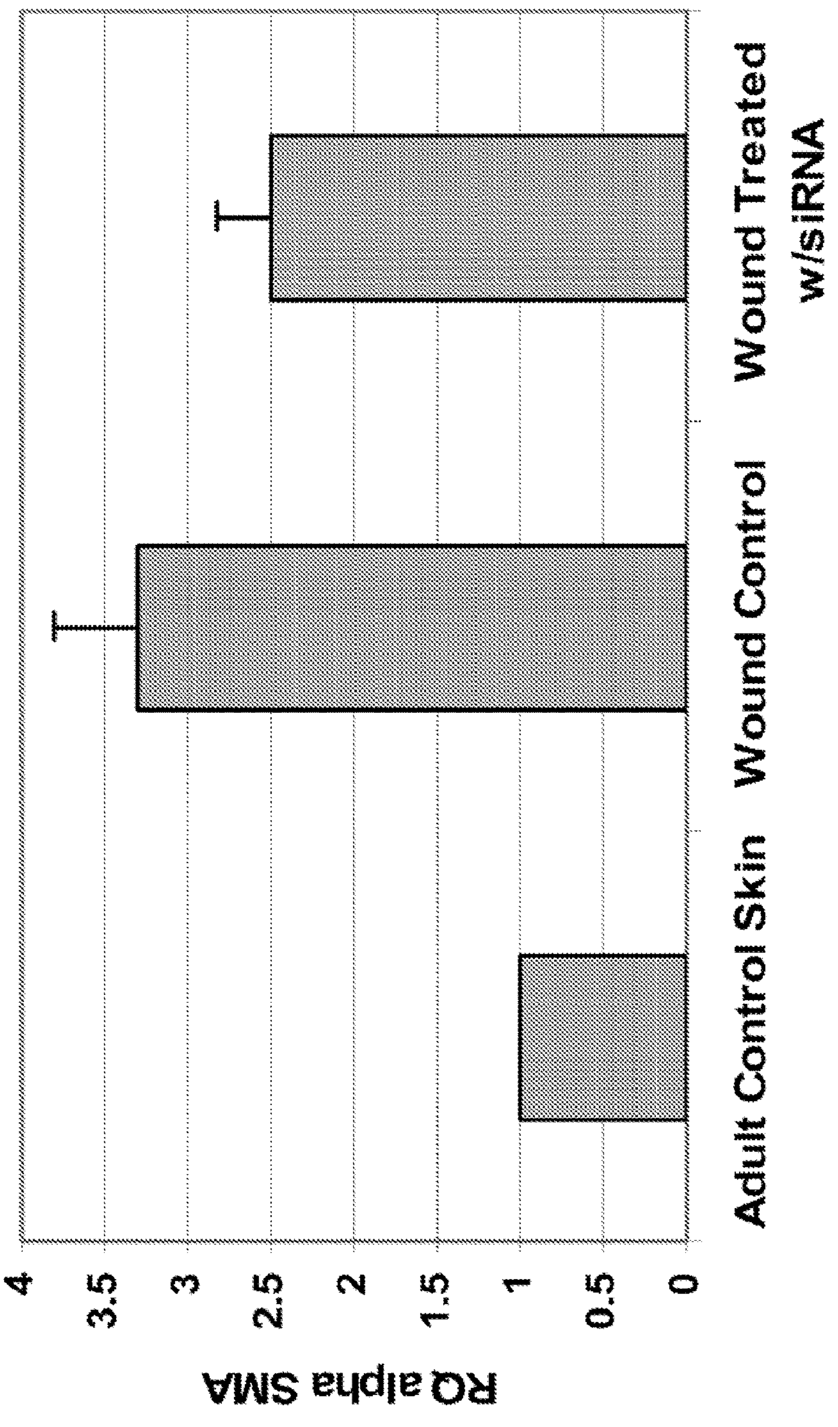
FIG. 26 illustrates the mRNA levels of α-SMA in wounds treated with CCT-eta siRNA.
Figure 30:
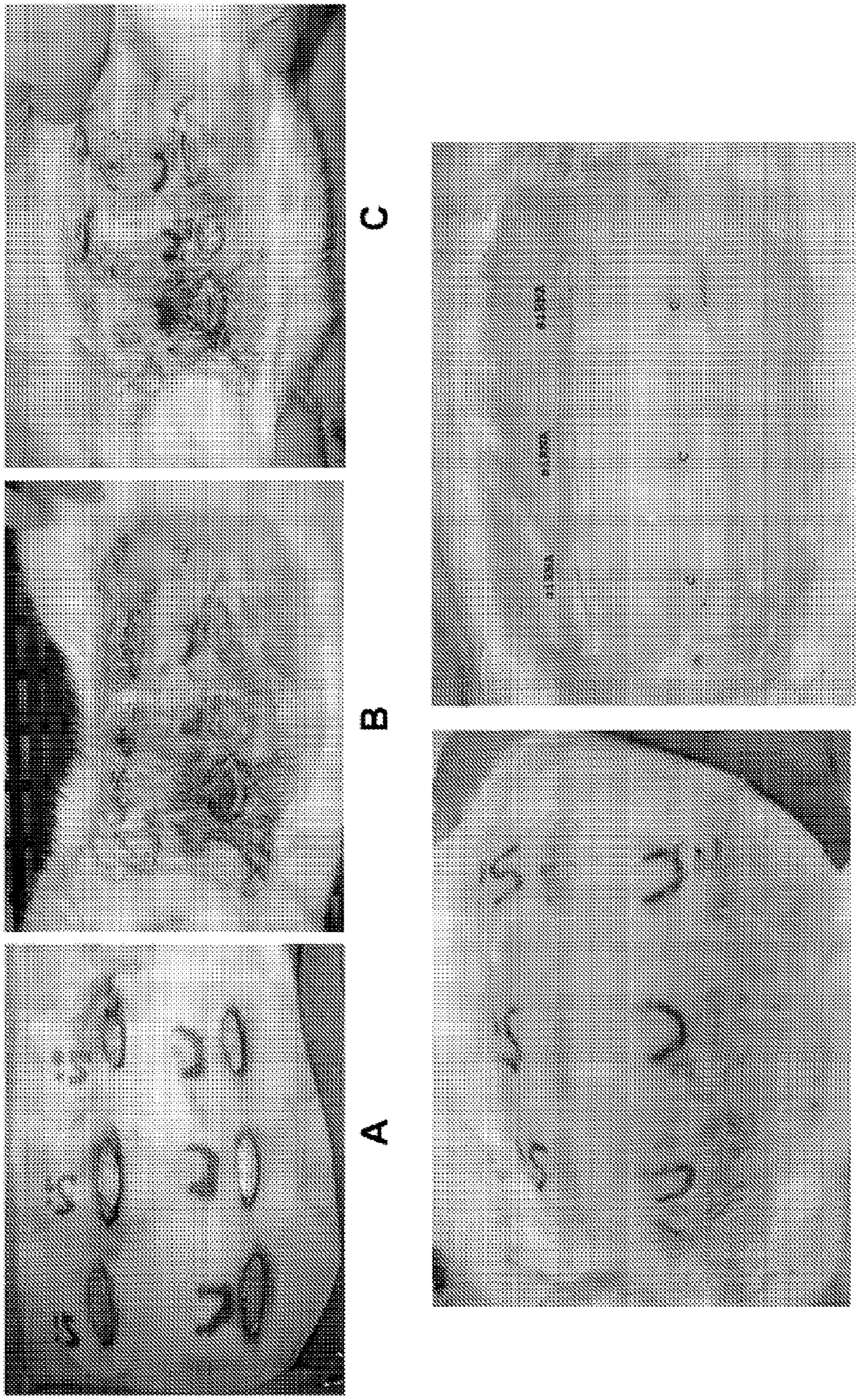
FIG. 30 includes photographs of full-thickness incisional CCT-eta siRNA treated wounds at intermittent time points from Day 0 to Day 28.

Results: CCT-eta siRNA (SEQ ID Nos. 1 and 2) treated wounds showed no toxicity and good wound closure (FIG. 30). Representative photographs are shown of full-thickness incisional wounds at intermittent time points up to Day 28. Wounds treated with CCT-eta siRNA showed no abnormal local inflammation and healed in a similar time course to control wounds.

mRNA levels of CCT-eta (SEQ ID No. 7) were considerably reduced in wounds treated with CCT-eta siRNA (FIG. 25). Quantitative real-time RT-PCR showed a relative increase in CCT-eta mRNA levels in wounded samples. Conversely, the increase in CCT-eta was substantially decreased when the wounds were treated with CCT-eta siRNA.

mRNA levels of alpha SMA (SEQ ID No. 8) were considerably reduced in wounds treated with CCT-eta siRNA (FIG. 26). Quantitative real time RT-PCR showed a relative increase in alpha-SMA levels in wounded samples. This increase in alpha-SMA was substantially blunted when the wounds were treated with CCT-eta siRNA.

Figure 27:
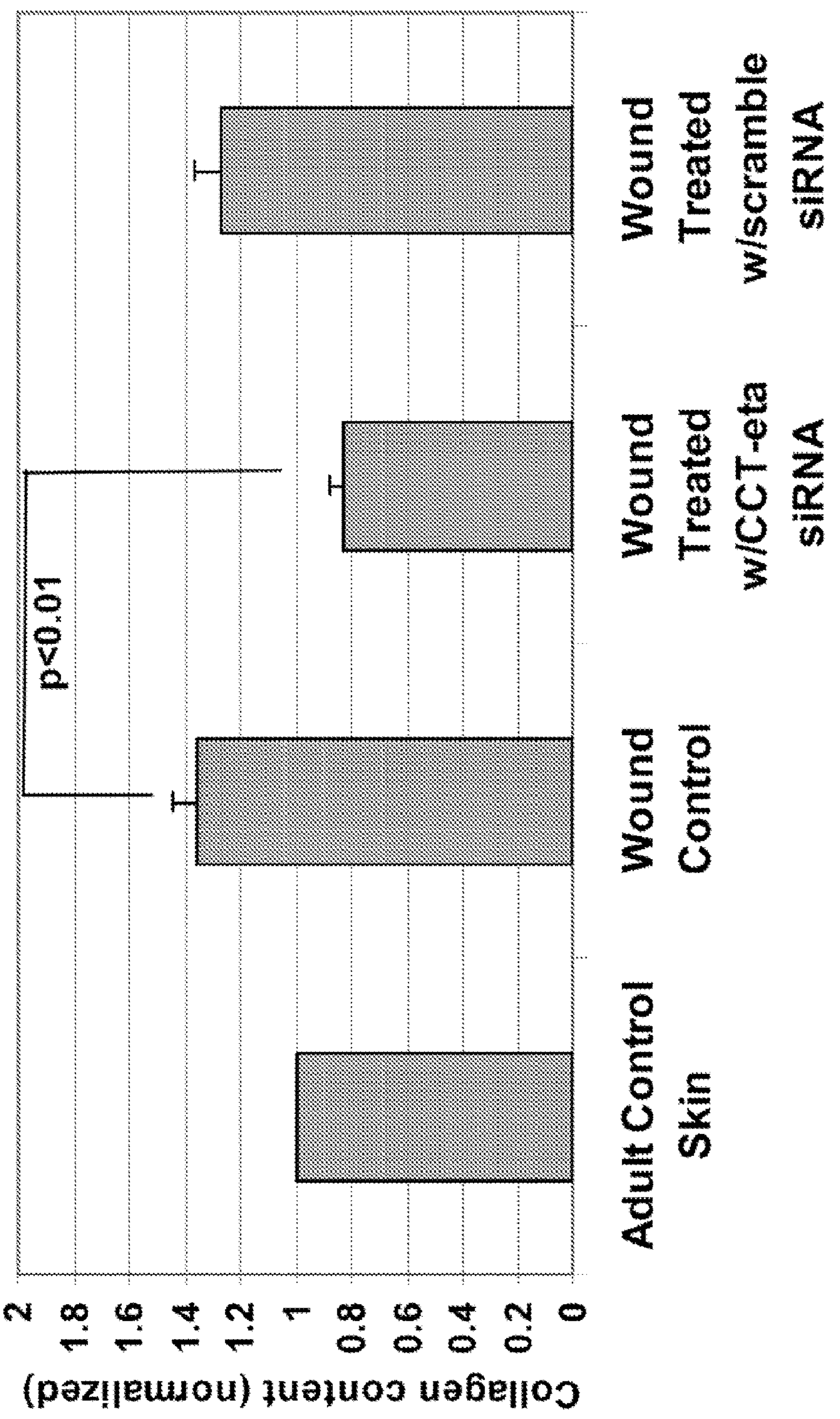
FIG. 27 illustrates the amount of collagen in CCT-eta siRNA treated wounds as determined by MetaMorph analysis.

CCT-eta siRNA treated wounds displayed less collagen content as determined by MetaMorph analysis (FIG. 27). Healing wounds with no intervention display a 40% increase in the MetaMorph summated value (to ~1.4). CCT-eta siRNA (SEQ ID Nos. 1 and 2) abolishes that increase, returning to a value similar to unwounded skin. Scrambled control siRNA (SEQ ID Nos. 3 and 4) had no effect compared to untreated wound.

Figure 28:
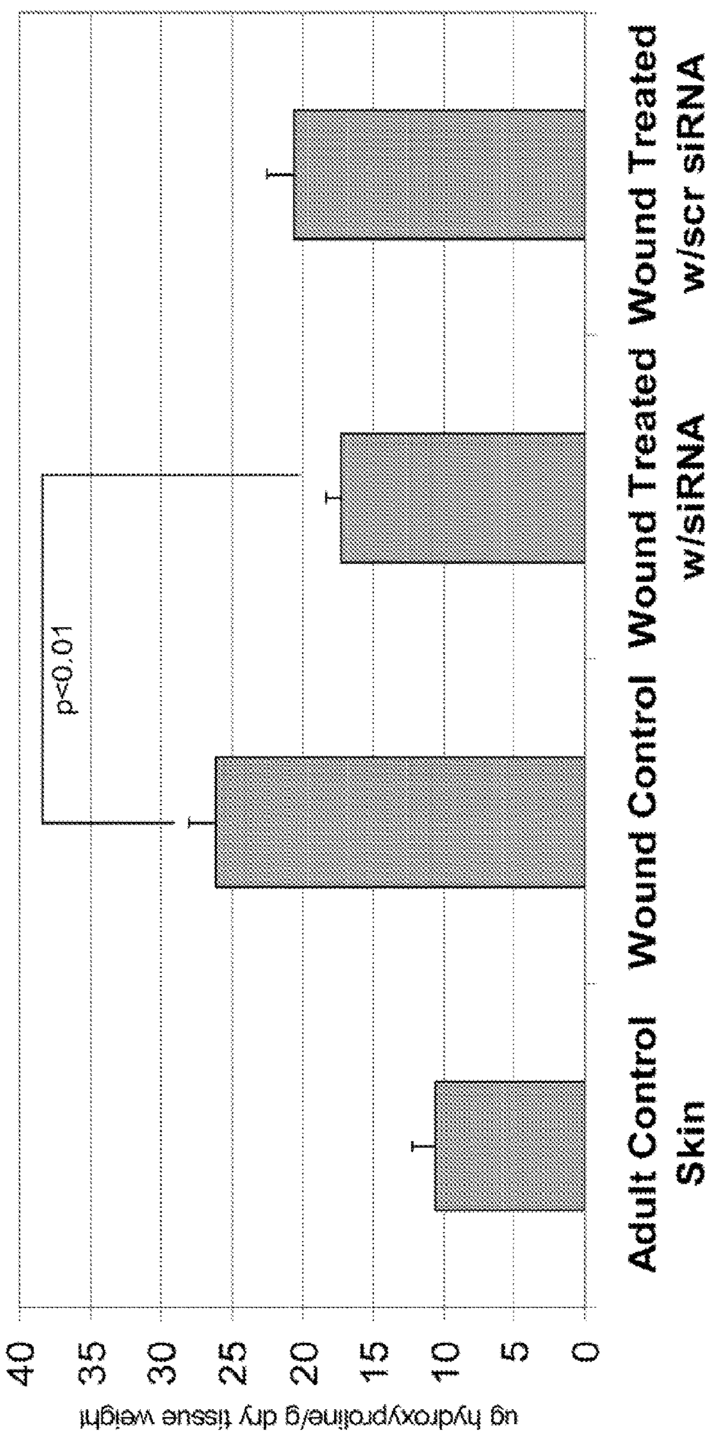
FIG. 28 illustrates the amount of hydroxyproline in adult wounds treated with CCT-eta siRNA.

Reduction of CCT-eta levels in adult wounds decreased hydroxyproline content (FIG. 28). Levels of hydroxyproline were measured as described on skin samples obtained from unwounded, wounded controls and siRNA treated samples. Total tissue hydroxyproline, reflecting total tissue collagen content, was decreased by treatment with CCT-eta siRNA.

Figure 29:
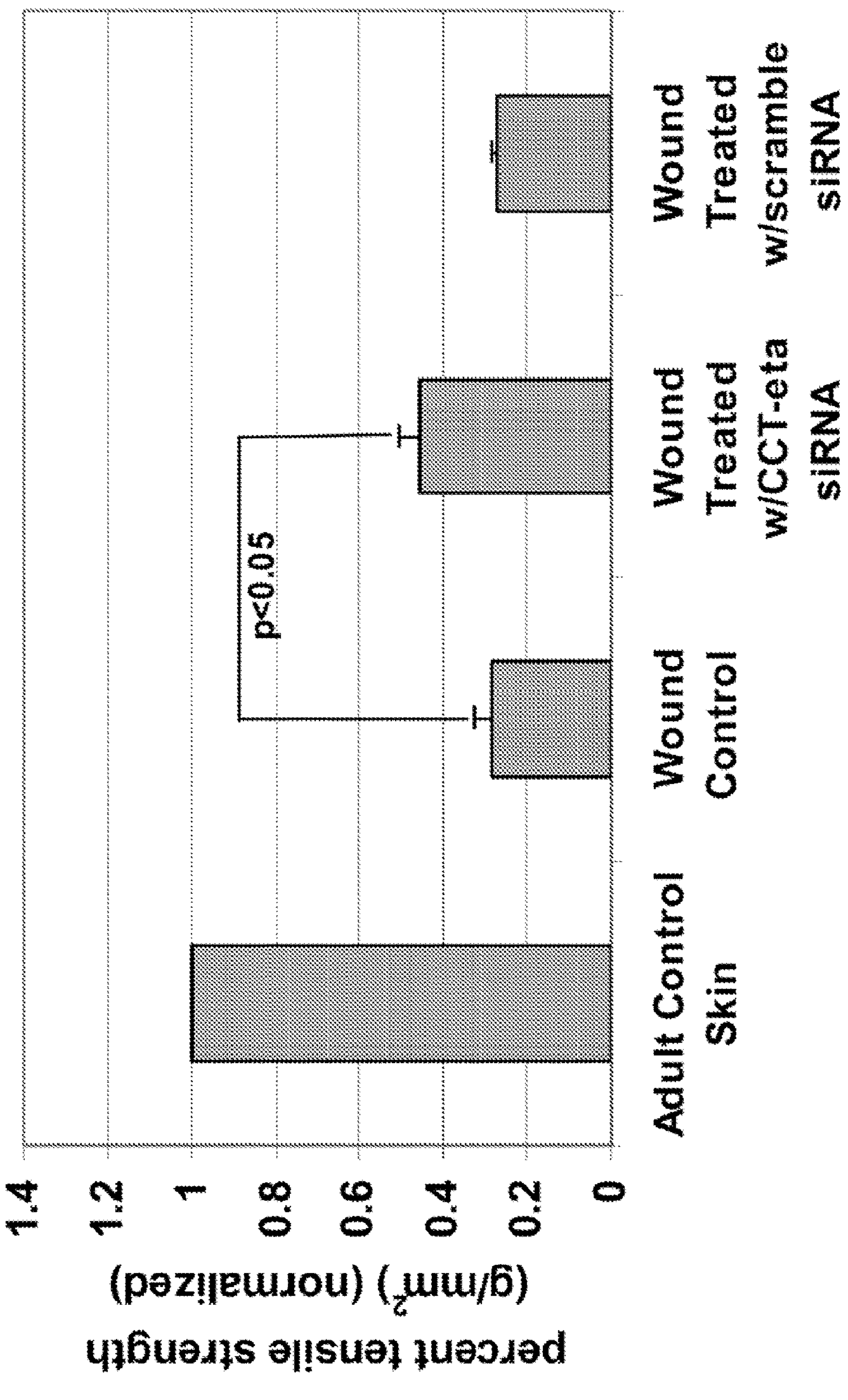
FIG. 29 illustrates the normalized percentage of tensile strength in CCT-eta siRNA-treated wounds.

Increase in tensile strength was noted in CCT-eta siRNA-treated wounds (FIG. 29). CCT-eta siRNA treated wounds showed an ~50% greater re-accumulation of tensile strength compared to control wounds. Wounds treated with scrambled siRNA are indistinguishable from untreated control wounds.

Conclusion: qRT-PCR confirmed an increase of CCT-eta mRNA levels in healing wounds. qRT-PCR confirmed a relative decrease of CCT-eta mRNA levels in wounds treated with CCT-eta siRNA compared to controls. Repeated administration of siRNA complex coupled with agarose gel matrix improved reduction of the expression of CCT-eta by siRNA in full thickness incisional wounds. mRNA levels of alpha-SMA were considerably reduced in wounds treated with CCT-eta siRNA. Biochemical analysis showed reduction in the levels of hydroxyproline content in wounds treated with CCT-eta siRNA, signifying a lower total collagen content. Gross and histological examination of the wounds showed no evidence of any abnormal tissue inflammation or toxicity. MetaMorph analysis showed that CCT-eta siRNA effects a favorable re-organization of wound collagen. Downregulating CCT-eta actually improved the mechanical properties of healing wounds as measured by tensile strength.

Example 13

Figure 31:
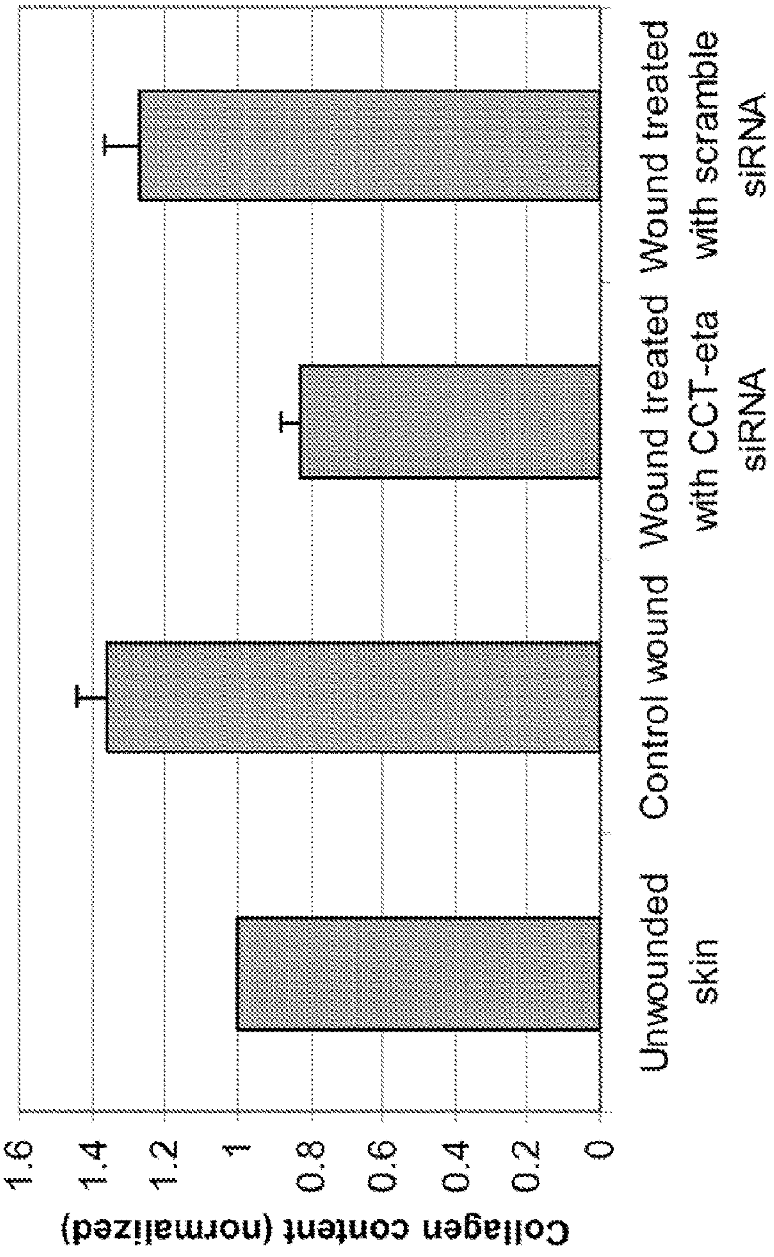
FIG. 31 illustrates the effect of CCT-eta siRNA on wound collagen content and organization as measured by Meta-Morph analysis.

An assay was conducted to determine the effect of CCT-eta siRNA on healing wounds using MetaMorph analysis software, which scans histology sections for collagen content and organization, summating its findings into a numerical value. Unwounded skin, control (untreated) wounds, and siRNA-treated wounds (CCT-eta or scrambled control) were collected 30 days post-wounding. Excised tissues were fixed in 10% formalin-buffered saline, embedded in paraffin blocks, and stained with Masson's trichrome staining to evaluate the collagen deposits. This demonstrated that total collagen increased and became more ordered in healing wounds compared to unwounded control (consistent with known features of scar formation), but that CCT-eta siRNA is able to reverse this pattern of collagen deposition. Scrambled siRNA had no such effect (FIG. 31). In FIG. 31, MetaMorph analysis of unwounded skin is standardized at a value of 1. Healing wounds with no intervention display a 40% increase in the MetaMorph summated value (to ~1.4). CCT-eta siRNA abolishes that increase, returning to a value similar to unwounded skin. Scrambled control siRNA had no effect compared to untreated wound.

Figure 32:
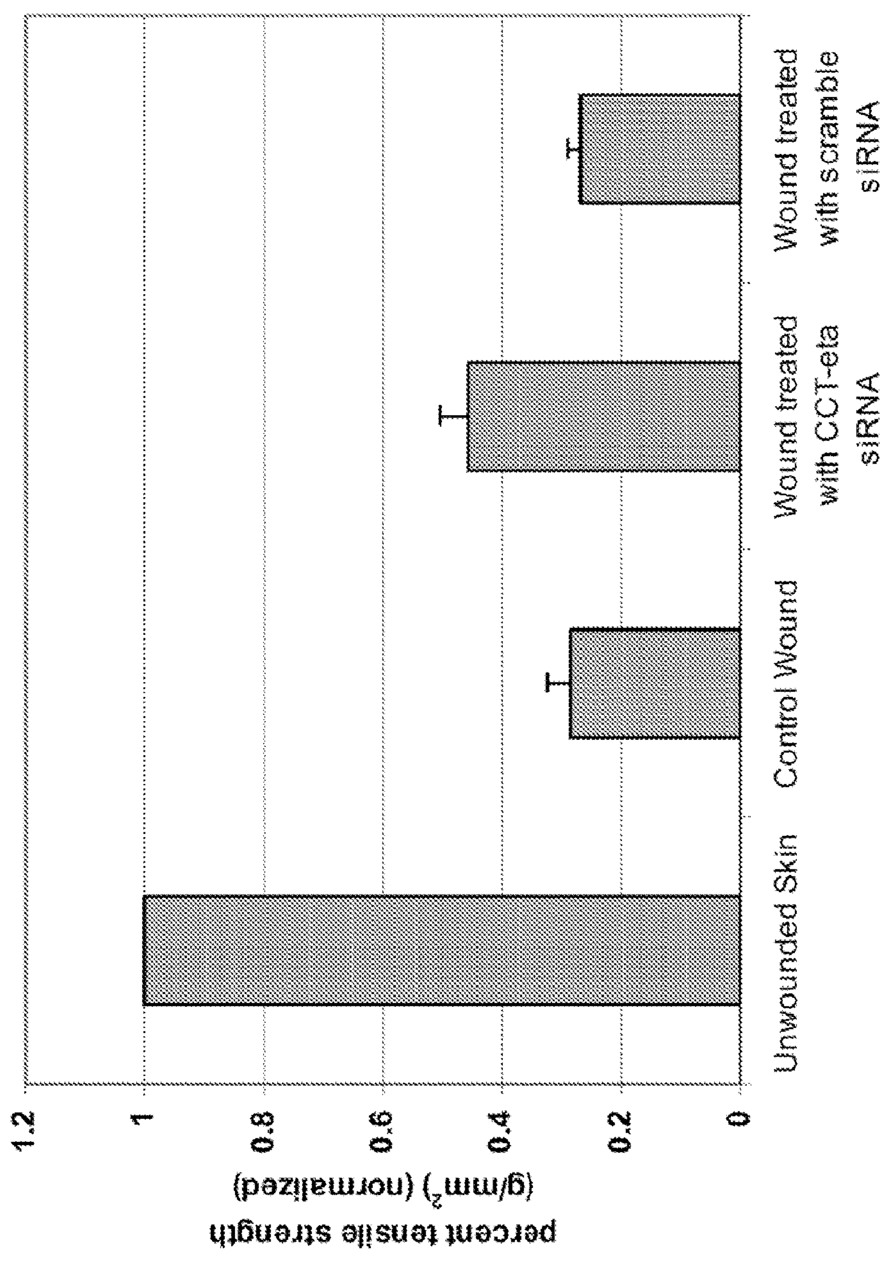
FIG. 32 illustrates the effect of CCT-eta siRNA on wound tensile strength.

The tensile strength of unwounded skin was compared with that of healing wounds, both untreated and siRNA-treated. Tissue samples were bisected, wrapped flat in foil, snap-frozen in liquid nitrogen, and stored at −80° C. For tensile strength measurements, frozen specimens were divided into three samples, the cross-sectional area was measured with calipers, and then the samples were clamped in a tensiometer and force-exerted until wound disruption. Measurements were recorded by a customized computer software program and tensile strength calculated using the formula: maximum tensiometer reading (converted to g) divided by cross-sectional area (mm2)=tensile strength (g/mm2) The results for individual specimens from one wound were combined to determine an average tensile strength per wound, which was tabulated for each group. Results are shown in FIG. 32. In FIG. 32, the tensile strength of unwounded skin is normalized to a value of 1. Untreated control wounds at 30 days post-wounding show a marked reduction in tissue tensile strength to some 30% of unwounded skin. CCT-eta siRNA-treated wounds show an ~50% greater re-accumulation of tensile strength compared to control wounds. Wounds treated with scrambled siRNA are indistinguishable from untreated control wounds. Administration of the CCT-eta siRNA (SEQ ID Nos. 1 and 2), while altering the collagen profile of the healing wounds, actually increased the tensile strength of the experimental wounds compared to untreated control wounds and scrambled siRNA-treated wounds.

Conclusion: MetaMorph analysis validated that CCT-eta siRNA (SEQ ID Nos. 1 and 2) effects a favorable re-organization of wound collagen. CCT-eta siRNA was demonstrated to actually improve the mechanical properties of healing wounds as measured by tensile strength.

Although the present disclosure has been described in considerable detail with reference to certain preferred embodiments thereof, other versions are possible. Therefore the spirit and scope of the appended claims should not be limited to the description and the preferred versions contained within this specification.

What is claimed is:

1. A method of inhibiting one of: (i) motility and (ii) contraction of one of: (X) fibroblasts and (Y) myofibroblasts in eukaryotic tissue, comprising administering a therapeutically effective amount of an agent that inhibits at least one of:

(A) CCT-eta mRNA, CCT-eta protein or a combination thereof, further comprising an siRNA comprising a sense strand comprising SEQ ID No. 1 and an antisense strand comprising SEQ ID No. 2;

(B) α-SMA mRNA, α-SMA protein or a combination thereof further comprising an siRNA comprising a sense strand comprising SEQ ID No. 5 and an antisense strand comprising SEQ ID No. 6.

2. The method of claim 1, wherein said inhibition causes the reduction of one of: (i) scarring and (ii) fibrosis.

3. The method of claim 2, wherein the fibrosis is selected from Dupuytren's contracture, Peyronie's disease, pulmonary fibrosis, cirrhosis, interstitial lung disease or scarring alopecia.

4. The method of claim 1, wherein the agent that inhibits CCT-eta mRNA, CCT-eta protein or any combination thereof comprises a short hairpin RNA.

5. The method of claim 1, further comprising the steps of:

(a) fabricating a vector, at least a portion of which corresponds, by transcription to said strand of siRNA;

(b) embedding said vector in a matrix of a nanoparticulate polysaccharide delivery agent which facilitates the in vivo uptake of said vector; and (c) administering said vector embedded in said matrix of nanoparticulate polysaccharide delivery agent to said eukaryotic tissue.

6. The method of claim 5, wherein the vector is selected from a plasmid vector or a viral vector.

* * * * *